(12) United States Patent
Chen

(10) Patent No.: US 12,086,788 B2
(45) Date of Patent: Sep. 10, 2024

(54) SUBSTITUTED PYRAZINES AS INHIBITORS OF BTK, AND MUTANTS THEREOF

(71) Applicant: Newave Pharmaceutical Inc., Pleasanton, CA (US)

(72) Inventor: Yi Chen, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 0 days.

(21) Appl. No.: 17/962,798

(22) Filed: Oct. 10, 2022

(65) Prior Publication Data

US 2023/0140433 A1 May 4, 2023

Related U.S. Application Data

(60) Division of application No. 16/996,516, filed on Aug. 18, 2020, now Pat. No. 11,501,284, which is a continuation of application No. PCT/US2019/018139, filed on Feb. 15, 2019.

(60) Provisional application No. 62/631,945, filed on Feb. 19, 2018.

(51) Int. Cl.
| | |
|---|---|
| *A61K 31/497* | (2006.01) |
| *A61P 35/04* | (2006.01) |
| *C07D 241/20* | (2006.01) |
| *C07D 403/04* | (2006.01) |
| *G06K 19/07* | (2006.01) |
| *G06Q 20/34* | (2012.01) |

(52) U.S. Cl.
CPC ............ *G06Q 20/349* (2013.01); *A61P 35/04* (2018.01); *C07D 403/04* (2013.01); *G06K 19/0723* (2013.01); *G06Q 20/341* (2013.01)

(58) Field of Classification Search
CPC ........................... A61K 31/497; C07D 241/20
USPC ........................ 514/255.06; 544/407
See application file for complete search history.

(56) References Cited

U.S. PATENT DOCUMENTS

| | | |
|---|---|---|
| 9,260,415 B2 | 2/2016 | Crawford et al. |
| 11,501,284 B2 | 11/2022 | Chen |
| 2015/0005279 A1 | 1/2015 | Bonafoux et al. |
| 2020/0377478 A1 | 12/2020 | Chen |
| 2022/0135569 A1 | 5/2022 | Chen |

FOREIGN PATENT DOCUMENTS

| | | |
|---|---|---|
| WO | 2008/121742 A2 | 10/2008 |
| WO | 2009/158571 A1 | 12/2009 |
| WO | 2011/140488 A1 | 11/2011 |
| WO | 2013/067274 A1 | 5/2013 |
| WO | 2014/135474 A1 | 9/2014 |
| WO | 2015/050703 A1 | 4/2015 |
| WO | 2015/082583 A1 | 6/2015 |
| WO | 2018/109050 A1 | 6/2018 |
| WO | 2019/148150 A1 | 8/2019 |
| WO | 2019/161152 A1 | 8/2019 |
| WO | 2020/176403 A1 | 9/2020 |
| WO | 2021/066958 A1 | 4/2021 |
| WO | 2021/091575 A1 | 5/2021 |

OTHER PUBLICATIONS

Hackam, et al. JAMA, 296(14), 2006, 1731-1732.*
Arthur et al., Development of PROTACs to address clinical limitations associated with BTK-targeted kinase Inhibitors. Explor Target Antitumor Ther. Jun. 29, 2020;1:131-152.
Dorwald, Side Reactions in Organic Synthesis, A Guide to Successful Synthesis Desing. Wiley-VCH Verlag GmbH & Co. KGaA, Weinheim. p. IX, (2005).
Huang et al., A Chemoproteomic Approach to Query the Degradable Kinome Using a Multi-kinase Degrader. Cell Chem Biol. Jan. 18, 2018;25(1):88-99.e6.
Jordan, Tamoxifen: a most unlikely pioneering medicine. Nat Rev Drug Discov. Mar. 2003;2(3):205-13.
Sandoval et al., Two-Step Synthesis of 3,4-Dihydropyrrolopyrazinones from Ketones and Piperazin-2-ones. Org Lett. 2018;20(4):1252-1255.
Vippagunta et al., Crystalline solids. Adv Drug Deliv Rev. May 16, 2001;48(1):3-26.
Wolff, Burger's Medicinal Chemistry and Drug Discovery, Fifth Edition, vol. I: Principles and Practice. John Wiley & Sons, Inc., New York. pp. 975-977, (1995).
International Search Report and Written Opinion for Application No. PCT/US2019/018139, dated Apr. 23, 2019, 11 pages.
International Search Report and Written Opinion for Application No. PCT/US2020/019478, dated Jun. 22, 2020, 12 pages.
International Search Report and Written Opinion for Application No. PCT/US2020/047196, dated Sep. 25, 2020, 10 pages.

(Continued)

*Primary Examiner* — Douglas M Willis
(74) *Attorney, Agent, or Firm* — McCarter & English, LLP; Yu Lu; Zhongyu "Alex" Wang

(57) ABSTRACT

The disclosure includes compounds of Formula (I)

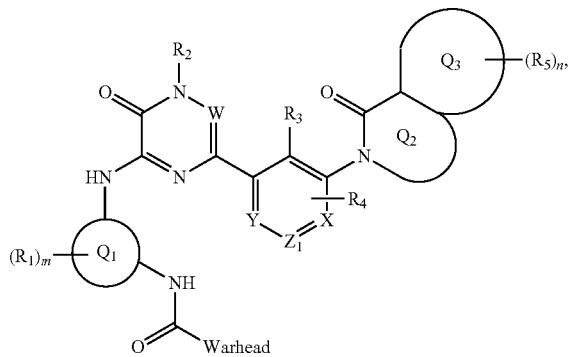

wherein $Q_1$, $Q_2$, $Q_3$, W, X, Y, $Z_1$, m, n, Warhead, $R_1$, $R_2$, $R_3$, $R_4$, and $R_5$, are defined herein. Also disclosed is a method for treating a neoplastic disease, autoimmune disease, and inflammatory disorder with these compounds.

23 Claims, No Drawings

(56) References Cited

OTHER PUBLICATIONS

International Search Report and Written Opinion for Application No. PCT/US2021/045867, dated Nov. 25, 2021, 14 pages.
International Search Report and Written Opinion for Application No. PCT/US2021/057187, dated Mar. 21, 2022, 20 pages.
International Search Report and Written Opinion for Application No. PCT/US2021/063984, dated Mar. 22, 2022, 11 pages.

* cited by examiner

SUBSTITUTED PYRAZINES AS INHIBITORS OF BTK, AND MUTANTS THEREOF

CROSS-REFERENCES TO RELATED APPLICATIONS

This application is a continuation application of International Application No. PCT/US2019/018139, filed on Feb. 15, 2019, which claims the benefit of the filing date under 35 U.S.C. 119(e) to U.S. Provisional Patent Application No. 62/631,945, filed on Feb. 19, 2018. The entire contents of each of the aforementioned applications are incorporated herein by reference.

BACKGROUND OF THE INVENTION

Bruton tyrosine kinase (Btk) is a Tec family non-receptor protein kinase, expressed in most hematopoietic cells such as B cells, mast cells, and macrophages but not in T cells, natural killer cells, and plasma cells [Smith, C. I. et al. Journal of Immunology (1994), 152 (2), 557-65]. Btk is a crucial part of the BCR and FcR signaling pathway, and the targeted inhibition of Btk is a novel approach for treating many different human diseases such as B-cell malignancies, autoimmune disease, and inflammatory disorders [Uckun, Fatih M. et al, Anti-Cancer Agents in Medicinal Chemistry (2007), Shinohara et al, Cell 132 (2008) pp 794-806; Pan, Zhengying, Drug News & Perspectives (2008), 21 (7); 7 (6), 624-632; Gilfillan et al, Immunological Reviews 288 (2009) pp 149-169; Davis et al, Nature, 463 (2010) pp 88-94].

Covalent Bruton's tyrosine kinase (BTK) inhibitors including ibrutinib and acalabrutinib have transformed the treatment landscape of several BTK dependent B-cell malignancies, including chronic lymphocytic leukemia, Waldenstrom's macroglobulinemia, mantle cell lymphoma and marginal zone lymphoma. Despite impressive clinical response of ibrutinib in B-cell malignancies, cases of primary and secondary resistance have emerged with poor outcomes and limited treatment options. The majority of CLL patients who become resistant to irreversible BTK inhibitors such as ibrutinib develop the BTK-C481S mutation. It was reported that 80% of patients relapsing CLL will have the C481S mutation [Maddocks K J, et al. JAMA Oncol. 2015; 1:80-87]. Another research group in the Ohio State University reported in *Journal of Clinical Oncology* [Vol 35, number 13, 2017, page that at year four, roughly 20% of patients on ibrutinib clinically progressed. Of these patients who relapsed, 85% had acquired the C481S mutation. Additionally, these mutations were detected, on average, over nine months before a relapse.

Although BTK inhibitors such as Ibrutinib, and ACP-196, have made a significant contribution to the art, there is a strong need for continuing search in this field of art for highly potent and selective BTK inhibitors that can not only irreversibly inhibiting WT BTK but also reversibly inhibiting C481S mutant BTK.

SUMMARY OF THE INVENTION

The present invention relates to a class of potent and selective Btk inhibitors which are rationally designed to not only irreversibly inhibit the WT BTK but also reversibly inhibit the C481S mutant BTK. Thus, the compounds of the present invention may be useful in treating the patients resistant/refractory to the first generation BTK inhibitors such as Ibrutinib and ACP-196 (Acalabrutinib), particularly with BTK C481S mutation. The compounds of the present invention may be useful in treating the patients with diseases such as autoimmune disease, or inflammatory disorders.

In one aspect, this invention relates to a compound of Formula (I), or an N-oxide thereof, or a pharmaceutically acceptable salt, solvate, polymorph, tautomer, stereoisomer, an isotopic form, or a prodrug of said compound of Formula (I) or N-oxide thereof:

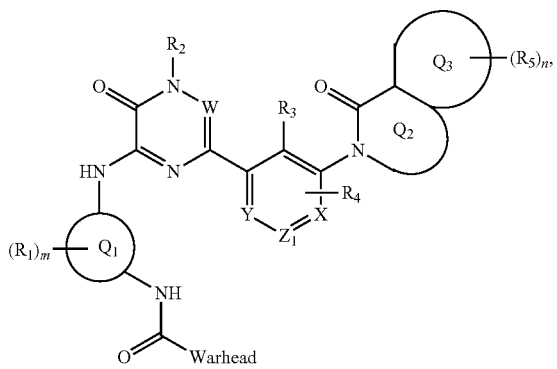

wherein
- $Q_1$ is a 5-6 membered aryl or heteroaryl;
- $Q_2$ is a 5-7 membered heterocycloalkyl, or heteroaryl;
- $Q_3$ is a 5-membered heteroaryl;
- each of W, X, Y, $Z_1$, independently, is $C(R_a)$, or N;
- each of $R_1$, and $R_5$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, $-P(O)R_bR_c$, -alkyl-$P(O)R_bR_c$, $-S(O)(=N(R_b))R_c$, $-N=S(O)R_bR_c$, $=NR_c$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;
- $R_2$ is H or alkyl;
- $R_3$ is H, halo, alkyl, haloalkyl, or hydroxyalkyl;
- $R_4$ is H, halo, or low alkyl;
- two of $R_1$ groups, taken together with the atom to which they are attached, may optionally form a cycloalkyl or heterocycloalkyl optionally substituted with one or more $R_d$;
- two of $R_5$ groups, taken together with the atom to which they are attached, may optionally form a cycloalkyl or heterocycloalkyl optionally substituted with one or more $R_d$;
- $R_a$, $R_b$, $R_c$ and $R_d$, independently, is H, D, alkyl, spiroalkyl, alkenyl, alkynyl, halo, cyano, amine, nitro, hydroxy, =O, $-P(O)R_bR_e$, -alkyl-$P(O)R_bR_c$, $-S(O)(=N(R_b))R_c$, $-N=S(O)R_bR_c$, $=NR_c$, $C(O)NHOH$, $C(O)OH$, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;
- $R_e$ is H, D, alkyl, spiroalkyl, alkenyl, alkynyl, halo, cyano, amine, nitro, hydroxy, =O, $C(O)NHOH$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

each of m, n, p, and q, independently, is 0, 1, 2, 3, or 4; and

Warhead is

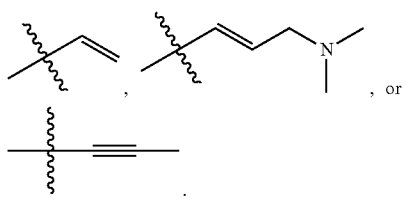
, or

In a preferred embodiments, the compound is represented by Formula (II):

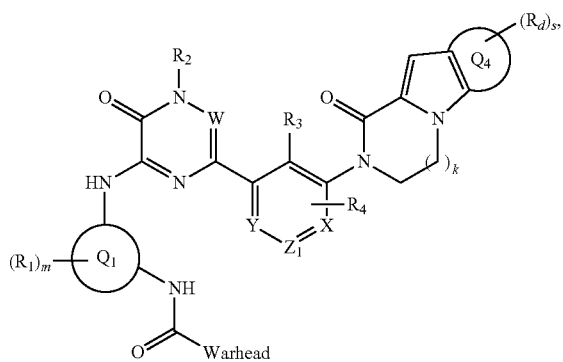

wherein
k is 0, 1, or 2;
s is 0, 1, 2, or 3; and
$Q_4$ is a 5-7 membered cycloalkyl, cycloalkenyl, heterocycloalkyl, or heterocycloalkenyl; and the remaining variables are as defined for Formula (I).

In a more preferred embodiment, the compound is represented by Formula (III)

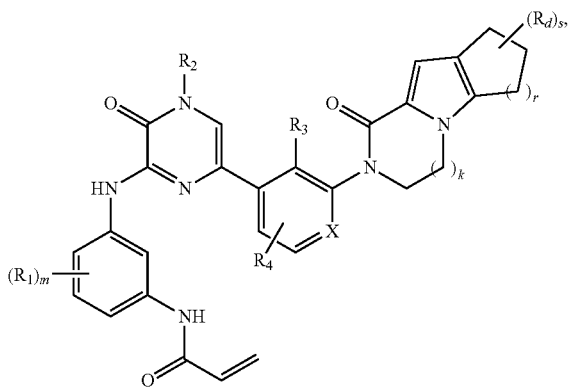

wherein
r is 0, 1, 2, or 3; and the remaining variables are as defined for Formula (I) or Formula (II).

In a more preferred embodiment, the compound is represented by Formula (IV):

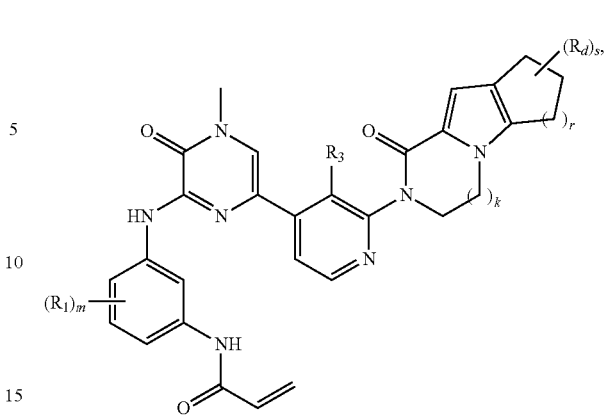

wherein
k is 1 or 2; and
r is 1, or 2; and the remaining variables are as defined for Formula (I) or Formula (II).

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a neoplastic disease, autoimmune disease, and inflammatory disorders, therapeutic uses thereof, and use of the compounds for the manufacture of a medicament for treating the disease/disorder.

This invention also relates to a method of treating a neoplastic disease, particularly the B-cell malignancy including but not limited to B-cell lymphoma, lymphoma (including Hodgkin's and non-Hodgkin's lymphoma), hairy cell lymphoma, small lymphocytic lymphoma (SLL), mantle cell lymphoma (MCL), and diffuse large B-cell lymphoma (DLBCL), multiple myeloma, chronic and acute myelogenous leukemia and chronic and acute lymphocytic leukemia, by administering to a subject in need thereof an effective amount of one or more of the compounds, modifications, and/or salts, and compositions thereof described above.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (E)-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)-4-(dimethylamino)but-2-enamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino)pyrrolidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl)phenyl)acrylamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(oxetan-3-yl)piperazin-1-yl)phenyl)acrylamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-(oxetan-3-yl)piperazin-1-yl)phenyl)acrylamide, (S)—N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(tetrahydro-2H-pyran-4-yl)piperazin-1-yl)phenyl)acrylamide, (S)—N-(2-(4-(4,4-difluorocyclohexyl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-4-(2,6-dimethyltetrahydro-2H-pyran-4-yl)-2-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-morpholinopiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(methyl(oxetan-3-yl)amino)piperidin-1-yl)phenyl)acrylamide, N-(2-((2'S)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(2-((2S)-4-(3,3-difluoropyrrolidin-1-yl)-2-methylpiperidin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-2-methyl-4-(4-methylpiperazin-1-yl)piperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-4-(dimethylamino)-2-methylpiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-(oxetan-3-yl)piperidin-4-yl)phenyl)acrylamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(1-(oxetan-3-yl)piperidin-4-yl)phenyl)acrylamide, N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-(4-methylpiperazin-1-yl)phenyl)acrylamide, N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-((4-methylpiperazin-1-yl)methyl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl)phenyl)but-2-ynamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-methylpiperazin-1-yl)phenyl)but-2-ynamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(oxetan-3-yl)piperazin-1-yl)phenyl)but-2-ynamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-(oxetan-3-yl)piperazin-1-yl)phenyl)but-2-ynamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)but-2-ynamide, (S)—N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(2-methyl-4-(oxetan-3-yl)piperazin-1-yl)phenyl)but-2-ynamide, (Z)-2-cyano-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)-4-methyl-4-(4-(oxetan-3-yl)piperazin-1-yl)pent-2-enamide, (Z)-2-cyano-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)-4-methyl-4-(4-methylpiperazin-1-yl)pent-2-enamide, (Z)-2-cyano-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)-4-methyl-4-(methyl(oxetan-3-yl)amino)pent-2-enamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(4-methylpiperazin-1-yl)propan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-morpholinopropan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(methyl(oxetan-3-yl)amino)propan-2-yl)phenyl)acrylamide, N-(2-(2-(4,4-difluoropiperidin-1-yl)propan-2-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(2-(2-(3,3-difluoropyrrolidin-1-yl)propan-2-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(4-(oxetan-3-yl)piperazin-1-yl)propan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-1-morpholinopropan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-1-(4-methylpiperazin-1-yl)propan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(piperidin-3-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-methylpiperazine-1-carbonyl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(tetrahydro-2H-pyran-4-yl)piperazin-1-yl)phenyl)acrylamide, (S)—N-(2-(4-(4,4-difluorocyclohexyl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-((2S)-2-methyl-4-morpholinopiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-morpholinopiperidin-1-yl)phenyl)acrylamide, N-(2-(4,4-difluoro-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(4-methylpiperazin-1-yl)piperidin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-fluoro-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexa-hydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-methyl-2-(2-methyl-4-(oxetan-3-yl) piperazin-1-yl)phenyl)acrylamide, (S)—N-(5-((6-(2-(7,7-dimethyl-1-oxo-1,3,4,6,7,8-hexa-hydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)-3-(trifluoromethyl)phenyl)acrylamide, (S)—N-(3-cyano-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydro-pyrazin-2-yl)amino)-2-(2-methyl-4-(oxetan-3-yl) piperazin-1-yl)phenyl)acrylamide, (S)—N-(5-((6-(2-(7,7-dimethyl-1-oxo-1,3,4,6,7,8-hexa-hydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-(isopropylsulfonyl)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexa-hydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)-3-((trifluoromethyl)sulfonyl)phenyl)acrylamide, N-(2-((2'S)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)-2-((2S)-2-methyl-4-(4-methylpiperazin-1-yl) piperidin-1-yl)phenyl)acrylamide.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery,* 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcar-bonochloridate, para-nitrophenyl carbonate, or the like) or an acylating agent. Further examples of methods and strategies of making prodrugs are described in *Bioorganic and Medicinal Chemistry Letters,* 1994, Vol. 4, p. 1985.

Deuterium-enriched compounds: deuterium (D or $^2H$) is a stable, non-radioactive isotope of hydrogen and has an atomic weight of 2.0144. Hydrogen naturally occurs as a mixture of the isotopes $^1H$ (hydrogen or protium), D ($^2H$ or deuterium), and T (3H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as $(C_{1-4})$ alkyl halides, e.g., methyl, ethyl, iso-propyl and tert-butyl chlorides, bromides and iodides; di-$(C_{1-4})$ alkyl sulfates, e.g., dimethyl, diethyl and diamyl sulfates; alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention.

Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl.

Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NR$_a$R$_b$ where R$_a$ and R$_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —NO$_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%.

However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), *Vinca* alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFR$_b$, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (pp110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1(M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDGFRa(D842V), PDGFRa(T674I), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors(HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), drug-antibody conjugate (e.g brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, antimetabolites, topoisomerase inhibitors, anti-microtubule agents, kinase inhibitors, epigenetic agents, HSP90 inhibitors, PARP inhibitors, BCL-2 inhibitor, drug-antibody conjugate, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

In certain embodiments, the compounds of the invention are administered in combination with one or more anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate. Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates. The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

In certain embodiments, the compounds of the invention are administered in combination with one or more immunosuppressant agents.

In some embodiments, the immunosuppressant agent is glucocorticoid, methotrexate, cyclophosphamide, azathioprine, mercaptopurine, leflunomide, cyclosporine, tacrolimus, and mycophenolate mofetil, dactinomycin, anthracyclines, mitomycin C, bleomycin, or mithramycin, or fingolimod.

The invention further provides methods for the prevention or treatment of a neoplastic disease, autoimmune and/or inflammatory disease. In one embodiment, the invention relates to a method of treating a neoplastic disease, autoimmune and/or inflammatory disease in a subject in need of treatment comprising administering to said subject a therapeutically effective amount of a compound of the invention. In one embodiment, the invention further provides for the use of a compound of the invention in the manufacture of a medicament for halting or decreasing a neoplastic disease, autoimmune and/or inflammatory disease.

In one embodiment, the neoplastic disease is a B-cell malignancy includes but not limited to B-cell lymphoma, lymphoma (including Hodgkin's lymphoma and non-Hodgkin's lymphoma), hairy cell lymphoma, small lymphocytic lymphoma (SLL), mantle cell lymphoma (MCL), and diffuse large B-cell lymphoma (DLBCL), multiple myeloma, chronic and acute myelogenous leukemia and chronic and acute lymphocytic leukemia.

The autoimmune and/or inflammatory diseases that can be affected using compounds and compositions according to the invention include, but are not limited to allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barre syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

In scheme A, the reactant 5 can be prepared by the reaction of 3,5-dibromo-1-methylpyrazin-2(1H)-one with appropriate aniline. The nitro group in the reactant 5 can be other group such as a protected amine group, or —NHC(O)—Warhead.

The typical starting material

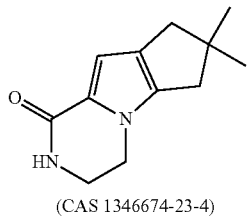

(CAS 1346674-23-4)

is commercially available. However, the reported route, e.g. in WO 2013067274, to this intermediate entails at least 7 synthetic steps. The synthesis not only is long, it also includes several reagents and solvents that are toxic or hazardous and present environmental liabilities. We describe herein in Scheme 1 a new, more efficient, and cost-effective route (three synthetic steps) focused on the use of sustainable chemistry:

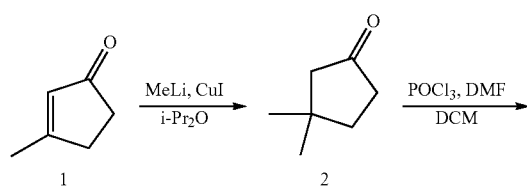

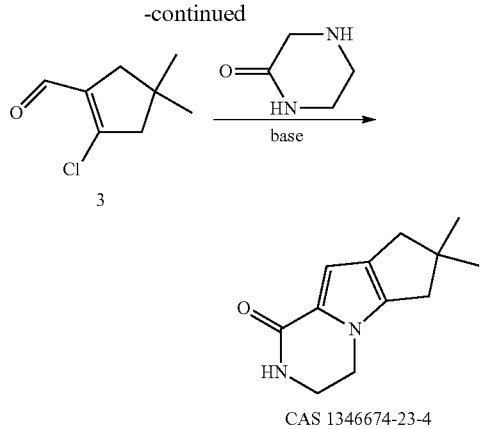

In Scheme 1, the starting material 3-methylcyclopent-2-en-1-one was converted to 3,3-dimethylcyclopentan-1-one by standard organic reaction with high yield, which can further be converted to intermediate 3. Finally, intermediate 3 can react with piperazin-2-one to yield the target molecule of CAS 1346674-23-4.

The intermediate

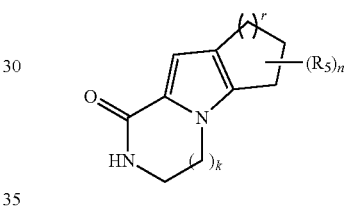

can be made by the method similar to Scheme 1, by using different starting material and reagents.

The intermediate

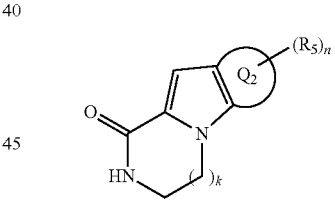

can be made by the method similar to Scheme 1, by using different starting material and reagents, or by the standard organic reactions.

The intermediate

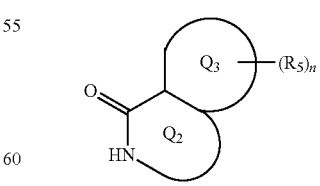

can be made by the method similar to Scheme 1 by using different starting material and reagents, or by the standard organic reactions.

A typical approach to synthesize the Formula (IV) compounds

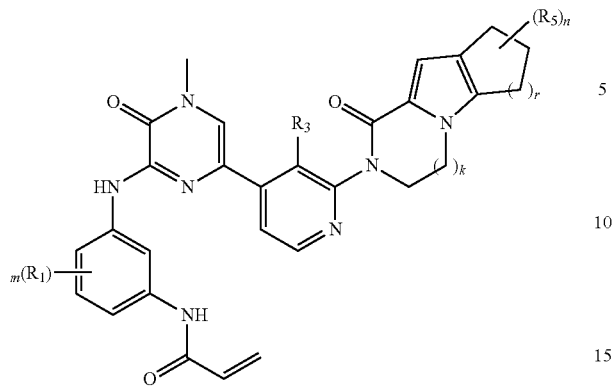
in which $R_3$ is —$CH_2OH$ is described in Scheme A. $R_1$, $R_4$, X, Warhead, and m in general Scheme A are the same as those described in the Summary section above.
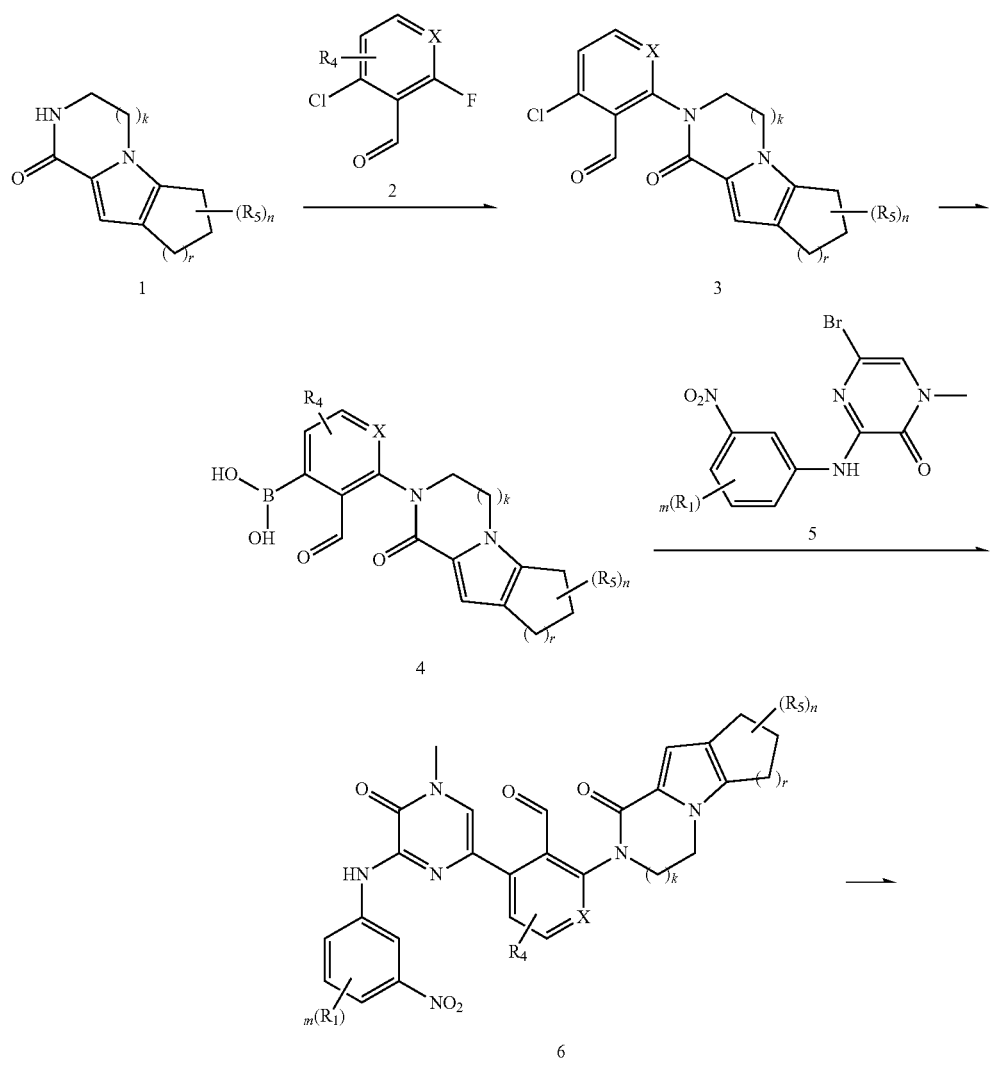

-continued

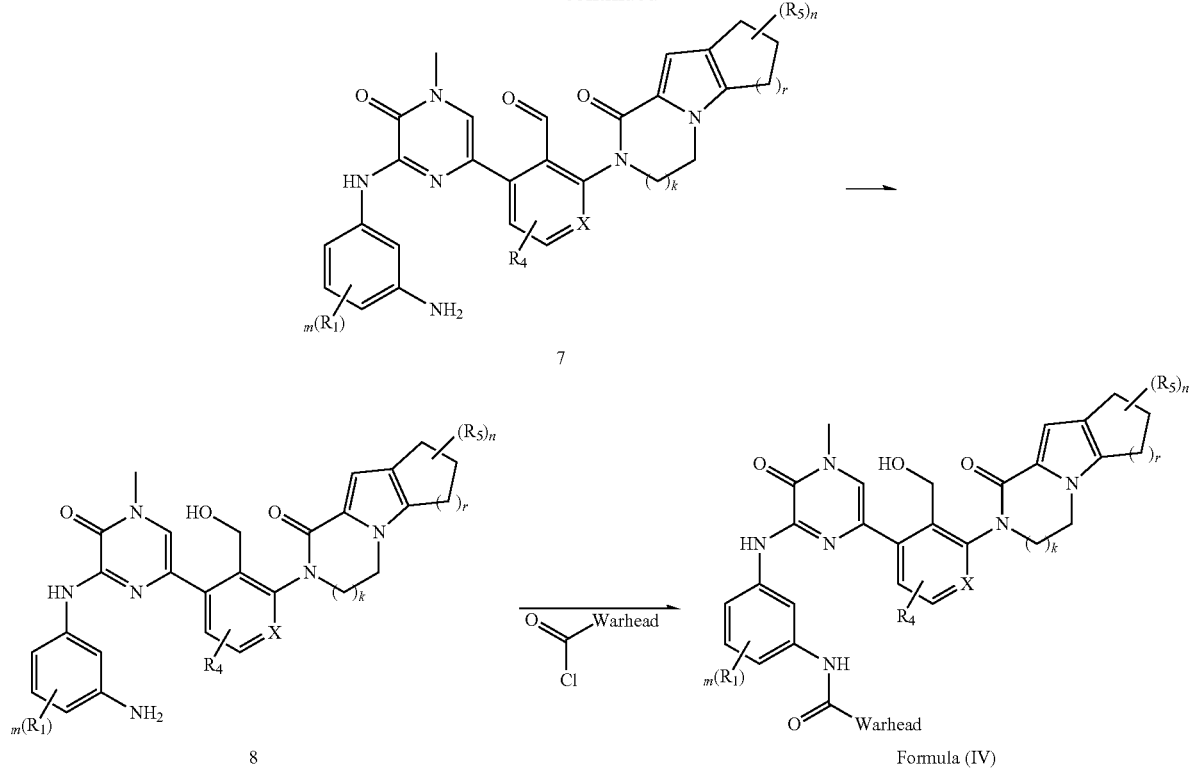

7

8

Formula (IV)

In Scheme A, the appropriate starting material 1 can react with 2 to form the intermediate 3, which can be converted to 4 by standard organic reaction with high yield. Meanwhile, the intermediate 5 can be obtained by the reaction of the commercially available 3,5-dibromo-1-methylpyrazin-2 (1H)-one (CAS 87486-34-8) with appropriate 4-substituted 3-nitroaniline. Then, the coupling reaction of 4 with 5 will yield the nitro intermediate 6, which can be reduced to the amine intermediate 7. Finally, 7 can be reduced to the alcohol intermediate 8, which can react appropriate acryloyl chloride to afford Formula (IV).

The Formula (III) compounds

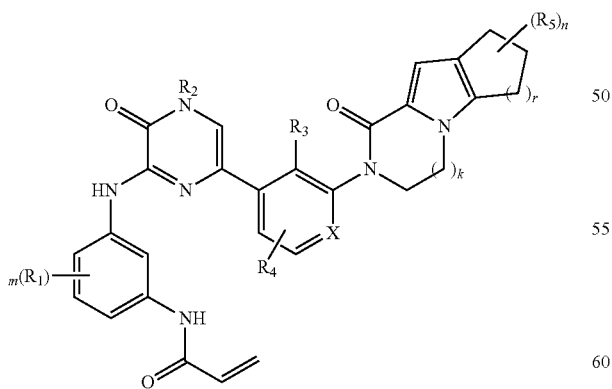

can be made by the method similar to Scheme A, by using different starting material and reagents.

The Formula (II) compounds

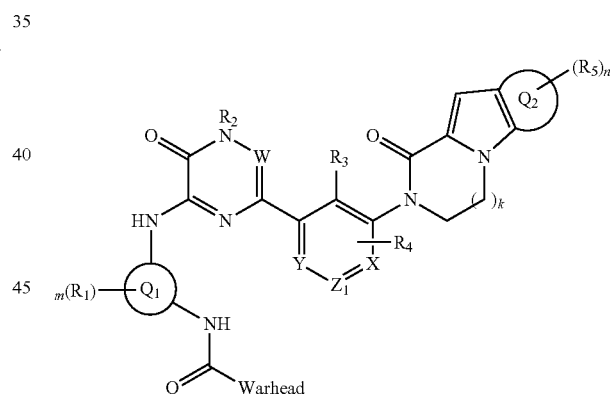

can be made by the method similar to Scheme A, by using different starting material and reagents.

The Formula (I) compounds

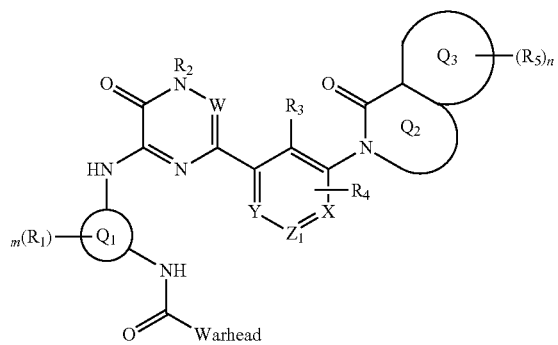

can be made by the method similar to Scheme A, by using different starting material and reagents.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example 1: Preparation of 7,7-dimethyl-3,4,7,8-tetrahydro-2H-cyclopenta[4,5]pyrrolo[1,2-a]pyrazin-1(6H)-one Into a 1000-mL round-bottom flask purged and maintained with an inert atmosphere of nitrogen, was placed a solution of CuI (47.6 g, 249.93 mmol, 1.20 equiv) in ether (500 mL). To the solution was added MeLi (286 mL/2M, 2.20 equiv) at 0° C. and the mixture was stirred at the same temperature for 2 hours. To the solution was added 3-methylcyclopent-2-en-1-one (20 g, 208.06 mmol, 1.00 equiv) at the same temperature. The resulting solution was stirred for 2 h at 0° C. in a water/ice bath. The reaction was then quenched by the addition of 500 mL of NH$_4$Cl (aq.), when TLC showed that SM have vanished (PE:EA=1:1). The resulting solution was extracted with 3×200 ml of ether and the organic layers combined and dried over anhydrous sodium sulfate and concentrated under vacuum. This resulted in 21 g (90%) of 3,3-dimethylcyclopentan-1-one as colorless oil.

Into a 500-mL round-bottom flask purged and maintained with an inert atmosphere of nitrogen, was placed a solution of N,N-dimethylformamide (41.6 g, 569.16 mmol, 3.00 equiv) in dichloromethane (200 mL). To the solution was added POCl$_3$ (57.3 g, 373.70 mmol, 2.00 equiv) at 0° C. and then the reaction mixture was stirred at room temperature for 1.5 hour. To the solution was added 3,3-dimethylcyclopentan-1-one (21.0 g, 187.22 mmol, 1.00 equiv) at the same temperature. The resulting solution was stirred overnight at 55° C. in an oil bath. The reaction was then quenched by the addition of 200 mL of aqueous NaAcO when TLC showed that the reaction have been finished (PE:EA=1:1). The resulting solution was extracted with 3×200 of dichloromethane and the organic layers combined and dried over anhydrous sodium sulfate and concentrated under vacuum. This resulted in 30 g (crude) of 2-chloro-4,4-dimethylcyclopent-1-ene-1-carbaldehyde as brown oil.

Into a 250-mL round-bottom flask purged and maintained with an inert atmosphere of nitrogen, was placed a solution of piperazin-2-one (18.7 g, 186.78 mmol, 1.00 equiv) and DIEA (24.2 g, 187.25 mmol, 1.00 equiv) in NMP (45 mL) and then to the solution was added 2-chloro-4,4-dimethyl-cyclopent-1-ene-1-carbaldehyde (29.7 g, 187.23 mmol, 1.00 equiv) at 100° C. dropwise. The resulting solution was stirred for 30 min at 100° C. in an oil bath. The reaction was then quenched by the addition of 200 mL of water when TLC showed that the reaction have been finished (EA). The solids were collected by filtration. This resulted in 20 g (52%) of 4,4-dimethyl-1,10-diazatricyclo[6.4.0.0ˆ[2,6]]dodeca-2(6),7-dien-9-one as a off-white solid. LC-MS: (ES, m/z): 205[M+H]$^+$. $^1$H-NMR: (300 MHz, d$_6$-DMSO, ppm): δ7.38 (s, 1H), 6.36 (s, 1H), 3.92 (t, J=5.9 Hz, 2H), 3.45 (m, 2H), 2.50 (s, 2H), 2.38 (s, 2H), 1.19 (s, 6H).

Example 2: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl)phenyl) acrylamide A mixture of 4-fluoro-3-nitroaniline (100 g, 0.64 mol), and N-methylpiperazine (256 g, 2.56 mol) are dissolved in ethanol, The mixture was maintained at reflux for 24 h, and then the mixture was allowed to cool to room temperature, the reaction was concentrated in vacuum and filtered to give 4-(4-methylpiperazin-1-yl)-3-nitroaniline as a red solid (131 g, 86%) 1H-NMR (300 MHZ, CDCl$_3$) 7.11 (d, 1H), 7.02 (d, 1H), 6.807-6.845 (m, 1H), 3.76 (s, 2H), 2.98 (m, 4H), 2.557 (m, 4H), 2.35 (s, 3H).

A mixture of 4-(4-methylpiperazin-1-yl)-3-nitroaniline (14.53 g, 0.0615 mol), 3,5-dibromo-1-methylpyrazin-2(1H)-one (16.5 g, 0.0615 mol) cesium carbonate (40.1 g, 0.123 mol), DMF (14 ml) and 1,4-dioxane (200 ml), after bubbling nitrogen through the resulting suspension for 30 min, Xantphons (3.5 g, 0.00615 mol) and tris(dibenzylideneacetone) dipalladium(0) (6.3 g, 0.00615 mol) were added. And the reaction mixture was heated at 100° C. for 2 h, after this time, the mixture was cooled to room temperature and diluted with 90:10 methylene chloride/methanol (500 ml) and water (300 ml), and the layers were separated, the aqueous layers were extracted with 90:10 methylene chloride/methanol (500 ml), and the combined organic layers were washed with brine and dried over sodium sulfate. The drying agent was removed by filtration, the filtrate was concentrated under reduced pressure, and the resulting residue was purified by flash column chromatography (90:10 methylene chloride/methanol) to afford D (12 g, 46%) 1H-NMR (300 MHZ, CDCl$_3$), 8.31 (d, 2H), 7.85 (m, 1H), 7.23 (d, 1H), 6.82 (s, 1H), 3.55 (s, 3H), 3.08 (m, 4H), 2.59 (m, 4H), 2.38 (s, 3H).

A mixture of the commerically available starting material 4-chloro-2-(7,7-dimethyl-1-oxo-1,3,4,6,7,8-hexahydro-2H-cyclopenta[4,5]pyrrolo[1,2-a]pyrazin-2-yl)nicotinaldehyde (CAS #1434050-55-1, 1.5 g, 4.37 mmol, 1.0 eq), Pin$_2$B$_2$ (2.8 g, 11 mmol, 2.5 eq), Pd(dppf)Cl$_2$ (356 mg, 0.44 mmol, 0.1 eq) and KOAc (1.3 g, 13 moml, 3.0 eq) in 1, 4-dioxane (150 mL) was refluxed for 4 h under N$_2$ atmosphere. The mixture was cooled to rt and filtered. The filtrate was concentrated to give (2-(7,7-dimethyl-1-oxo-1,3,4,6,7,8-hexahydro-2H-cyclopenta[4,5]pyrrolo[1,2-a]pyrazin-2-yl)-3-formylpyridin-4-yl)boronic acid (3.0 g) as brown oil which was used to the next step without further purification. ESI-MS (M+H)$^+$: 354.2.

A mixture of (2-(7,7-dimethyl-1-oxo-1,3,4,6,7,8-hexahydro-2H-cyclopenta[4,5]pyrrolo[1,2-a]pyrazin-2-yl)-3-formylpyridin-4-yl)boronic acid (crude from previous step, 4.37 mmol, 1.0 eq), 5-bromo-1-methyl-3-((4-(4-methylpiperazin-1-yl)-3-nitrophenyl)amino)pyrazin-2(1H)-one (Example 1, 900 mg, 2.2 mmol, 0.5 eq), Pd(dppf)Cl$_2$ (360 mg, 0.44 mmol, 0.1 eq) and K$_2$CO$_3$ (1.5 g, 13 moml, 3.0 eq) in dioxane (50 mL) and H$_2$O (5 mL) was stirred at 90° C. for 4 h under N$_2$ atmosphere. The mixture was cooled to rt and concentrated and the residue was purified by column chromatography on silica gel (DCM:MeOH=30:1) to give 2-(7,7-dimethyl-1-oxo-1,3,4,6,7,8-hexahydro-2H-cyclopenta[4,5]pyrrolo[1,2-a]pyrazin-2-yl)-4-(4-methyl-6-((4-(4-methylpiperazin-1-yl)-3-nitrophenyl)amino)-5-oxo-4,5-dihydropyrazin-2-yl)nicotinaldehyde as brown solid (600 mg, two step Y: 40%). ESI-MS (M+H)$^+$: 652.1.

A mixture of 2-(7,7-dimethyl-1-oxo-1,3,4,6,7,8-hexahydro-2H-cyclopenta[4,5]pyrrolo[1,2-a]pyrazin-2-yl)-4-(4-methyl-6-((4-(4-methylpiperazin-1-yl)-3-nitrophenyl)amino)-5-oxo-4,5-dihydropyrazin-2-yl)nicotinaldehyde (600 mg, 0.92 mmol, 1.0 eq) and Pd/C (120 mg, 20% wt) in MeOH (20 mL) was hydrogenated at rt for 16 h under one atmosphere of H$_2$ pressure. The catalyst was filtered off through a Celite pad and the filtrate was concentrated to give 4-(6-((3-amino-4-(4-methylpiperazin-1-yl)phenyl)amino)-4-methyl-5-oxo-4,5-dihydropyrazin-2-yl)-2-(7,7-dimethyl-1-oxo-1,3,4,6,7,8-hexahydro-2H-cyclopenta[4,5]pyrrolo[1,2-a]pyrazin-2-yl)nicotinaldehyde as brown solid (600 mg). ESI-MS (M+H)$^+$: 622.1.

To a solution of 4-(6-((3-amino-4-(4-methylpiperazin-1-yl)phenyl)amino)-4-methyl-5-oxo-4,5-dihydropyrazin-2-yl)-2-(7,7-dimethyl-1-oxo-1,3,4,6,7,8-hexahydro-2H-cyclopenta[4,5]pyrrolo[1,2-a]pyrazin-2-yl)nicotinaldehyde (crude from previous step, 0.92 mmol, 1.0 eq) in MeOH (10 mL) was added a solution of NaBH$_4$ (70 mg, 1.8 mmol, 2.0 eq) in MeOH (10 mL) at 0° C. The solution was stirred at rt for 16 h. Concentrated and the residue was purified by Pre-HPLC (A: H$_2$O, 0.05% NH$_3$·H$_2$O, B: MeCN) to give 2-(4-(6-((3-amino-4-(4-methylpiperazin-1-yl)phenyl)amino)-4-methyl-5-oxo-4,5-dihydropyrazin-2-yl)-3-(hydroxymethyl)pyridin-2-yl)-7,7-dimethyl-3,4,7,8-tetrahydro-2H-cyclopenta[4,5]pyrrolo[1,2-a]pyrazin-1(6H)-one as a brown solid (150 mg, two step Y: 56%). ESI-MS (M+H)$^+$: 624.1

To a mixture of 2-(4-(6-((3-amino-4-(4-methylpiperazin-1-yl)phenyl)amino)-4-methyl-5-oxo-4,5-dihydropyrazin-2-yl)-3-(hydroxymethyl)pyridin-2-yl)-7,7-dimethyl-3,4,7,8-tetrahydro-2H-cyclopenta[4,5]pyrrolo[1,2-a]pyrazin-1(6H)-one (150 mg, 0.24 mmol, 1.0 eq), acrylic acid (26 mg, 0.36 mmol, 1.5 eq) and HATU (123 mg, 0.36 mmol, 1.5 eq) in DMF (5 mL) was added TEA (73 mg, 0.72 mmol, 3.0 eq). The mixture was stirred for 4 h at rt. The reaction mixture was purified by Pre-HPLC (A: H$_2$O, 0.05% NH$_3$·H$_2$O; B: MeCN) to give N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl)phenyl)acrylamide as a brown solid (38 mg, Y: 23%). ESI-MS (M+H)$^+$: 678.1. $^1$H NMR (400 MHz, DMSO-d$_6$) δ: 9.24 (s, 1H), 9.06 (s, 1H), 8.88 (s, 1H), 8.46 (d, J=5.2 Hz, 1H), 7.88 (d, J=4.8 Hz, 1H), 7.75 (s, 1H), 7.63 (dd, J=2.0 Hz, 4.4 Hz, 1H), 7.12 (d, J=8.4 Hz, 1H), 6.66-6.56 (m, 1H), 6.57 (s, 1H), 6.33-6.28 (m, 1H), 5.79-5.76 (m, 1H), 5.04 (br s, 1H), 4.60-4.46 (m, 2H), 4.26-4.18 (m, 3H), 3.86-3.83 (m, 1H), 3.55 (s, 3H), 2.79-2.75 (m, 4H), 2.67-2.57 (m, 6H), 2.43 (s, 2H), 2.24 (s, 3H), 1.22 (s, 6H).

Example 3: Preparation of (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide Into a 1000-mL round-bottom flask purged and maintained with an inert atmosphere of nitrogen, was placed 4-fluoro-3-nitroaniline (50 g, 320.28 mmol, 1.00 equiv), CH$_3$CN (500 mL), NMM (64.7 g, 639.64 mmol, 2.00 equiv), Cbz-Cl (87.4 g, 512.34 mmol, 1.60 equiv). The resulting solution was stirred overnight at room temperature. The resulting mixture was concentrated under vacuum. The residue was applied onto a silica gel column with ethyl acetate/petroleum ether (1:1). This resulted in 45 g (48%) of benzyl N-(4-fluoro-3-nitrophenyl)carbamate as a yellow solid. LC-MS: (ES, m/z): [M+H]$^+$=291, $^1$H-NMR: (300 MHz, CDCl$_3$, ppm): δ8.15 (m, 1H), 7.65 (m, 1H), 7.42-7.32 (m, 5H), 7.22 (m, 1H), 6.80 (s, 2H), 5.22 (s, 2H).

Into a 250-mL round-bottom flask purged and maintained with an inert atmosphere of nitrogen, was placed a solution of benzyl N-(4-fluoro-3-nitrophenyl)carbamate (10 g, 34.45 mmol, 1.00 equiv) in DMSO (100 mL), tert-butyl (3S)-3-methylpiperazine-1-carboxylate (7.58 g, 37.85 mmol), DIEA (6.67 g, 51.61 mmol, 1.50 equiv). The resulting solution was stirred overnight at 110° C. in an oil bath. The resulting solution was diluted with of water. The resulting solution was extracted with of ethyl acetate and the organic layers combined and concentrated under vacuum. The residue was applied onto a silica gel column with ethyl acetate/petroleum ether (1:1). This resulted in 10 g (62%) of tert-butyl (3S)-4-(4-[[(benzyloxy)carbonyl]amino]-2-nitrophenyl)-3-methylpiperazine-1-carboxylate as brown oil. LC-MS: (ES, m/z): [M+H]$^+$=471. $^1$H-NMR (300 MHz, CDCl$_3$, ppm): δ7.86 (s, 1H), 7.60 (m, 1H), 7.44-7.31 (m, 7H), 5.21 (s, 2H), 3.90 (t, J=11.4 Hz, 2H), 3.21-3.02 (m, 3H), 2.79-2.72 (m, 2H), 1.49 (s, 9H), 0.80 (d, J=6.3 Hz, 3H).

Into a 250-mL round-bottom flask purged and maintained with an inert atmosphere of nitrogen, was placed a solution of tert-butyl (3S)-4-(4-[[(benzyloxy)carbonyl]amino]-2-nitrophenyl)-3-methylpiperazine-1-carboxylate (12.5 g, 26.57 mmol, 1.00 equiv) in dioxane (100 mL), hydrogen chloride dioxane (25 mL). The resulting solution was stirred for 30 min at room temperature. The resulting mixture was concentrated under vacuum. This resulted in 12.5 g (crude) of benzyl N-[4-[(2S)-2-methylpiperazin-1-yl]-3-nitrophenyl]carbamate as brown oil. LC-MS: (ES, m/z): 371[M+H]$^+$.

Into a 250-mL round-bottom flask purged and maintained with an inert atmosphere of nitrogen, was placed a solution of benzyl N-[4-[(2S)-2-methylpiperazin-1-yl]-3-nitrophenyl]carbamate (12.5 g, 33.75 mmol, 1.00 equiv) in ethanol (100 ml), oxetan-3-one (2.2 g, 30.53 mmol, 1.20 equiv), NaBH$_3$CN (1.67 g, 26.58 mmol, 1.00 equiv). The resulting solution was stirred for 2 h at room temperature. The resulting mixture was concentrated under vacuum. The residue was applied onto a silica gel column with ethyl acetate/petroleum ether (1:1). This resulted in 5 g (35%) of benzyl N-[4-[(2S)-2-methyl-4-(oxetan-3-yl)piperazin-1-yl]-3-nitrophenyl]carbamate as brown oil. LC-MS: (ES, m/z): 427[M+H]$^+$ $^1$H-NMR (300 MHz, CD$_3$OD, ppm): δ7.86 (s, 1H), 7.60 (m, 1H), 7.48-7.31 (m, 6H), 5.21 (s, 2H), 4.75-4.55 (m, 5H), 3.55 (m, 1H), 3.26-3.10 (m, 2H), 2.97-2.72 (m, 3H), 2.30-2.11 (m, 3H), 1.80 (t, J=4.7 Hz, 1H), 1.49 (s, 9H), 0.80 (d, J=6.3 Hz, 3H).

Into a 100-mL round-bottom flask purged and maintained with an inert atmosphere of nitrogen, was placed a solution of benzyl N-[4-[(2S)-2-methyl-4-(oxetan-3-yl)piperazin-1-yl]-3-nitrophenyl]carbamate (5.0 g, 11.72 mmol, 1.00 equiv) in ethanol (50 ml), AcOH (7.0 g, 116.57 mmol, 10.00 equiv). This was followed by the addition of dust Zn (4.6 g, 6.00 equiv). The resulting solution was stirred for 1 h at room temperature. The solids were filtrated out. The resulting mixture was concentrated under vacuum and applied on a silica gel column. This resulted in 1.0 g (22%) of benzyl N-[3-amino-4-[(2S)-2-methyl-4-(oxetan-3-yl)piperazin-1-yl]phenyl]carbamate as brown oil. LC-MS: (ES, m/z): 397 [M+H]$^+$. $^1$H-NMR (300 MHz, CD$_3$OD, ppm): δ7.46-7.31 (m, 5H), 7.02 (m, 2H), 6.75 (d, J=8.4, 1H), 5.20 (s, 2H), 4.85-4.64 (m, 4H), 3.67-3.55 (m, 3H), 3.17 (m, 1H), 2.92-2.78 (m, 4H), 2.25 (m, 1H), 1.95 (m, 1H), 0.80 (d, J=6.0 Hz, 3H).

Into a 25-mL round-bottom flask purged and maintained with an inert atmosphere of nitrogen, was placed a solution of benzyl N-[3-amino-4-[(2S)-2-methyl-4-(oxetan-3-yl)piperazin-1-yl]phenyl]carbamate (1.0 g, 2.52 mmol, 1.00 equiv) in tetrahydrofuran (10 mL), NMM (510 mg, 5.04 mmol, 2.00 equiv), (Boc)$_2$O (820 mg, 3.76 mmol, 1.50 equiv). The resulting solution was stirred overnight at room temperature. The resulting mixture was concentrated under vacuum. The residue was applied onto a silica gel column with ethyl acetate/petroleum ether (1:1). This resulted in 0.9 g (72%) of benzyl N-(3-[[(tert-butoxy)carbonyl]amino]-4-[(2S)-2-methyl-4-(oxetan-3-yl)piperazin-1-yl]phenyl)carbamate as brown oil. LC-MS: (ES, m/z): 497[M+H]$^+$.

Into a 50-mL round-bottom flask purged and maintained with an inert atmosphere of H$_2$, was placed a solution of benzyl N-(3-[[(tert-butoxy)carbonyl]amino]-4-[(2S)-2-methyl-4-(oxetan-3-yl)piperazin-1-yl]phenyl)carbamate (900 mg, 1.81 mmol, 1.00 equiv) in methanol (10 mL), Palladium carbon (0.1 g, 0.10 equiv). The resulting solution was stirred for 1 h at room temperature. The solids were filtered out. The resulting mixture was concentrated under vacuum. This resulted in 0.6 g (91%) of tert-butyl N-[5-amino-2-[(2S)-2-methyl-4-(oxetan-3-yl)piperazin-1-yl]phenyl]carbamate as brown oil. LC-MS: (ES, m/z): 363[M+H]$^+$ $_1$H-NMR-PH-: (300 MHz, CD$_3$OD, ppm): δ7.46-7.31 (m, 5H), 7.02 (m, 2H), 6.75 (d, J=8.4, 1H), 4.78-4.64 (m, 4H), 3.60 (m, 1H), 3.10-2.70 (m, 5H), 2.22 (m, 1H), 1.95 (m, 1H), 0.77 (d, J=6.0 Hz, 3H).

Into a 50-mL round-bottom flask purged and maintained with an inert atmosphere of nitrogen, was placed a solution of tert-butyl N-[5-amino-2-[(2S)-2-methyl-4-(oxetan-3-yl)piperazin-1-yl]phenyl]carbamate (1.2 g, 3.31 mmol, 1.00 equiv) in IPA (10 mL), 3,5-dibromo-1-methyl-1,2-dihydropyrazin-2-one (980 mg, 3.66 mmol, 1.00 equiv), DIEA (640 mg, 4.95 mmol, 1.50 equiv). The resulting solution was stirred overnight at 80° C. in an oil bath. The resulting mixture was concentrated under vacuum. The residue was applied onto a silica gel column with ethyl acetate/petroleum ether (1:1). This resulted in 1.2 g (66%) of tert-butyl N-[5-[(6-bromo-4-methyl-3-oxo-3,4-dihydropyrazin-2-yl)amino]-2-[(2S)-2-methyl-4-(oxetan-3-yl)piperazin-1-yl]phenyl]carbamate as brown oil. LC-MS: (ES, m/z): 551[M+H]$^+$ $^1$H-NMR: (300 MHz, CDCl$_3$, ppm): δ8.31 (s, 1H), 8.20 (s, 1H), 7.99 (s, 1H), 7.20 (d, J=8.7, 1H), 6.95 (d, J=8.7, 1H), 6.75 (s, 1H), 4.78-4.64 (m, 5H), 3.60 (m, 1H), 3.20-2.72 (m, 7H), 2.22 (m, 1H), 1.95 (m, 1H), 0.79 (d, J=6.0 Hz, 3H).

Into a 50-mL round-bottom flask purged and maintained with an inert atmosphere of nitrogen, was placed a solution of tert-butyl N-[5-[(6-bromo-4-methyl-3-oxo-3,4-dihydropyrazin-2-yl)amino]-2-[(2S)-2-methyl-4-(oxetan-3-yl)piperazin-1-yl]phenyl]carbamate (600 mg, 1.09 mmol, 1.00 equiv) in dichloromethane (6 ml), trifluoroacetic acid (1.2 mL). The resulting solution was stirred for 1 h at room temperature. The resulting mixture was concentrated under vacuum. This resulted in 500 mg (crude) of 3-([3-amino-4-[(2S)-2-methyl-4-(oxetan-3-yl)piperazin-1-yl]phenyl]amino)-5-bromo-1-methyl-1,2-dihydropyrazin-2-one as brown oil. LC-MS: (ES, m/z): 451[M+H]$^+$.

Into a 25-mL round-bottom flask purged and maintained with an inert atmosphere of nitrogen, was placed a solution of 3-([3-amino-4-[(2S)-2-methyl-4-(oxetan-3-yl)piperazin-1-yl]phenyl]amino)-5-bromo-1-methyl-1,2-dihydropyrazin-2-one (500 mg, 1.11 mmol, 1.00 equiv) in dioxane (15 mL)/H$_2$O (1 mL), (2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)boronic acid (431 mg, 0.98 mmol, 1.10 equiv), Pd(dppf)Cl$_2$ (50 mg, 0.07 mmol, 0.10 equiv), potassium carbonate (307 mg, 2.22 mmol, 2.00 equiv). The resulting solution was stirred for 1 h at 100° C. in an oil bath. The resulting mixture was concentrated under vacuum, dilute with H$_2$O and extract With EA. This resulted in 500 mg (59%) of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one (crude) as brown oil. LC-MS: (ES, m/z): 764[M+H]$^+$.

Into a 50-mL round-bottom flask purged and maintained with an inert atmosphere of nitrogen, was placed a solution of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one (500 mg, 0.65 mmol, 1.00 equiv) in dichloromethane (5 mL), trifluoroacetic acid (1 mL). The resulting solution was stirred for 15 min at 40° C. in an oil bath. The resulting mixture was concentrated under vacuum. The crude product was purified by Prep-HPLC. This resulted in 80 mg (18%) of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one as a brown solid. LC-MS: (ES, m/z): 680[M+H]$^+$.

Into a 25-mL round-bottom flask purged and maintained with an inert atmosphere of nitrogen, was placed a solution of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one (80 mg, 0.12 mmol, 1.00 equiv) in CH$_3$CN (1 mL), prop-2-enoic acid (10 mg, 0.14 mmol, 1.20 equiv), HATU (49.2 mg, 0.13 mmol, 1.10 equiv), NMM (17.7 mg, 0.17 mmol, 1.50 equiv). The resulting solution was stirred for 1 h at room temperature. The crude product was purified by Prep-HPLC. This resulted in 27 mg (31%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-2-[(2S)-2-methyl-4-(oxetan-3-yl)piperazin-1-yl]phenyl)prop-2-enamide as a off-white solid. LC-MS: (ES, m/z): 734[M+H]$^+$. $^1$H-NMR: (300 MHz, d$_6$-DMSO, ppm): δ9.25 (s, 1H), 9.19 (s, 1H), 9.11 (s, 1H), 8.49 (d, J=5.1 Hz, 1H), 7.95 (d, J=5.1 Hz, 1H), 7.77 (s, 1H), 7.60 (d, J=8.7, 1H), 7.25 (d, J=8.7, 1H), 6.63-6.57 (m, 2H), 6.30 (m, 1H), 5.80 (d, J=3.9 Hz, 1H), 5.02 (m, 1H), 4.65-4.41 (m, 6H), 4.35-4.15 (m, 3H), 3.85 (m, 1H), 3.60-3.43 (m, 4H), 3.10 (m, 1H), 2.85-2.54 (m, 6H), 2.45 (m, 2H), 2.22 (m, 1H), 1.95 (t, J=6.6 Hz, 1H), 1.25 (s, 6H), 0.76 (d, J=6.0 Hz, 3H).

Example 4: Preparation of (S)—N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(2-methyl-4-(oxetan-3-yl)piperazin-1-yl)phenyl)acrylamide Into a 50-mL round-bottom flask purged and maintained with an inert atmosphere of nitrogen, was placed a solution of 4,4-dimethyl-1,10-diazatricyclo[6.4.0.0^[2,6]]dodeca-2 (6),7-dien-9-one (3.0 g, 14.69 mmol, 1.00 equiv) in dioxane (30 mL), 2,6-dibromobenzaldehyde (4.65 g, 17.62 mmol, 1.20 equiv), Cs$_2$CO$_3$ (9.6 g, 29.46 mmol, 2.00 equiv), Pd$_2$(dba)$_3$ (300 mg, 0.33 mmol, 0.10 equiv), Xantphos (300 mg, 0.52 mmol, 0.10 equiv). The resulting solution was stirred for 1 h at 100° C. in an oil bath. The reaction mixture was cooled to RT. The solids were filtered out. The resulting mixture was concentrated under vacuum. The residue was applied onto a silica gel column with ethyl acetate/petroleum ether (1:1). This resulted in 4.0 g (70%) of 2-bromo-6-[4,4-dimethyl-9-oxo-1,10-diazatricyclo[6.4.0.0^[2,6]]dodeca-2 (6),7-dien-10-yl]benzaldehyde as a off-white solid. (ES, m/z): 387[M+H]$^+$. $^1$H-NMR: (300 MHz, CD$_3$OD, ppm): δ10.36 (s, 1H), 7.43 (d, J=7.8 Hz, 1H), 7.25 (m, 2H), 6.60 (s, 1H), 3.99 (t, J=6.0 Hz, 2H), 3.63 (t, J=6.0 Hz, 3H), 2.55 (s, 2H), 2.45 (s, 2H), 1.24 (s, 6H).

Into a 50-mL round-bottom flask purged and maintained with an inert atmosphere of nitrogen, was placed a solution of 2-bromo-6-[4,4-dimethyl-9-oxo-1,10-diazatricyclo[6.4.0.0^[2,6]]dodeca-2(6),7-dien-10-yl]benzaldehyde (1.0 g, 2.58 mmol, 1.00 equiv) in dioxane (10 mL), Pin$_2$B$_2$ (1.64 g, 2.50 equiv), Pd(dppf)Cl$_2$ (100 mg, 0.14 mmol, 0.10 equiv), KOAc (760 mg, 7.74 mmol, 3.00 equiv). The resulting solution was stirred for 30 min at 100° C. in an oil bath. The reaction mixture was cooled to RT. The solids were filtered out. The resulting mixture was concentrated under vacuum. This resulted in 400 mg (44%) of (3-[4,4-dimethyl-9-oxo-1,10-diazatricyclo[6.4.0.0^[2,6]]dodeca-2(6),7-dien-10-yl]-2-formylphenyl)boronic acid as a brown solid. LC-MS: (ES, m/z): 353[M+H]$^+$.

Into a 50-mL round-bottom flask purged and maintained with an inert atmosphere of nitrogen, was placed (3-[4,4-dimethyl-9-oxo-1,10-diazatricyclo[6.4.0.0^[2,6]]dodeca-2 (6),7-dien-10-yl]-2-formylphenyl)boronic acid (346 mg, 0.98 mmol, 1.00 equiv) a solution of 3-([3-amino-4-[(2S)-2-methyl-4-(oxetan-3-yl)piperazin-1-yl]phenyl]amino)-5-bromo-1-methyl-1,2-dihydropyrazin-2-one (441 mg, 0.98 mmol, 1.00 equiv) in dioxane (10 mL)/H$_2$O (1 mL), Pd(dppf)Cl$_2$ (30 mg, 0.04 mmol, 0.10 equiv), potassium carbonate (271 mg, 1.96 mmol, 2.00 equiv). The resulting solution was stirred for 1 h at 100° C. in an oil bath. The solids were filtered out. The resulting mixture was concentrated under vacuum. This resulted in 500 mg (75%) of 2-[6-([3-amino-4-[(2S)-2-methyl-4-(oxetan-3-yl)piperazin-1-yl]phenyl]amino)-4-methyl-5-oxo-4,5-dihydropyrazin-2-yl]-6-[4,4-dimethyl-9-oxo-1,10-diazatricyclo[6.4.0.0^[2,6]] dodeca-2(6),7-dien-10-yl]benzaldehyde as brown oil. LC-MS: (ES, m/z): 677[M+H]$^+$.

Into a 25-mL round-bottom flask purged and maintained with an inert atmosphere of nitrogen was placed a solution of 2-[6-([3-amino-4-[(2S)-2-methyl-4-(oxetan-3-yl)piperazin-1-yl]phenyl]amino)-4-methyl-5-oxo-4,5-dihydropyrazin-2-yl]-6-[4,4-dimethyl-9-oxo-1,10-diazatricyclo[6.4.0.0^[2,6]]dodeca-2(6),7-dien-10-yl]benzaldehyde (500 mg, 0.74 mmol, 1.00 equiv) in ethanol (10 mL), NaBH$_4$ (16.8 mg, 0.44 mmol, 0.60 equiv). The resulting solution was stirred for 30 min at room temperature. The resulting mixture was concentrated under vacuum. The crude product was purified by Prep-HPLC. This resulted in 240 mg (48%) of 10-[3-[6-([3-amino-4-[(2S)-2-methyl-4-(oxetan-3-yl)piperazin-1-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0^[2,6]]dodeca-2(6),7-dien-9-one as a light brown solid. LC-MS: (ES, m/z): 679[M+H]$^+$.

Into a 10-mL round-bottom flask purged and maintained with an inert atmosphere of nitrogen, was placed a solution of 10-[3-[6-([3-amino-4-[(2S)-2-methyl-4-(oxetan-3-yl)piperazin-1-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0^[2,6]]dodeca-2(6),7-dien-9-one (240 mg, 0.35 mmol, 1.00 equiv) in CH$_3$CN (10 mL), prop-2-enoic acid (30.5 mg, 0.42 mmol, 1.20 equiv), HATU (147.7 mg, 0.39 mmol, 1.10 equiv), NMM (71.4 mg, 0.71 mmol, 2.00 equiv). The resulting solution was stirred for 1 h at room temperature. The crude product was purified by Prep-HPLC. This resulted in 60 mg (23%) of N-(5-[[6-(3-[4,4-dimethyl-9-oxo-1,10-diazatricyclo[6.4.0.0^[2,6]]dodeca-2 (6),7-dien-10-yl]-2-(hydroxymethyl)phenyl)-4-methyl-3-oxo-3,4-dihydropyrazin-2-yl]amino]-2-[(2S)-2-methyl-4-(oxetan-3-yl)piperazin-1-yl]phenyl)prop-2-enamide as a off-white solid. LC-MS: (ES, m/z): 733[M+H]$^+$. $^1$H-NMR: (300 MHz, d$_6$-DMSO, ppm): δ9.17 (m, 2H), 8.91 (s, 1H), 7.82-7.63 (m, 2H), 7.49-7.42 (m, 2H), 7.40-7.23 (m, 2H), 6.67-6.49 (m, 2H), 6.25 (m, 1H), 5.80 (d, J=10.5 Hz, 1H), 4.81 (m, 1H), 4.62-4.40 (m, 6H), 4.25-4.02 (m, 3H), 3.93 (m, 1H), 3.60-3.40 (m, 4H), 3.10 (m, 1H), 2.80-2.60 (m, 4H), 2.55 (s, 2H), 2.45 (s, 2H), 2.22 (m, 1H), 1.95 (t, J=6.8 Hz, 1H), 1.22 (s, 6H), 0.73 (d, J=6.0 Hz, 3H).

Example 5: Preparation of N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl) pyridin-4-yl)-4-methyl-3-oxo-3,4-dihydropyrazin-2-yl)amino)phenyl)acrylamide Into a 250-mL round-bottom flask, was placed tert-butyl N-(3-aminophenyl)carbamate (5 g, 24.01 mmol, 1.00 equiv), 3,5-dibromo-1-methyl-1,2-dihydropyrazin-2-one (5.8 g, 21.65 mmol, 1.50 equiv), DIEA (4.9 g, 37.98 mmol, 2.00 equiv), i-propanol (50 mL). The resulting solution was stirred overnight at 80° C. The resulting mixture was concentrated under vacuum. The crude product was purified by Flash PE:EA=100/20 increasing to PE:EA=100/50 within 30 min. This resulted in 7.4 g (78%) of tert-butyl N-[3-[(6-bromo-4-methyl-3-oxo-3,4-dihydropyrazin-2-yl)amino] phenyl]carbamate as a light yellow solid. LC-MS: (ES, m/z): [M+H]$^+$=395. $^1$H-NMR-: (300 MHz, CDCl$_3$, ppm): δ9.32 (s, 1H), 9.28 (s, 1H), 7.91 (s, 1H), 7.52 (d, J=5.4 Hz, 1H), 7.16-7.09 (m, 2H), 3.45 (s, 3H), 1.47 (s, 9H).

Into a 25-mL round-bottom flask, was placed tert-butyl N-[3-[(6-bromo-4-methyl-3-oxo-3,4-dihydropyrazin-2-yl) amino]phenyl]carbamate (400 mg, 0.51 mmol, 1.00 equiv), hydrogen chloride/Dioxane (10 mL). The resulting solution was stirred for 30 min at room temperature. The resulting mixture was concentrated under vacuum. This resulted in 300 mg (90%) of 3-[(3-aminophenyl)amino]-5-bromo-1-methyl-1,2-dihydropyrazin-2-one as a yellow solid. LC-MS: (ES, m/z): [M+H]$^+$=295.

Into a 50-mL round-bottom flask purged and maintained with an inert atmosphere of nitrogen, was placed 3-[(3-aminophenyl)amino]-5-bromo-1-methyl-1,2-dihydropyrazin-2-one (200 mg, 0.68 mmol, 1.00 equiv), (2-4,4-dimethyl-9-oxo-1,10-diazatricyclo[6.4.0.0^2,6]dodeca-2(6),7-dien-10-yl-3-[(oxan-2-yloxy)methyl]pyridin-4-yl)boronic acid (298 mg, 0.68 mmol, 1.00 equiv), Pd(dppf)Cl$_2$ (58 mg, 0.07 mmol, 0.10 equiv), potassium carbonate (281 mg, 2.04 mmol, 3.00 equiv), Dioxane (12 mL), water (2 mL). The resulting solution was stirred for 30 min at 100° C. The resulting mixture was concentrated under vacuum after cooled. The resulting solution was diluted with of methanol. The crude product was purified by Flash MeCN:H$_2$O=25/75 increasing to MeCN:H$_2$O=50/50 within 13 min. This resulted in 280 mg (68%) of 10-(4-[6-[(3-aminophenyl)amino]-4-methyl-5-oxo-4,5-dihydropyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one as a brown solid. LC-MS (ES, m/z): [M+H]$^+$=610.

Into a 50-mL round-bottom flask, was placed 10-(4-[6-[(3-aminophenyl)amino]-4-methyl-5-oxo-4,5-dihydropyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one (230 mg, 0.38 mmol, 1.00 equiv), trifluoroacetic acid (1 mL), dichloromethane (20 mL). The resulting solution was stirred for 30 min at room temperature. The resulting mixture was concentrated under vacuum. The resulting solution was diluted with of ethyl acetate. The pH value of the solution was adjusted to 8 with saturate solution of sodium bicarbonate. The solids were filtered out. The resulting mixture was concentrated under vacuum. This resulted in 150 mg (76%) of 10-(4-[6-[(3-aminophenyl)amino]-4-methyl-5-oxo-4,5-dihydropyrazin-2-yl]-3-(hydroxymethyl)pyridin-2-yl)-4,4-dimethyl-1,10-diazatricyclo[6.4.0.0^[2,6]]dodeca-2(6),7-dien-9-one as colorless oil. LC-MS-714-4: (ES, m/z): [M+H]$^+$=526.

Into a 25-mL round-bottom flask, was placed 10-(4-[6-[(3-aminophenyl)amino]-4-methyl-5-oxo-4,5-dihydropyrazin-2-yl]-3-(hydroxymethyl)pyridin-2-yl)-4,4-dimethyl-1,10-diazatricyclo[6.4.0.0^[2,6]]dodeca-2(6),7-dien-9-one (150 mg, 0.28 mmol, 1.00 equiv), prop-2-enoic acid (20.1 mg, 0.28 mmol, 1.00 equiv), NMM (58 mg, 0.38 mmol, 2.00 equiv), HATU (141 mg, 0.25 mmol, 1.30 equiv), MeCN (5 mL). The resulting solution was stirred for 30 min at room temperature. The crude product was purified by Prep-HPLC. This resulted in 32.4 mg (18%) of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]phenyl)prop-2-enamide as a off-white solid. LC-MS: (ES, m/z): [M+H]$^+$=580. $^1$H-NMR: (300 MHz, CDCl$_3$, ppm): δ9.99 (s, 1H), 9.24 (s, 1H), 8.47 (m, 2H), 7.84-7.73 (m, 2H), 7.60 (d, J=7.5 Hz, 1H), 7.30-7.20 (m, 2H), 6.58 (s, 1H), 6.55-6.25 (m, 2H), 5.76 (d, J=9.9 Hz, 1H), 4.97 (m, 1H), 4.64-4.45 (m, 2H), 4.33-4.15 (m, 3H), 3.88 (m, 1H), 3.57 (s, 3H), 2.59 (d, J=5.1 Hz, 2H), 2.42 (d, J=5.1 Hz, 2H), 1.22 (s, 6H).

Example 7: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-(oxetan-3-yl)piperidin-4-yl)phenyl)acrylamide Into a 250-mL round-bottom flask purged and maintained with an inert atmosphere of nitrogen, was placed 4-bromo-3-nitroaniline (5 g, 23.04 mmol, 1.00 equiv), tert-butyl 4-(tetramethyl-1,3,2-dioxaborolan-2-yl)-1,2,3,6-tetrahydropyridine-1-carboxylate (14 g, 45.28 mmol, 2.00 equiv), Pd(dppf)Cl$_2$ (2 g, 2.33 mmol, 0.10 equiv), potassium carbonate (19 g, 137.47 mmol, 6.00 equiv), Dioxane (80 mL), water (20 mL). The resulting solution was stirred overnight at 90° C. The solids were filtrated out. The resulting mixture was concentrated under vacuum. The crude product was purified by Flash PE:EA=50/50 increasing to PE:EA=20/80 within 30 min. This resulted in 5.7 g (77%) of tert-butyl 4-(4-amino-2-nitrophenyl)-1,2,3,6-tetrahydropyridine-1-carboxylate as light yellow oil. LC-MS-1: (ES, m/z): [M+H]$^+$=320. $^1$H-NMR-PH-1: (300 MHz, d$_6$-DMSO, ppm): δ7.05 (m, 2H), 6.80 (d, J=8.1 Hz, 1H), 5.74 (s, 2H), 5.49 (s, 1H), 3.88 (m, 2H), 3.46 (t, J=10.8 Hz, 2H), 2.17 (s, 2H).

Into a 250-mL round-bottom flask, was placed tert-butyl 4-(4-amino-2-nitrophenyl)-1,2,3,6-tetrahydropyridine-1-carboxylate (7 g, 21.92 mmol, 1.00 equiv), water (10 mL), sodium carbonate (4.6 g, 43.40 mmol, 2.00 equiv), dichloromethane (50 mL). The resulting mixture was stirred 30 min at 0° C. This was followed by the addition of Cbz-Cl (4.5 g, 26.47 mmol, 1.20 equiv) dropwise with stirring in 5 min at 0 0° C. The resulting solution was stirred overnight at room temperature. The resulting mixture was washed with 2×100 mL of brine. The resulting mixture was concentrated under vacuum. This resulted in 7 g (70%) of tert-butyl 4-(4-[[(benzyloxy)carbonyl]amino]-2-nitrophenyl)-1,2,3,6-tetrahydropyridine-1-carboxylate as yellow oil. LC-MS-2: (ES, m/z): [M+H]$^+$=454. $^1$H-NMR-PH-2: (300 MHz, d$_6$-DMSO, ppm): δ10.27 (s, 1H), 8.13 (s, 1H), 7.68 (d, J=8.4 Hz, 1H), 7.46-7.32 (m, 7H), 5.62 (s, 1H), 5.19 (s, 2H), 3.92 (m, 2H), 3.53 (t, J=10.8 Hz, 2H), 2.24 (s, 2H).

Into a 250-mL round-bottom flask, was placed tert-butyl 4-(4-[[(benzyloxy)carbonyl]amino]-2-nitrophenyl)-1,2,3,6-tetrahydropyridine-1-carboxylate (5 g, 11.03 mmol, 1.00 equiv), hydrogen chloride/dioxane (40 mL). The resulting solution was stirred for 1.5 h at room temperature. The resulting mixture was concentrated under vacuum. This resulted in 4.5 g (crude) of benzyl N-[3-nitro-4-(1,2,3,6-tetrahydropyridin-4-yl)phenyl]carbamate as a light yellow solid. LC-MS-3: (ES, m/z): [M+H]$^+$=354.

Into a 250-mL round-bottom flask, was placed benzyl N-[3-nitro-4-(1,2,3,6-tetrahydropyridin-4-yl)phenyl]carbamate (4.5 g, 25.47 mmol, 1.00 equiv), oxetan-3-one (1.35 g, 37.47 mmol, 1.50 equiv), NaCNBH$_3$ (1.6 g, 50.79 mmol, 2.00 equiv), methanol (30 mL). The resulting solution was stirred for 4 h at 50° C. The resulting solution was extracted with of ethyl acetate and the organic layers combined. The resulting mixture was washed with 2×100 mL of sodium chloride. The solid was dried in an oven under reduced pressure and concentrated under vacuum. This resulted in 3.6 g (61%) of benzyl N-[3-nitro-4-[1-(oxetan-3-yl)-1,2,3,6-tetrahydropyridin-4-yl]phenyl]carbamate as a white solid. LC-MS-4: (ES, m/z): [M+H]$^+$=410. $^1$H-NMR-PH-4: (300 MHz, d$_6$-DMSO, ppm): δ10.27 (s, 1H), 8.09 (s, 1H), 7.67 (d, J=8.4 Hz, 1H), 7.46-7.32 (m, 6H), 5.59 (s, 1H), 5.19 (s, 2H), 4.56 (t, J=9 Hz, 2H), 4.49 (t, J=9 Hz, 2H), 3.60 (m, 1H), 2.92 (s, 2H), 2.48 (m, 2H), 2.26 (s, 2H).

Into a 50-mL round-bottom flask, was placed benzyl N-[3-nitro-4-[1-(oxetan-3-yl)-1,2,3,6-tetrahydropyridin-4-yl]phenyl]carbamate (3.6 g, 8.79 mmol, 1.00 equiv), acetic acid (5.25 g, 87.42 mmol, 10.00 equiv), ethanol (25 mL), zinc (2.8 g, 42.81 mmol, 5.00 equiv). The resulting solution was stirred for 30 min at room temperature. The solids were filtered out. The resulting solution was concentrated under vacuum. The resulting solution was diluted with ethyl acetate. The pH was adjusted to 8 with sodium carbonate (1 mol/L). The resulting mixture was washed with 2×200 mL of H2O. The mixture was dried over anhydrous sodium sulfate and concentrated under vacuum. The crude product was purified by Flash PE:EA=100/30 increasing to PE:EA=100/50 within 45 min. This resulted in 2.5 g (75%) of benzyl N-[3-amino-4-[1-(oxetan-3-yl)-1,2,3,6-tetrahydropyridin-4-yl]phenyl]carbamate as yellow oil. LC-MS-5: (ES, m/z): [M+H]$^+$=380. $^1$H-NMR-PH-5: (300 MHz, d$_6$-DMSO, ppm): δ9.61 (s, 1H), 7.52-7.28 (m, 5H), 6.87 (s, 1H), 6.77 (d, J=7.8 Hz, 1H), 6.61 (d, J=8.1 Hz, 1H), 5.60 (s, 1H), 5.13 (s, 2H), 4.74 (s, 2H), 4.57 (t, J=9 Hz, 2H), 4.50 (t, J=9 Hz, 2H), 3.52 (m, 1H), 2.92 (s, 2H), 2.48 (m, 2H), 2.28 (s, 2H).

Into a 250-mL round-bottom flask, was placed benzyl N-[3-amino-4-[1-(oxetan-3-yl)-1,2,3,6-tetrahydropyridin-4-yl]phenyl]carbamate (2.5 g, 13.18 mmol, 1.00 equiv), TEA (2 g, 39.53 mmol, 3.00 equiv), di-tert-butyl dicarbonate (1.75 g, 16.04 mmol, 1.30 equiv), tetrahydrofuran (30 mL). The resulting solution was stirred overnight at 65° C. The resulting mixture was concentrated under vacuum. The crude product was purified by Flash PE:EA=100/30 increasing to PE:EA=100/50 within 25 min. This resulted in 2 g (63%) of benzyl N-(3-[[(tert-butoxy)carbonyl]amino]-4-[1-(oxetan-3-yl)-1,2,3,6-tetrahydropyridin-4-yl]phenyl)carbamate as yellow oil. LC-MS-6: (ES, m/z): [M+H]$^+$=480. $^1$H-NMR-PH-6: (300 MHz, d$_6$-DMSO, ppm): δ9.74 (s, 1H), 8.20 (s, 1H), 7.47-7.28 (m, 6H), 7.24 (d, J=8.1 Hz, 1H), 7.05 (d, J=8.4 Hz, 1H), 5.75 (s, 1H), 5.14 (s, 2H), 4.57 (s, 2H), 4.57 (t, J=9 Hz, 2H), 4.50 (t, J=9 Hz, 2H), 3.54 (m, 1H), 2.92 (s, 2H), 2.48 (m, 2H), 2.28 (s, 2H), 1.22 (s, 9H).

Into a 250-mL round-bottom flask purged and maintained with an inert atmosphere of H$_2$, was placed benzyl N-(3-[[(tert-butoxy)carbonyl]amino]-4-[1-(oxetan-3-yl)-1,2,3,6-tetrahydropyridin-4-yl]phenyl)carbamate (1.4 g, 2.92 mmol, 1.00 equiv), Palladium carbon (140 mg, 0.10 equiv), ethyl acetate (40 mL). The resulting solution was stirred overnight at room temperature. The solids were filtered out. The resulting mixture was concentrated under vacuum. This resulted in 610 mg (60%) of tert-butyl N-[5-amino-2-[1-(oxetan-3-yl)piperidin-4-yl]phenyl]carbamate as a light yellow solid. LC-MS-7: (ES, m/z): [M+H]$^+$=348. $^1$H-NMR-PH-7: (300 MHz, d$_6$-DMSO, ppm): δ8.26 (s, 1H), 6.90 (d, J=7.8 Hz, 1H), 6.40 (m, 2H), 4.87 (s, 2H), 4.54 (t, J=7.2 Hz, 2H), 4.46 (t, J=7.2 Hz, 2H), 3.37 (m, 1H), 2.78 (d, J=10.8 Hz, 2H), 2.60 (m, 1H), 1.80-1.45 (m, 6H), 1.21 (s, 9H).

Into a 50-mL round-bottom flask purged and maintained with an inert atmosphere of nitrogen, was placed tert-butyl N-[5-amino-2-[1-(oxetan-3-yl)piperidin-4-yl]phenyl]carbamate (600 mg, 2.30 mmol, 1.00 equiv), 3,5-dibromo-1-methyl-1,2-dihydropyrazin-2-one (550 mg, 2.74 mmol, 1.20 equiv), DIEA (435 mg, 4.50 mmol, 2.50 equiv), i-propanol (25 mL). The resulting solution was stirred overnight at 80° C. The resulting mixture was concentrated under vacuum. The crude product was purified by Flash PE:EA=100/85. This resulted in 600 mg (65%) of tert-butyl N-[5-[(6-bromo-4-methyl-3-oxo-3,4-dihydropyrazin-2-yl)amino]-2-[1-(oxetan-3-yl)piperidin-4-yl]phenyl]carbamate as a light yellow solid. LC-MS-8: (ES, m/z): [M+H]$^+$=534. $^1$H-NMR-PH-8: (300 MHz, d$_6$-DMSO, ppm): δ9.40 (s, 1H), 8.57 (s, 1H), 7.79 (s, 1H), 7.72 (d, J=8.4 Hz, 1H), 7.32 (s, 1H), 7.23 (d, J=8.4 Hz, 1H), 4.54 (t, J=6.3 Hz, 2H), 4.46 (t, J=6.3 Hz, 2H), 3.45-3.37 (m, 5H), 2.83-2.70 (m, 3H), 1.83-1.52 (m, 6H), 1.38 (s, 9H).

Into a 250-mL round-bottom flask, was placed tert-butyl N-[5-[(6-bromo-4-methyl-3-oxo-3,4-dihydropyrazin-2-yl)amino]-2-[1-(oxetan-3-yl)piperidin-4-yl]phenyl]carbamate (600 mg, 1.12 mmol, 1.00 equiv), trifluoroacetic acid (2 mL), dichloromethane (20 mL). The resulting solution was stirred for 3 h at room temperature. The resulting mixture was concentrated under vacuum. The resulting solution was diluted with methanol and pH was adjusted to 8 with potassium carbonate. The solids were filtered out. The resulting mixture was concentrated under vacuum. This resulted in 410 mg (84%) of 3-([3-amino-4-[1-(oxetan-3-yl)piperidin-4-yl]phenyl]amino)-5-bromo-1-methyl-1,2-dihydropyrazin-2-one as a light yellow solid. LC-MS-9: (ES, m/z): [M+H]$^+$=434.

Into a 50-mL round-bottom flask purged and maintained with an inert atmosphere of nitrogen, was placed 3-([3-amino-4-[1-(oxetan-3-yl)piperidin-4-yl]phenyl]amino)-5-bromo-1-methyl-1,2-dihydropyrazin-2-one (300 mg, 0.7 mmol, 1.00 equiv), (2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)boronic acid (350 mg, 0.8 mmol, 1.10 equiv), Pd(dppf)Cl$_2$ (60 mg, 0.03 mmol, 0.10 equiv), K$_2$CO$_3$ (286 mg, 2.03 mmol, 3.00 equiv), Dioxane (20 mL), water (2 mL). The resulting solution was stirred for 30 min at 100° C. The resulting mixture was concentrated under vacuum. The resulting solution was diluted with of methanol. The crude product was purified by Flash MeCN:H$_2$O=20/80 increasing to MeCN:H$_2$O=55/45 within 12 min. This resulted in 210 mg (81%) of 10-[4-[6-([3-amino-4-[1-(oxetan-3-yl)piperidin-4-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one as a light yellow solid. LC-MS-10: (ES, m/z): [M+H]$^+$=749.

Into a 25-mL round-bottom flask, was placed 10-[4-[6-([3-amino-4-[1-(oxetan-3-yl)piperidin-4-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one (210 mg, 0.28 mmol, 1.00 equiv), dichloromethane (10 mL), trifluoroacetic acid (1 mL). The resulting solution was stirred for 1 h at room temperature. The resulting mixture was concentrated under vacuum and pH was adjusted to 8 with sodium bicarbonate solution. The resulting mixture was extracted with EA and washed with brine. The mixture was dried over anhydrous sodium sulfate and concentrated under vacuum. This resulted in 135 mg (72%) of 10-[4-[6-([3-amino-4-[1-(oxetan-3-yl)piperidin-4-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one as a light yellow solid. LC-MS-11: (ES, m/z): [M+H]$^+$=665. $^1$H-NMR-PH-11: (300 MHz, CDCl$_3$, ppm): δ8.55 (d, J=5.1 Hz, 1H), 8.20 (s, 1H), 8.00 (s, 1H), 7.76 (d, J=5.1 Hz, 1H), 7.29 (s, 1H), 7.23 (d, J=5.7 Hz, 1H), 7.23 (d, J=5.4 Hz, 1H), 6.85 (s, 1H), 5.02 (m, 1H), 4.82-4.37 (m, 7H), 4.20 (m, 2H), 3.92 (m, 1H), 3.70-3.50 (m, 5H), 2.98 (m, 2H), 2.62-2.47 (m, 5H), 2.07-1.82 (m, 6H), 1.73-1.45 (m, 5H), 1.28 (s, 6H).

Into a 25-mL round-bottom flask, was placed 10-[4-[6-([3-amino-4-[1-(oxetan-3-yl)piperidin-4-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one (135 mg, 0.23 mmol, 1.00 equiv), prop-2-enoic acid (17 mg, 0.23 mmol, 1.00 equiv), HATU (94 mg, 0.25 mmol, 1.10 equiv), NMM (54 mg, 0.53 mmol, 2.50 equiv), MeCN (5 mL). The resulting solution was stirred for 30 min at room temperature. The crude product was purified by Prep-HPLC. This resulted in 15.2 mg (11%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-2-[1-(oxetan-3-yl)piperidin-4-yl]phenyl) prop-2-enamide as a white solid. LC-MS-0: (ES, m/z): [M+H]⁺=719. ¹H-NMR-PH-0: (300 MHz, CDCl₃, ppm): δ9.54 (s, 1H), 9.32 (s, 1H), 8.45 (d, J=4.8 Hz, 1H), 8.32 (m, 1H), 7.79-7.70 (m, 3H), 7.25 (d, J=8.7 Hz, 1H), 6.61-6.44 (m, 2H), 6.27 (m, 1H), 5.75 (d, J=10.8 Hz, 1H), 5.01 (m, 1H), 4.67-4.42 (m, 6H), 4.35-4.15 (m, 3H), 3.87 (m, 1H), 3.57 (s, 3H), 3.40 (m, 1H), 2.85-2.57 (m, 5H), 2.45 (m, 2H), 1.84-1.55 (m, 6H), 1.23 (s, 6H).

Example 8: Preparation of N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(1-(oxetan-3-yl)piperidin-4-yl)phenyl) acrylamide Into a 25-mL round-bottom flask purged and maintained with an inert atmosphere of nitrogen, was placed 3-([3-amino-4-[1-(oxetan-3-yl)piperidin-4-yl]phenyl]amino)-5-bromo-1-methyl-1,2-dihydropyrazin-2-one (300 mg, 0.69 mmol, 1.00 equiv), (3-[4,4-dimethyl-9-oxo-1,10-diazatricyclo[6.4.0.0ˆ[2,6]]dodeca-2(6),7-dien-10-yl]-2-formylphenyl)boronic acid (260 mg, 0.74 mmol, 1.10 equiv), Pd(dppf)Cl₂ (35 mg, 0.05 mmol, 0.10 equiv), potassium carbonate (286 mg, 2.07 mmol, 3.00 equiv), Dioxane (15 mL), water (2 mL). The resulting solution was stirred for 40 min at 100° C. for 2 h. The resulting mixture was concentrated under vacuum. The resulting solution was extracted with of methanol and the organic layers combined. The crude product was purified by Flash MeCN:H2O=30/70 increasing to MeCN:H2O=65/35 within 12 min. This resulted in 268 mg (59%) of 2-[6-([3-amino-4-[1-(oxetan-3-yl)piperidin-4-yl]phenyl]amino)-4-methyl-5-oxo-4,5-dihydropyrazin-2-yl]-6-[4,4-dimethyl-9-oxo-1,10-diazatricyclo[6.4.0.0ˆ[2,6]]dodeca-2(6),7-dien-10-yl]benzaldehyde as a light yellow solid. LC-MS-1: (ES, m/z): 662[M+H]⁺.

Into a 25-mL round-bottom flask, was placed 2-[6-(3-amino-4-[1-(oxetan-3-yl)piperidin-4-yl]phenylamino)-4-methyl-5-oxo-4,5-dihydropyrazin-2-yl]-6-4,4-dimethyl-9-oxo-1,10-diazatricyclo[6.4.0.0ˆ2,6]dodeca-2(6),7-dien-10-ylbenzaldehyde (240 mg, 0.36 mmol, 1.00 equiv), NaBH₄ (7 mg, 0.18 mmol, 0.50 equiv), ethanol (8 mL). The resulting solution was stirred for 30 min at room temperature. The resulting solution was concentrated and diluted with methanol. The pH was adjusted to 8 with potassium carbonate. The solids were filtered out and the filtrate was concentrated under vacuum. This resulted in 132 mg (55%) of 10-[3-[6-([3-amino-4-[1-(oxetan-3-yl)piperidin-4-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0ˆ[2,6]]dodeca-2(6),7-dien-9-one as light yellow oil. LC-MS-2: (ES, m/z): 664[M+H]⁺ ¹H-NMR-PH-2: (300 MHz, d₆-DMSO, ppm): δ8.71 (s, 1H), 7.53-7.25 (m, 5H), 7.04 (d, J=8.4 Hz, 1H), 6.90 (d, J=8.4 Hz, 1H), 6.53 (s, 1H), 4.81 (m, 3H), 4.62-4.40 (m, 6H), 4.25-4.02 (m, 3H), 3.93 (m, 1H), 3.55 (s, 1H), 3.35 (m, 1H), 2.80 (m, 2H), 2.55 (s, 2H), 2.45 (s, 2H), 1.95-1.4 (m, 7H), 1.22 (s, 6H).

Into a 25-mL round-bottom flask, was placed 10-[3-[6-([3-amino-4-[1-(oxetan-3-yl)piperidin-4-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0ˆ[2,6]]dodeca-2(6),7-dien-9-one (100 mg, 0.15 mmol, 1.00 equiv), prop-2-enoic acid (12 mg, 0.17 mmol, 1.10 equiv), HATU (68 mg, 0.18 mmol, 1.20 equiv), NMM (30 mg, 0.30 mmol, 2.00 equiv), MeCN (4 mL). The resulting solution was stirred for 30 min at room temperature. The crude product was purified by Prep-HPLC. This resulted in 20.5 mg (20%) of N-(5-[[6-(3-[4,4-dimethyl-9-oxo-1,10-diazatricyclo[6.4.0.0ˆ[2,6]]dodeca-2(6),7-dien-10-yl]-2-(hydroxymethyl)phenyl)-4-methyl-3-oxo-3,4-dihydropyrazin-2-yl]amino]-2-[1-(oxetan-3-yl)piperidin-4-yl]phenyl)prop-2-enamide as a white solid. LC-MS-0: (ES, m/z): 718[M+H]⁺ ¹H-NMR-PH-0: (300 MHz, CDCl₃, ppm): δ8.28 (s, 1H), 7.95 (s, 1H), 7.70-7.20 (m, 7H), 6.80 (s, 1H), 6.45-6.25 (m, 2H), 5.73 (s, 1H), 4.70 (m, 4H), 4.62-4.37 (m, 3H), 4.25-4.10 (m, 3H), 3.95 (m, 1H), 3.65 (s, 3H), 3.55 (m, 1H), 2.90 (m, 2H), 2.70-2.45 (m, 6H), 2.04-1.80 (m, 5H), 1.26 (s, 6H).

Example 9: Preparation of N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-(4-methylpiperazin-1-yl)phenyl) acrylamide Into a 250-mL round-bottom flask purged and maintained with an inert atmosphere of nitrogen, was placed a solution of 1-bromo-3,5-dinitrobenzene (5.5 g, 22.27 mmol, 1.00 equiv) in dioxane (50 mL), 1-methylpiperazine (2.64 g, 26.36 mmol, 1.20 equiv), Cs₂CO₃ (14.5 g, 44.50 mmol, 2.00 equiv). This was followed by the addition of Pd₂(dba)₃ (550 mg, 0.60 mmol, 0.10 equiv), BINAP (770 mg, 1.24 mmol, 0.15 equiv). The resulting solution was stirred overnight at 100° C. in an oil bath. The reaction mixture was cooled to 25° C. The solids were filtered out. The resulting mixture was concentrated under vacuum. The residue was applied onto a silica gel column with ethyl acetate/hexane (1:1). This resulted in 4.0 g (67%) of 1-(3,5-dinitrophenyl)-4-methylpiperazine as a yellow solid. LC-MS-1: (ES, m/z): 267 [M+H]⁺.

Into a 25-mL round-bottom flask purged and maintained with an inert atmosphere of H₂, was placed a solution of 1-(3,5-dinitrophenyl)-4-methylpiperazine (1.3 g, 4.88 mmol, 1.00 equiv) in methanol (10 mL), Palladium carbon (0.1 g, 0.10 equiv). The resulting solution was stirred for 2 h at room temperature. The solids were filtered out. The resulting mixture was concentrated under vacuum. This resulted in 1.0 g (99%) of 5-(4-methylpiperazin-1-yl)benzene-1,3-diamine as brown oil. LC-MS-2: (ES, m/z): 207 [M+H]⁺. ¹H-NMR-PH-1: (300 MHz, d₆-DMSO, ppm): δ5.44 (s, 2H), 5.38 (s, 1H), 4.49 (s, 4H), 2.95 (t, J=6.5 Hz, 4H), 2.38 (t, J=6.5 Hz, 4H), 2.19 (s, 3H).

Into a 50-mL round-bottom flask purged and maintained with an inert atmosphere of nitrogen, was placed a solution of 3,5-dibromo-1-methyl-1,2-dihydropyrazin-2-one (1.0 g, 3.73 mmol, 1.00 equiv) in IPA (10 mL), 5-(4-methylpiperazin-1-yl)benzene-1,3-diamine (1.0 g, 4.85 mmol, 1.00 equiv), DIEA (530 mg, 4.10 mmol, 1.10 equiv). The resulting solution was stirred for 1 h at 40° C. in an oil bath. The reaction mixture was cooled to 25° C. The solids were collected by filtration. This resulted in 0.5 g (34%) of 3-[[3-amino-5-(4-methylpiperazin-1-yl)phenyl]amino]-5-bromo-1-methyl-1,2-dihydropyrazin-2-one as a brown solid. LC-MS-3: (ES, m/z): 392[M+H]⁺.

Into a 25-mL round-bottom flask purged and maintained with an inert atmosphere of nitrogen, was placed a solution of 3-[[3-amino-5-(4-methylpiperazin-1-yl)phenyl]amino]-5-bromo-1-methyl-1,2-dihydropyrazin-2-one (300 mg, 0.76 mmol, 1.00 equiv) in dioxane (10 mL)/H₂O (1 mL), (2-[4,4-dimethyl-9-oxo-1,10-diazatricyclo[6.4.0.0ˆ[2,6]]dodeca-2(6),7-dien-10-yl]-3-[(oxan-2-yloxy)methyl]pyridin-4-yl)boronic acid (300 mg, 0.68 mmol, 1.00 equiv), potassium carbonate (240 mg, 1.74 mmol, 2.00 equiv). This was followed by the addition of Pd(dppf)Cl$_2$ (30 mg, 0.04 mmol, 0.10 equiv). The resulting solution was stirred for 1 h at 100° C. in an oil bath. The resulting mixture was concentrated under vacuum. The residue was applied onto column with CH$_3$CN:H$_2$O (1:1). This resulted in 190 mg (35%) of 10-[4-(6-[[3-amino-5-(4-methylpiperazin-1-yl)phenyl]amino]-4-methyl-5-oxo-4,5-dihydropyrazin-2-yl)-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS-4: (ES, m/z): 708 [M+H]$^+$.

Into a 25-mL round-bottom flask purged and maintained with an inert atmosphere of nitrogen, was placed a solution of 10-[4-(6-[[3-amino-5-(4-methylpiperazin-1-yl)phenyl]amino]-4-methyl-5-oxo-4,5-dihydropyrazin-2-yl)-3-[(oxan-2-yloxy)methyl]pyridin-2-yl]-4,4-dimethyl-1,10-diazatricyclo[6.4.0.0^[2,6]]dodeca-2(6),7-dien-9-one (190 mg, 0.27 mmol, 1.00 equiv) in dichloromethane (5 mL), trifluoroacetic acid (1 mL). The resulting solution was stirred for 20 mins at 40° C. in an oil bath. The resulting mixture was concentrated under vacuum. This resulted in 190 mg (crude) of 10-[4-(6-[[3-amino-5-(4-methylpiperazin-1-yl)phenyl]amino]-4-methyl-5-oxo-4,5-dihydropyrazin-2-yl)-3-(hydroxymethyl)pyridin-2-yl]-4,4-dimethyl-1,10-diazatricyclo[6.4.0.0^[2,6]]dodeca-2(6),7-dien-9-one as brown oil. LC-MS-5: (ES, m/z): 624[M+H]$^+$.

Into a 25-mL round-bottom flask purged and maintained with an inert atmosphere of nitrogen, was placed prop-2-enoic acid (21 mg, 0.29 mmol, 1.10 equiv), HATU (122.5 mg, 0.32 mmol, 1.20 equiv), NMM (54 mg, 0.53 mmol, 2.00 equiv). The resulting mixture was stirred 10 min. To the mixture was added 10-[4-(6-[[3-amino-5-(4-methylpiperazin-1-yl)phenyl]amino]-4-methyl-5-oxo-4,5-dihydropyrazin-2-yl)-3-(hydroxymethyl)pyridin-2-yl]-4,4-dimethyl-1,10-diazatricyclo[6.4.0.0^[2,6]]dodeca-2(6),7-dien-9-one (190 mg, 0.30 mmol, 1.00 equiv). The resulting solution was stirred for 1 h at room temperature. The crude product was purified by Flash-Prep-HPLC. This resulted in 23 mg (11%) of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-5-(4-methylpiperazin-1-yl)phenyl)prop-2-enamide as a light brown solid. LC-MS-0: (ES, m/z): 678[M+H]$^+$. $^1$H-NMR-PH-1: (300 MHz, d$_6$-DMSO, ppm): δ9.88 (s, 1H), 9.02 (s, 1H), 8.49 (d, J=5.1 Hz, 1H), 7.80-7.74 (m, 3H), 7.50 (s, 1H), 6.97 (s, 1H), 6.57 (s, 1H), 6.52-6.25 (m, 2H), 5.75 (d, J=9.6H, 1H), 5.02 (m, 1H), 4.67-4.49 (m, 2H), 4.32-4.15 (m, 3H), 3.90 (m, 1H), 3.55 (s, 3H), 3.13 (m, 4H), 2.60 (m, 2H), 2.45 (m, 6H), 2.25 (s, 3H), 1.23 (s, 3H).

Example 10: Preparation of N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-((4-methylpiperazin-1-yl)methyl)phenyl)acrylamide Synthesis of 1-[(3,5-dinitrophenyl)methyl]-4-methylpiperazine: Into a 250-mL round-bottom flask, was placed 1-(chloromethyl)-3,5-dinitrobenzene (3 g, 13.85 mmol, 1.00 equiv), 1-methylpiperazine (1.38 g, 13.78 mmol, 1.00 equiv), potassium carbonate (4.8 g, 34.73 mmol, 2.50 equiv), tetrahydrofuran (30 mL). The resulting solution was stirred overnight at 70° C. The reaction mixture was cooled to room temperature. The solids were filtered out. The filtrate was concentrated under vacuum. The crude product was purified by re-crystallization from ether. This resulted in 3 g (77%) of 1-[(3,5-dinitrophenyl)methyl]-4-methylpiperazine as a yellow solid. LC-MS-718-1: (ES, m/z): 281 [M+H]$^+$ $^1$H-NMR-PH-718-1: (300 MHz, d$_6$-DMSO, ppm): δ8.73 (s, 1H), 8.56 (s, 2H), 3.74 (s, 2H), 2.44 (br s, 4H), 2.34 (br s, 4H), 2.16 (s, 3H).

Synthesis of 5-[(4-methylpiperazin-1-yl)methyl]benzene-1,3-diamine: Into a 250-mL round-bottom flask purged and maintained with an inert atmosphere of H$_2$, was placed 1-[(3,5-dinitrophenyl)methyl]-4-methylpiperazine (2.0 g, 7.14 mmol, 1.00 equiv), Palladium carbon (0.2 g, 0.10 equiv), methanol (40 mL). The resulting solution was stirred for 3 h at room temperature. The solids were filtered out. The filtrate was concentrated under vacuum.

This resulted in 1.1 g (70%) of 5-[(4-methylpiperazin-1-yl)methyl]benzene-1,3-diamine as colorless oil. LC-MS-718-2: (ES, m/z): 221 [M+H]$^+$. $^1$H-NMR-PH-718-2: (300 MHz, d$_6$-DMSO, ppm): δ5.76 (s, 2H), 5.70 (s, 1H), 4.61 (s, 4H), 3.12 (s, 2H), 2.30 (br s, 8H), 2.15 (s, 3H).

Synthesis of 3-([3-amino-5-[(4-methylpiperazin-1-yl)methyl]phenyl]amino)-5-bromo-1-methyl-1,2-dihydropyrazin-2-one: Into a 50-mL round-bottom flask, was placed 3,5-dibromo-1-methyl-1,2-dihydropyrazin-2-one (1.0 g, 1.00 equiv), 5-[(4-methylpiperazin-1-yl)methyl]benzene-1,3-diamine (0.7 g, 1.00 equiv), DIEA (1.0 g, 7.74 mmol, 2.50 equiv), i-propanol (15 mL). The resulting solution was stirred overnight at 80° C. The reaction mixture was cooled to room temperature. The resulting mixture was concentrated under vacuum. The crude product was purified by Prep-HPLC. This resulted in 153 mg (14%) of 3-([3-amino-5-[(4-methylpiperazin-1-yl)methyl]phenyl]amino)-5-bromo-1-methyl-1,2-dihydropyrazin-2-one as a light yellow solid. LC-MS-718-3: (ES, m/z): 407 [M+H]$^+$. $^1$H-NMR-PH-718-3: (300 MHz, d$_6$-DMSO, ppm): δ8.92 (s, 1H), 7.28 (s, 1H), 6.95-6.93 (m, 2H), 6.28 (s, 1H), 5.01 (s, 2H), 3.44 (s, 3H), 3.27 (s, 2H), 2.39-2.36 (m, 8H), 2.15 (s, 3H).

Synthesis of 10-[4-[6-([3-amino-5-[(4-methylpiperazin-1-yl)methyl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one: Into a 50-mL round-bottom flask purged and maintained with an inert atmosphere of nitrogen, was placed 3-([3-amino-5-[(4-methylpiperazin-1-yl)methyl]phenyl]amino)-5-bromo-1-methyl-1,2-dihydropyrazin-2-one (100 mg, 0.25 mmol, 1.00 equiv), (2-[4,4-dimethyl-9-oxo-1,10-diazatricyclo[6.4.0.0^ [2,6]]dodeca-2(6),7-dien-10-yl]-3-[(oxan-2-yloxy)methyl]pyridin-4-yl)boronic acid (120 mg, 0.27 mmol, 1.10 equiv), Pd(dppf)Cl$_2$ (20 mg, 0.03 mmol, 0.10 equiv), potassium carbonate (68 mg, 0.49 mmol, 2.00 equiv), dioxane (10 mL), water (1 mL). The resulting solution was stirred for 30 min at 80° C. The reaction mixture was cooled to room temperature. The solids were filtered out. The filtrate was concentrated under vacuum. The crude product was purified by Prep-HPLC. This resulted in 30 mg (17%) of 10-[4-[6-([3-amino-5-[(4-methylpiperazin-1-yl)methyl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS-718-4: (ES, m/z): 722 [M+H]$^+$.

Synthesis of 10-[4-[6-([3-amino-5-[(4-methylpiperazin-1-yl)methyl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one:
Into a 25-mL round-bottom flask, was placed dichloromethane (2 mL), trifluoroacetic acid (0.2 mL), 10-4-[6-(3-amino-5-[(4-methylpiperazin-1-yl)methyl]phenylamino)-4-methyl-5-oxo-4,5-dihydropyrazin-2-yl]-3-[(oxan-2-yloxy)methyl]pyridin-2-yl-4,4-dimethyl-1,10-diazatricyclo

[6.4.0.0^2,6]dodeca-2(6),7-dien-9-one (30 mg, 0.03 mmol, 1.00 equiv). The resulting solution was stirred for 30 min at room temperature. The resulting mixture was concentrated under vacuum. This resulted in 20 mg (74%) of 10-[4-[6-([3-amino-5-[(4-methylpiperazin-1-yl)methyl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one as yellow oil. LC-MS-718-5: (ES, m/z): 638 [M+H]+.

Synthesis of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-5-[(4-methylpiperazin-1-yl)methyl]phenyl)prop-2-enamide: Into a 25-mL round-bottom flask, was placed prop-2-enoic acid (20 mg, 0.28 mmol, 1.00 equiv), 10-4-[6-(3-amino-5-[(4-methylpiperazin-1-yl)methyl]phenylamino)-4-methyl-5-oxo-4,5-dihydropyrazin-2-yl]-3-(hydroxymethyl)pyridin-2-yl-4,4-dimethyl-1,10-diazatricyclo[6.4.0.0^2,6]dodeca-2(6),7-dien-9-one (2.7 mg, 1.20 equiv), HATU (14 mg, 1.20 equiv), NMM (8 mg, 2.50 equiv), MeCN (2 mL). The resulting solution was stirred for 30 min at room temperature. The crude product was purified by Prep-HPLC. This resulted in 5 mg (3%) of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-5-[(4-methylpiperazin-1-yl)methyl]phenyl)prop-2-enamide as a brown solid. LC-MS-718-0: (ES, m/z): 692 [M+H]+. $^1$H-NMR-PH-718-0: (300 MHz, $d_6$-DMSO, ppm): δ8.56-8.52 (m, 2H), 8.33 (s, 1H), 7.83-7.78 (m, 3H), 7.30 (s, 2H), 6.82 (s, 1H), 6.44 (d, J=15.3 Hz, 1H), 6.30 (dd, J=17.1, 9.9 Hz, 1H), 5.74 (dd, J=9.9, 1.5 Hz, 1H), 4.84-4.79 (m, 1H), 4.54-4.50 (m, 2H), 4.16-4.12 (m, 2H), 3.93-3.90 (m, 1H), 3.65 (s, 3H), 3.49 (s, 2H), 2.56-2.51 (m, 13H), 2.32 (s, 3H), 1.27 (s, 6H).

Example 11: Preparation of (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide Synthesis of 2,4-dibromo-3-methylpyridine: Into a 250-mL 3-necked round-bottom flask purged and maintained with an inert atmosphere of nitrogen, was placed a solution of (i-Pr)$_2$NH (3.19 g, 1.50 equiv) in tetrahydrofuran (50 mL). This was followed by the addition of n-C$_4$H$_9$Li (10 ml, 1.5 equiv) at −30° C. and the mixture was stirred at the same temperature for 30 min. This was followed by the addition of 2,4-dibromopyridine (5 g, 21.11 mmol, 1.00 equiv) at −70° C. and the mixture was stirred at the same temperature for 30 min. To the above solution was added iodomethane (4.5 g, 1.50 equiv) at −70° C. The resulting solution was stirred for 30 min at −70° C. The reaction was then quenched by the addition of 100 mL aqueous NH$_4$Cl. The resulting solution was extracted with 3×50 mL of ethyl acetate and the organic layers combined and dried with Na$_2$SO$_4$. The solids were filtered out. The filtrate was concentrated under vacuum. The residue was applied onto a silica gel column with ethyl acetate/petroleum ether (1:1). This resulted in 3.0 g (57%) of 2,4-dibromo-3-methylpyridine as a white solid. LC-MS-727-1: (ES, m/z): 252 [M+H]+ $^1$H-NMR-PH-727-1: (300 MHz, CDCl$_3$, ppm): δ7.99 (d, J=5.1 Hz, 1H), 7.45 (d, J=5.1 Hz, 1H), 2.58 (s, 3H).

Synthesis of 10-(4-bromo-3-methylpyridin-2-yl)-4,4-dimethyl-1,10-diazatricyclo[6.4.0.0^[2,6]]dodeca-2(6),7-dien-9-one: Into a 50-mL round-bottom flask purged and maintained with an inert atmosphere of nitrogen, was placed a solution of 4,4-dimethyl-1,10-diazatricyclo[6.4.0.0^[2,6]]dodeca-2(6),7-dien-9-one (1.0 g, 4.90 mmol, 1.00 equiv) in dioxane (10 mL). Then 2,4-dibromo-3-methylpyridine (1.59 g, 6.34 mmol, 1.30 equiv), Pd$_2$(dba)$_3$ (100 mg, 0.11 mmol, 0.10 equiv), Xantphos (100 mg, 0.17 mmol, 0.10 equiv), Cs$_2$CO$_3$ (3.19 g, 9.79 mmol, 2.00 equiv) were added to the mixture. The resulting solution was stirred for 1.5 h at 100° C. in an oil bath. The reaction mixture was cooled to room temperature. The solids were filtered out. The filtrate was concentrated under vacuum. The residue was applied onto a silica gel column with ethyl acetate/petroleum ether (1:1). This resulted in 1.0 g (55%) of 10-(4-bromo-3-methylpyridin-2-yl)-4,4-dimethyl-1,10-diazatricyclo[6.4.0.0^[2,6]]dodeca-2(6),7-dien-9-one as a brown solid. LC-MS-727-2 (ES, m/z): 374 [M+H]+. $^1$H-NMR-PH-727-1: (300 MHz, CDCl$_3$, ppm): δ8.10 (d, J=5.4 Hz, 1H), 7.41 (d, J=5.1 Hz, 1H), 6.79 (s, 1H), 4.44-4.41 (m, 1H), 4.15-4.09 (m, 2H), 3.90-3.86 (m, 1H), 2.54 (s, 2H), 2.49 (s, 2H), 2.34 (s, 3H), 1.25 (s, 6H).

Synthesis of (2-[4,4-dimethyl-9-oxo-1,10-diazatricyclo[6.4.0.0^[2,6]]dodeca-2(6),7-dien-10-yl]-3-methylpyridin-4-yl)boronic acid: Into a 25-mL round-bottom flask purged and maintained with an inert atmosphere of nitrogen, was placed a solution of 10-(4-bromo-3-methylpyridin-2-yl)-4,4-dimethyl-1,10-diazatricyclo[6.4.0.0^[2,6]]dodeca-2(6),7-dien-9-one (500 mg, 1.34 mmol, 1.00 equiv) in dioxane (5 mL) and then to the solution was added Pin$_2$B$_2$ (850 mg, 2.50 equiv), KOAc (400 mg, 4.08 mmol, 3.00 equiv), Pd(dppf)Cl$_2$ (50 mg, 0.07 mmol, 0.10 equiv). The resulting solution was stirred for 1 h at 100° C. in an oil bath. The reaction mixture was cooled to room temperature. The solids were filtered out. The filtrate was concentrated under vacuum. The residue was purified by Flash-Prep-HPLC with CH$_3$CN:H$_2$O (1:1). This resulted in 150 mg (33%) of (2-[4,4-dimethyl-9-oxo-1,10-diazatricyclo[6.4.0.0^[2,6]]dodeca-2(6),7-dien-10-yl]-3-methylpyridin-4-yl)boronic acid as a brown solid. LC-MS-727-3: (ES, m/z): 340 [M+H]+.

Synthesis of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-methylpyridin-2-yl]-4,4-dimethyl-1,10-diazatricyclo[6.4.0.0^[2,6]]dodeca-2(6),7-dien-9-one: Into a 25-mL round-bottom flask purged and maintained with an inert atmosphere of nitrogen, was placed a solution of (2-[4,4-dimethyl-9-oxo-1,10-diazatricyclo[6.4.0.0^[2,6]]dodeca-2(6),7-dien-10-yl]-3-methylpyridin-4-yl)boronic acid (120 mg, 0.35 mmol, 1.00 equiv) in dioxane (1 mL), then to the solution was added 3-([3-amino-4-[(2S)-2-methyl-4-(oxetan-3-yl)piperazin-1-yl]phenyl]amino)-5-bromo-1-methyl-1,2-dihydropyrazin-2-one (100 mg, 0.22 mmol, 1.10 equiv), Pd(dppf)Cl$_2$ (10 mg, 0.01 mmol, 1.00 equiv), potassium carbonate (73 mg, 0.53 mmol, 2.00 equiv). The resulting solution was stirred for 1 h at 100° C. in an oil bath. The reaction mixture was cooled to room temperature. The resulting mixture was concentrated under vacuum. The residue was purified by Flash-Prep-HPLC. This resulted in 120 mg (51%) of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-methylpyridin-2-yl]-4,4-dimethyl-1,10-diazatricyclo[6.4.0.0^[2,6]]dodeca-2(6),7-dien-9-one as a brown solid. LC-MS-727-4: (ES, m/z): 664 [M+H]+.

Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxo-3,4-dihydropyrazin-2-yl]amino]-2-[(2S)-2-methyl-4-(oxetan-3-yl)piperazin-1-yl]phenyl)prop-2-enamide: Into a 25-mL round-bottom flask purged and maintained with an inert atmosphere of nitrogen, was placed a solution of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-methylpyridin-2-yl]-4,4-dimethyl-1,10-diazatricyclo[6.4.0.0ˆ[2,6]]dodeca-2(6),7-dien-9-one (200 mg, 0.30 mmol, 1.00 equiv) in CH₃CN (1 mL) and then to the solution was added prop-2-enoic acid (21.7 mg, 0.30 mmol, 1.00 equiv), HATU (115 mg, 0.30 mmol, 1.00 equiv), NMM (61 mg, 0.60 mmol, 2.00 equiv). The resulting solution was stirred for 4 h at room temperature. The resulting mixture was concentrated under vacuum. The crude product was purified by Flash-Prep-HPLC. This resulted in 21.1 mg (10%) of N-(5-[[6-(2-[4,4-dimethyl-9-oxo-1,10-diazatricyclo[6.4.0.0ˆ[2,6]]dodeca-2(6),7-dien-10-yl]-3-methylpyridin-4-yl)-4-methyl-3-oxo-3,4-dihydropyrazin-2-yl]amino]-2-[(2S)-2-methyl-4-(oxetan-3-yl)piperazin-1-yl]phenyl)prop-2-enamide as a light yellow solid. LC-MS-727-0: (ES, m/z): 718 [M+H]⁺. ¹H-NMR-PH-727-1: (300 MHz, d₆-DMSO₃, ppm): δ8.88 (d, J=5.7 Hz, 1H), 8.32 (d, J=5.7 Hz, 1H), 7.67-7.59 (m, 2H), 7.33-7.27 (m, 2H), 6.64-6.55 (m, 2H), 6.24 (d, J=16.5 Hz, 1H), 5.76 (d, J=11.4 Hz, 1H), 4.72-4.65 (m, 4H), 4.19-4.09 (m, 4H), 3.90-3.83 (m, 2H), 3.54 (s, 3H), 3.30-3.12 (m, 3H), 3.00-2.83 (m, 3H), 2.51 (s, 2H), 2.40 (s, 2H), 2.26 (s, 3H), 1.18 (s, 6H), 0.74-0.71 (m, 3H).

Example 12: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-morpholinopiperidin-1-yl)phenyl)acrylamide Synthesis of tert-butyl 2-methyl-4-(morpholin-4-yl)piperidine-1-carboxylate: Into a 500-mL round-bottom flask, was placed tert-butyl 2-methyl-4-oxopiperidine-1-carboxylate (18 g, 84.40 mmol, 1.00 equiv), morpholine (8 g, 91.83 mmol, 1.10 equiv), NaCNBH₃ (10 g, 2.00 equiv), ethanol (200 mL). The resulting solution was stirred overnight at 50° C. The resulting mixture was concentrated under vacuum. The crude product was purified by Flash-Prep-HPLC. This resulted in 9.4 g (39%) of tert-butyl 2-methyl-4-(morpholin-4-yl)piperidine-1-carboxylate as colorless oil. LC-MS-729-1: (ES, m/z): 285 [M+H]⁺. ¹H-NMR-PH-729-1: (300 MHz, CDCl₃, ppm): δ4.01-3.94 (m, 1H), 3.75-3.72 (m, 4H), 3.17-3.07 (m, 1H), 2.56-2.51 (m, 4H), 2.42-2.37 (m, 1H), 1.89-1.83 (m, 2H), 1.68-1.53 (m, 3H), 1.48 (s, 9H), 1.27 (d, J=6.3 Hz, 3H).

Synthesis of 4-(2-methylpiperidin-4-yl)morpholine: Into a 250-mL round-bottom flask, was placed tert-butyl 2-methyl-4-(morpholin-4-yl)piperidine-1-carboxylate (5 g, 17.58 mmol, 1.00 equiv), hydrogen chloride/Dioxane (50 mL). The resulting solution was stirred for 30 min at room temperature. The resulting mixture was concentrated under vacuum. The resulting mixture was diluted with MeCN and based with potassium carbonate. The mixture was filtered and the filtrate was concentrated. This resulted in 3 g (93%) of 4-(2-methylpiperidin-4-yl)morpholine as a white solid. LC-MS-729-2: (ES, m/z): 185 [M+H]⁺.

Synthesis of benzyl N-[4-[2-methyl-4-(morpholin-4-yl)piperidin-1-yl]-3-nitrophenyl]carbamate, Into a 250-mL round-bottom flask, was placed 4-(2-methylpiperidin-4-yl)morpholine (3 g, 16.28 mmol, 1.00 equiv), benzyl N-(4-fluoro-3-nitrophenyl)carbamate (5.6 g, 19.29 mmol, 1.20 equiv), potassium carbonate (6.75 g, 48.91 mmol, 3.00 equiv), MeCN (60 mL). The resulting solution was stirred overnight at 90° C. The solids were collected by filtration. The resulting mixture was concentrated under vacuum and applied onto a silica gel column with ethyl acetate/petroleum ether (75:25). The crude product was purified by Flash-Prep-HPLC with MeCN:0.1% TFA/H₂O=20/80 increasing to MeCN:0.1% TFA/H₂O=45/55 within 12 min. This resulted in 1.5 g (21%) of benzyl N-[4-[2-methyl-4-(morpholin-4-yl)piperidin-1-yl]-3-nitrophenyl]carbamate as a yellow solid. LC-MS-729-3: (ES, m/z): 455 [M+H]⁺. ¹H-NMR-PH-729-3: (300 MHz, d₆-DMSO, ppm): δ10.21 (s, 1H), 9.90 (br s, 1H), 7.87 (s, 1H), 7.64-7.52 (m, 2H), 7.50-7.30 (m, 5H), 5.18 (s, 2H), 4.10-3.96 (m, 2H), 3.80-3.60 (m, 2H), 3.55-3.30 (m, 3H), 3.20-2.97 (m, 4H), 2.69 (t, J=11.1 Hz, 1H), 2.25-2.10 (m, 2H), 1.75-1.55 (m, 1H), 1.40-1.30 (m, 1H), 0.74 (d, J=6.0 Hz, 3H).

Synthesis of benzyl N-[3-amino-4-[2-methyl-4-(morpholin-4-yl)piperidin-1-yl]phenyl]carbamate: Into a 100-mL round-bottom flask, was placed benzyl N-[4-[2-methyl-4-(morpholin-4-yl)piperidin-1-yl]-3-nitrophenyl]carbamate (1.2 g, 2.64 mmol, 1.00 equiv), Zn (1.0 g, 15.38 mmol, 6.00 equiv), NH₄Cl (1.7 g, 31.78 mmol, 12.00 equiv), MeOH (15 mL). The resulting solution was stirred for 1 h at room temperature. The solids were collected by filtration. The filtrate was concentrated under vacuum. The residue was applied onto a silica gel column with dichloromethane/methanol (15:1). This resulted in 0.84 g (75%) of benzyl N-[3-amino-4-[2-methyl-4-(morpholin-4-yl)piperidin-1-yl]phenyl]carbamate as a brown solid. LC-MS-729-4: (ES, m/z): 425 [M+H]⁺.

Synthesis of benzyl N-(3-[[(tert-butoxy)carbonyl]amino]-4-[2-methyl-4-(morpholin-4-yl)piperidin-1-yl]phenyl)carbamate Into a 250-mL round-bottom flask, was placed benzyl N-[3-amino-4-[2-methyl-4-(morpholin-4-yl)piperidin-1-yl]phenyl]carbamate (0.5 g, 3.53 mmol, 1.00 equiv), Boc₂O (0.38 g, 5.28 mmol, 1.50 equiv), DIEA (0.38 g, 8.84 mmol, 2.50 equiv), tetrahydrofuran (15 mL). The resulting solution was stirred overnight at 75° C. The reaction mixture was cooled to room temperature. The resulting mixture was concentrated under vacuum. The residue was applied onto a silica gel column with ethyl acetate/petroleum ether (75:25). This resulted in 0.5 g (80%) of benzyl N-(3-[[(tert-butoxy)carbonyl]amino]-4-[2-methyl-4-(morpholin-4-yl)piperidin-1-yl]phenyl)carbamate as a light yellow solid. LC-MS-729-5: (ES, m/z): 252 [M+H]⁺ ¹H-NMR-PH-729-5: (300 MHz, d₆-DMSO, ppm): δ9.69 (s, 1H), 8.19 (s, 1H), 8.05 (s, 1H), 7.46-7.30 (m, 5H), 7.18-7.15 (m, 1H), 7.10-7.06 (m, 1H), 5.14 (s, 2H), 3.59 (br s, 4H), 2.90-2.47 (m, 4H), 2.42-2.25 (m, 2H), 2.0-1.82 (m, 2H), 1.72-1.60 (m, 1H), 1.50-1.32 (m, 12H), 0.71 (d, J=6.0 Hz, 3H).

Synthesis of tert-butyl N-[5-amino-2-[2-methyl-4-(morpholin-4-yl)piperidin-1-yl]phenyl]carbamate: Into a 250-mL round-bottom flask purged and maintained with an inert atmosphere of H₂, was placed benzyl N-(3-[[(tert-butoxy)carbonyl]amino]-4-[2-methyl-4-(morpholin-4-yl)piperidin-1-yl]phenyl)carbamate (500 mg, 1.52 mmol, 1.00 equiv), Palladium carbon (50 mg), methanol (30 mL). The resulting solution was stirred for 3 h at 25° C. The mixture was concentrated under vacuum. This resulted in 381 mg (crude) of tert-butyl N-[5-amino-2-[2-methyl-4-(morpholin-4-yl)piperidin-1-yl]phenyl]carbamate as colorless oil. LC-MS-729-6: (ES, m/z): 391 [M+H]⁺.

Synthesis of tert-butyl N-[5-[(6-bromo-4-methyl-3-oxo-3,4-dihydropyrazin-2-yl)amino]-2-[2-methyl-4-(morpholin-4-yl)piperidin-1-yl]phenyl]carbamate: Into a 100-mL round-bottom flask, was placed tert-butyl N-[5-amino-2-[2-methyl-4-(morpholin-4-yl)piperidin-1-yl]phenyl]carbamate (300 mg, 1.54 mmol, 1 equiv), 3,5-dibromo-1-methyl-1,2-dihydropyrazin-2-one (250 mg, 1.87 mmol, 1.21 equiv), DIEA (250 mg, 3.87 mmol, 2.52 equiv), i-PrOH (10 mL). The resulting solution was stirred overnight at 80° C. The reaction mixture was cooled to room temperature. The resulting mixture was concentrated. The residue was applied onto a silica gel column with ethyl acetate. This resulted in 265 mg (59.73%) of tert-butyl N-[5-[(6-bromo-4-methyl-3-oxo-3,4-dihydropyrazin-2-yl)amino]-2-[2-methyl-4-(morpholin-4-yl)piperidin-1-yl]phenyl]carbamate as a yellow solid. LC-MS-729-7: (ES, m/z): 577 [M+H]$^+$. $^1$H-NMR-PH-729-7: (300 MHz, d$_6$-DMSO, ppm): δ9.38 (s, 1H), 8.41 (s, 1H), 8.04 (s, 1H), 7.59-7.55 (m, 1H), 7.32 (s, 1H), 7.23 (d, J=0.9 Hz, 1H), 3.65-3.55 (m, 4H), 3.44 (s, 3H), 2.92-2.52 (m, 4H), 2.42-2.28 (m, 2H), 2.00-1.82 (m, 2H), 1.50-1.30 (m, 13H), 0.73-0.69 (m, 3H).

Synthesis of 3-([3-amino-4-[2-methyl-4-(morpholin-4-yl) piperidin-1-yl]phenyl]amino)-5-bromo-1-methyl-1,2-dihydropyrazin-2-one: Into a 25-mL round-bottom flask, was placed tert-butyl N-[5-[(6-bromo-4-methyl-3-oxo-3,4-dihydropyrazin-2-yl)amino]-2-[2-methyl-4-(morpholin-4-yl)piperidin-1-yl]phenyl]carbamate (200 mg, 0.31 mmol, 1 equiv), HCl/Dioxane (5 mL). The resulting solution was stirred for 4 hr at room temperature. The resulting mixture was concentrated. This resulted in 160 mg (96.45%) of 3-([3-amino-4-[2-methyl-4-(morpholin-4-yl)piperidin-1-yl] phenyl]amino)-5-bromo-1-methyl-1,2-dihydropyrazin-2-one as a light yellow solid. LC-MS-729-8: (ES, m/z): 477 [M+H]$^+$.

Synthesis of 10-(4-[6-[(3-aminophenyl)amino]-4-methyl-5-oxo-4,5-dihydropyrazin-2-yl]-3-[(oxan-2-yloxy)methyl] pyridin-2-yl)-4,4-dimethyl-1,10-diazatricyclo [6.4.0.0ˆ [2,6]]dodeca-2(6),7-dien-9-one: Into a 25-mL round-bottom flask purged and maintained with an inert atmosphere of nitrogen, was placed 3-([3-amino-4-[2-methyl-4-(morpholin-4-yl)piperidin-1-yl]phenyl]amino)-5-bromo-1-methyl-1, 2-dihydropyrazin-2-one (160 mg, 0.34 mmol, 1 equiv), (2-[4,4-dimethyl-9-oxo-1,10-diazatricyclo[6.4.0.0ˆ[2,6]]dodeca-2(6),7-dien-10-yl]-3-[(oxan-2-yloxy)methyl]pyridin-4-yl)boronic acid (147 mg, 0.33 mmol, 1.00 equiv), Pd(dppf)Cl$_2$ (30 mg, 0.03 mmol, 0.10 equiv), K$_2$CO$_3$ (116 mg, 0.84 mmol, 2.50 equiv), dioxane (5 mL, Infinity mmol, Infinity equiv), H$_2$O (0.5 mL). The resulting solution was stirred for 40 min at 90° C. The reaction mixture was cooled to room temperature. The resulting mixture was concentrated and purified by Flash-Prep-HPLC. This resulted in 210 mg (79.12%) of 10-(4-[6-[(3-aminophenyl)amino]-4-methyl-5-oxo-4,5-dihydropyrazin-2-yl]-3-[(oxan-2-yloxy) methyl]pyridin-2-yl)-4,4-dimethyl-1,10-diazatricyclo [6.4.0.0ˆ [2,6]]dodeca-2(6),7-dien-9-one as a solid. LC-MS-729-9: (ES, m/z): 792 [M+H]$^+$.

Synthesis of 10-(4-[6-[(3-aminophenyl)amino]-4-methyl-5-oxo-4,5-dihydropyrazin-2-yl]-3-(hydroxymethyl)pyridin-2-yl)-4,4-dimethyl-1,10-diazatricyclo[6.4.0.0ˆ[2,6]]dodeca-2(6),7-dien-9-one: Into a 50-mL round-bottom flask, was placed 10-(4-[6-[(3-aminophenyl)amino]-4-methyl-5-oxo-4,5-dihydropyrazin-2-yl]-3-[(oxan-2-yloxy)methyl]pyridin-2-yl)-4,4-dimethyl-1,10-diazatricyclo [6.4.0.0ˆ[2,6]]dodeca-2(6),7-dien-9-one (200 mg, 0.38 mmol, 1.00 equiv), trifluoroacetic acid (1 mL), dichloromethane (20 mL). The resulting solution was stirred for 30 min at room temperature. The resulting mixture was concentrated under vacuum. The resulting solution was diluted with ethyl acetate and based with aq. sodium bicarbonate. The solids were filtered out and the filtrate was concentrated under vacuum. This resulted in 130 mg (76%) of 10-(4-[6-[(3-aminophenyl) amino]-4-methyl-5-oxo-4,5-dihydropyrazin-2-yl]-3-(hydroxymethyl)pyridin-2-yl)-4,4-dimethyl-1,10-diazatricyclo [6.4.0.0ˆ[2,6]]dodeca-2(6),7-dien-9-one as colorless oil. LC-MS-729-10: (ES, m/z): 708 [M+H]$^+$.

Synthesis of N-(3-[[6-(2-[4,4-dimethyl-9-oxo-1,10-diazatricyclo[6.4.0.0ˆ[2,6]]dodeca-2(6),7-dien-10-yl]-3-(hydroxymethyl)pyridin-4-yl)-4-methyl-3-oxo-3,4-dihydropyrazin-2-yl]amino]phenyl)prop-2-enamide: Into a 25-mL round-bottom flask, was placed 10-(4-[6-[(3-aminophenyl) amino]-4-methyl-5-oxo-4,5-dihydropyrazin-2-yl]-3-(hydroxymethyl)pyridin-2-yl)-4,4-dimethyl-1,10-diazatricyclo [6.4.0.0ˆ[2,6]]dodeca-2(6),7-dien-9-one (100 mg, 0.19 mmol, 1.00 equiv), prop-2-enoic acid (13.7 mg, 0.19 mmol, 1.00 equiv), NMM (38.5 mg, 0.38 mmol, 2.00 equiv), HATU (94 mg, 0.25 mmol, 1.30 equiv), MeCN (5 mL). The resulting solution was stirred for 30 min at room temperature. The crude product was purified by Prep-HPLC. This resulted in 19.7 mg (18%) of N-(3-[[6-(2-[4,4-dimethyl-9-oxo-1,10-diazatricyclo[6.4.0.0ˆ[2,6]]dodeca-2(6),7-dien-10-yl]-3-(hydroxymethyl)pyridin-4-yl)-4-methyl-3-oxo-3, 4-dihydropyrazin-2-yl]amino]phenyl)prop-2-enamide as off-white solid. LC-MS-729-0: (ES, m/z): 762 [M+H]$^+$. $^1$H-NMR-PH-729-0: (300 MHz, DMSO, ppm): δ9.23 (s, 2H), 9.14 (s, 1H), 8.49 (d, J=5.1 Hz, 1H), 7.96-7.95 (m, 1H), 7.77 (s, 1H), 7.61 (d, J=8.1 Hz, 1H), 7.23 (d, J=8.7 Hz, 1H), 6.68-6.62 (m, 1H), 6.57 (s, 1H), 6.30 (d, J=17.1 Hz, 1H), 5.80 (d, J=11.7 Hz, 1H), 5.03-5.00 (m, 1H), 4.65-4.40 (m, 2H), 4.32-4.16 (m, 4H), 3.85-3.83 (m, 1H), 3.68-3.55 (m, 7H), 3.01-2.72 (m, 2H), 2.71-2.52 (m, 4H), 2.48-2.25 (m, 4H), 1.98-1.78 (m, 2H), 1.72-1.52 (m, 1H), 1.46-1.30 (m, 1H), 1.23 (s, 6H), 0.76 (d, J=5.7 Hz, 3H).

Example 13: Preparation of (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino) pyrrolidin-1-yl)phenyl)acrylamide Synthesis of benzyl N-[4-[(3R)-3-(dimethylamino)pyrrolidin-1-yl]-3-nitrophenyl]carbamate as a yellow solid Into a 250-mL round-bottom flask, was placed (3R)—N,N-dimethylpyrrolidin-3-amine dihydrochloride (5 g, 26.72 mmol, 1 equiv), benzyl N-(4-fluoro-3-nitrophenyl)carbamate (9.3 g, 32.07 mmol, 1.20 equiv), TEA (10.8 g, 106.89 mmol, 4.00 equiv), DMF (80 mL). The resulting solution was stirred overnight at 100° C. The reaction mixture was cooled to room temperature. The reaction was then quenched by the addition of 200 mL of water. The resulting solution was extracted with 2×200 ml of ethyl acetate. The organic mixture was washed with 2×200 ml of brine. The organic phase was dried over anhydrous sodium sulfate. The solids were filtered out. The filtrate was concentrated under vacuum. The crude product was purified by re-crystallization from MeCN. This resulted in 5.2 g (50.62%) of benzyl N-[4-[(3R)-3-(dimethylamino)pyrrolidin-1-yl]-3-nitrophenyl]carbamate as a yellow solid. LC-MS-729-C-1: (ES, m/z): 385 [M+H]$^+$. $^1$H-NMR-PH-729-C-1: (300 MHz, d$_6$-DMSO, ppm): δ9.78 (s, 1H), 7.96 (s, 1H), 7.52-7.37 (m, 6H), 7.06 (d, J=9.3 Hz, 1H), 5.15 (s, 2H), 3.30-3.27 (m, 1H), 3.13-3.01 (m, 3H), 2.71-2.68 (m, 1H), 2.17 (s, 6H), 1.83-1.71 (m, 1H).

Synthesis of benzyl N-[3-amino-4-[3-(dimethylamino) pyrrolidin-1-yl]phenyl]carbamate: Into a 250-mL round-bottom flask, was placed benzyl N-[4-[3-(dimethylamino)pyrrolidin-1-yl]-3-nitrophenyl]carbamate (5 g, 13.01 mmol, 1 equiv), zinc (5.1 g, 78.04 mmol, 6.00 equiv), NH$_4$Cl (8.3 g, 156.07 mmol, 12.00 equiv), MeOH (100 mL). The resulting solution was stirred for 1 hr at room temperature. The resulting mixture was concentrated. This resulted in 3.9 g (84.60%) of benzyl N-[3-amino-4-[3-(dimethylamino)pyrrolidin-1-yl]phenyl]carbamate as a grey solid. LC-MS-729-C-2: (ES, m/z): 365 [M+H]$^+$.

Synthesis of benzyl N-(3-[[(tert-butoxy)carbonyl]amino]-4-[3-(dimethylamino)pyrrolidin-1-yl]phenyl)carbamate: Into a 250-mL round-bottom flask, was placed benzyl N-[3-amino-4-[3-(dimethylamino)pyrrolidin-1-yl]phenyl]carbamate (3 g, 16.93 mmol, 1 equiv), di-tert-butyl dicarbonate (2.2 mg, 20 mmol), DIEA (2.73 g, 40 mmol), THF (50 mL). The resulting solution was stirred overnight at 75° C. The reaction mixture was cooled to room temperature. The resulting mixture was concentrated. The residue was applied onto a silica gel column with ethyl acetate/petroleum ether (50:50). This resulted in 2.6 g (68%) of benzyl N-(3-[[(tert-butoxy)carbonyl]amino]-4-[3-(dimethylamino)pyrrolidin-1-yl]phenyl)carbamate as a yellow solid. LC-MS-729-C-3: (ES, m/z): 465 [M+H]$^+$. $^1$H-NMR-PH-729-C-3: (300 MHz, DMSO, ppm): δ9.51 (s, 1H), 8.06 (s, 1H), 7.54 (s, 1H), 7.41-7.33 (m, 5H), 7.14-7.11 (m, 1H), 6.89 (d, J=9.0 Hz, 1H), 5.13 (s, 2H), 3.21-3.12 (m, 1H), 3.09-2.99 (m, 3H), 2.79-2.69 (m, 1H), 2.17 (s, 6H), 2.09-2.00 (m, 1H), 1.78-1.65 (m, 1H), 1.44 (s, 9H).

Synthesis of tert-butyl N-[5-amino-2-[(3S)-3-(dimethylamino)pyrrolidin-1-yl]phenyl]carbamate: Into a 250-mL round-bottom flask purged and maintained with an inert atmosphere of H$_2$, was placed benzyl N-(3-[[(tert-butoxy)carbonyl]amino]-4-[(3S)-3-(dimethylamino)pyrrolidin-1-yl]phenyl)carbamate (2 g, 0.44 mmol, 1 equiv), Pd/C (200 mg), MeOH (50 mL). The resulting solution was stirred for 2 hr at room temperature. The solids were filtered out. The filtrate was concentrated under vacuum. The resulting mixture was concentrated. This resulted in 1.15 g of tert-butyl N-[5-amino-2-[(3S)-3-(dimethylamino)pyrrolidin-1-yl]phenyl]carbamate as brown oil. LC-MS-729-C-4: (ES, m/z): 321 [M+H]$^+$.

Synthesis of tert-butyl N-[5-[(6-bromo-4-methyl-3-oxo-3,4-dihydropyrazin-2-yl)amino]-2-[(3S)-3-(dimethylamino)pyrrolidin-1-yl]phenyl]carbamate: Into a 250-mL round-bottom flask, was placed tert-butyl N-[5-amino-2-[(3S)-3-(dimethylamino)pyrrolidin-1-yl]phenyl]carbamate (1 g, 1 equiv), 3,5-dibromo-1-methyl-1,2-dihydropyrazin-2-one (1 g, 1.20 equiv), DIEA (1 g, 2.49 equiv), i-PrOH (10 mL). The resulting solution was stirred overnight at 80° C. The reaction mixture was cooled to room temperature. The resulting mixture was concentrated. The residue was applied onto a silica gel column with EA/PE (50:50). This resulted in 1 g (60.62%) of tert-butyl N-[5-[(6-bromo-4-methyl-3-oxo-3,4-dihydropyrazin-2-yl)amino]-2-[(3S)-3-(dimethylamino) pyrrolidin-1-yl]phenyl]carbamate as a yellow solid. LC-MS-729-C-5: (ES, m/z): 507 [M+H]$^+$.

Synthesis of 3-([3-amino-4-[(3S)-3-(dimethylamino)pyrrolidin-1-yl]phenyl]amino)-5-bromo-1-methyl-1,2-dihydropyrazin-2-one: Into a 25-mL round-bottom flask, was placed tert-butyl N-[5-[(6-bromo-4-methyl-3-oxo-3,4-dihydropyrazin-2-yl)amino]-2-[(3S)-3-(dimethylamino)pyrrolidin-1-yl]phenyl]carbamate (1 g, 0.39 mmol, 1 equiv), HCl/Dioxane (10 mL). The resulting solution was stirred for 30 min at room temperature. The resulting mixture was concentrated. This resulted in 750 mg (93.43%) of 3-([3-amino-4-[(3S)-3-(dimethylamino)pyrrolidin-1-yl]phenyl]amino)-5-bromo-1-methyl-1,2-dihydropyrazin-2-one as a light yellow solid. LC-MS-729-C-6: (ES, m/z): 407 [M+H]$^+$.

Synthesis of N-[5-[(6-bromo-4-methyl-3-oxo-3,4-dihydropyrazin-2-yl)amino]-2-[3-(dimethylamino)pyrrolidin-1-yl]phenyl]prop-2-enamide: Into a 50-mL round-bottom flask, was placed 3-([3-amino-4-[3-(dimethylamino)pyrrolidin-1-yl]phenyl]amino)-5-bromo-1-methyl-1,2-dihydropyrazin-2-one (600 mg, 1.96 mmol, 1 equiv), prop-2-enoic acid (127.2 mg, 2.36 mmol, 1.2 equiv), HATU (672 mg, 2.36 mmol, 1.2 equiv), NMM (596 mg, 7.86 mmol, 4.0 equiv), MeCN (15 mL). The resulting solution was stirred for 30 min at room temperature. The resulting mixture was concentrated. The crude product was purified by Prep-HPLC. This resulted in 307 mg (45.25%) of N-[5-[(6-bromo-4-methyl-3-oxo-3,4-dihydropyrazin-2-yl)amino]-2-[3-(dimethylamino)pyrrolidin-1-yl]phenyl]prop-2-enamide as a light yellow solid. LC-MS-729-C-1: (ES, m/z): 461 [M+H]$^+$.

Synthesis of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino)pyrrolidin-1-yl)phenyl)acrylamide: Into a 25-mL round-bottom flask purged and maintained with an inert atmosphere of nitrogen, was placed N-[5-[(6-bromo-4-methyl-3-oxo-3,4-dihydropyrazin-2-yl)amino]-2-[(3S)-3-(dimethylamino) pyrrolidin-1-yl]phenyl]prop-2-enamide (50 mg, 0.11 mmol, 1 equiv), (2-[4,4-dimethyl-9-oxo-1,10-diazatricyclo [6.4.0.0$^{2,6}$]] dodeca-2(6),7-dien-10-yl]-3-(hydroxymethyl)pyridin-4-yl) boronic acid (50.0 mg, 0.14 mmol, 1.3 equiv), Pd(dppf)Cl$_2$ (9.3 mg, 0.01 mmol, 0.1 equiv), K$_2$CO$_3$ (37.4 mg, 0.27 mmol, 2.5 equiv), dioxane (5 mL), H$_2$O (0.5 mL). The resulting solution was stirred for 1 hr at 90° C. The reaction mixture was cooled to room temperature. The solids were filtered out. The filtrate was concentrated. The crude product was purified by Prep-HPLC. This resulted in 14 mg (18.67%) of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino)pyrrolidin-1-yl)phenyl)acrylamide as a white solid. LC-MS-729-C-0: (ES, m/z): 692 [M+H]$^+$. $^1$H-NMR-PH-729-C-0: (300 MHz, DMSO, ppm): δ9.38 (d, J=5.1 Hz, 1H), 9.17 (s, 1H), 8.44 (d, J=5.1 Hz, 1H), 8.34-8.32 (m, 1H), 7.76-7.63 (m, 3H), 6.86 (d, J=8.7 Hz, 1H), 6.62-6.48 (m, 2H), 6.27 (d, J=16.2 Hz, 1H), 5.73 (d, J=11.4 Hz, 1H), 5.05-4.95 (m, 1H), 4.70-4.38 (m, 2H), 4.29-4.20 (m, 3H), 3.89-3.84 (m, 1H), 3.55 (s, 3H), 3.14-3.07 (m, 3H), 2.74-2.49 (m, 6H), 2.15 (s, 6H), 2.05 (m, 1H), 1.75-1.69 (m, 1H), 1.23 (s, 6H).

Example 14: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(piperidin-3-yl)phenyl)acrylamide Synthesis of tert-butyl 3-(4-amino-2-nitrophenyl)-5,6-dihydro-2H-pyridine-1-carboxylate: Into a 500-mL round-bottom flask purged and maintained with an inert atmosphere of nitrogen, was placed tert-butyl 3-(4,4,5,5-tetramethyl-1,3,2-dioxaborolan-2-yl)-5,6-dihydro-2H-pyridine-1-carboxylate (8.55 g, 27.647 mmol, 1.20 equiv), 4-bromo-3-nitroaniline (5.00 g, 23.039 mmol, 1.00 equiv), Pd(dppf)Cl$_2$·CH$_2$Cl$_2$ (1.88 g, 2.304 mmol, 0.10 equiv), K$_2$CO$_3$ (6.37 g, 46.091 mmol, 2.00 equiv), dioxane (80.00 mL), H$_2$O (20.00 mL). The resulting solution was stirred for 2 h at 100° C. The solids were filtered out. The combined organic layer was concentrated. The residue was applied onto a silica gel column with ethyl acetate/petroleum ether (60:40). This resulted in 7 g (95.14%) of tert-butyl 3-(4-amino-2-nitrophenyl)-5,6-dihydro-2H-pyridine-1-carboxylate as a white solid. LC-MS-751-1: (ES, m/z): 320 [M+H]$^+$.

Synthesis of tert-butyl 3-(4-[[(benzyloxy)carbonyl] amino]-2-nitrophenyl)-5,6-dihydro-2H-pyridine-1-carboxylate: Into a 250-mL 3-necked round-bottom flask, was placed tert-butyl 3-(4-amino-2-nitrophenyl)-5,6-dihydro-2H-pyridine-1-carboxylate (7.00 g, 21.919 mmol, 1.00 equiv), Na$_2$CO$_3$ (4.65 g, 43.838 mmol, 2.00 equiv), DCM (50.00 mL). This was followed by the addition of H$_2$O (10.00 mL) stirred at 0° C. To this was added benzyl chloroformate (4.49 g, 26.303 mmol, 1.20 equiv) at 0° C. The resulting solution was stirred for overnight at room temperature. The reaction was then quenched by the addition of water. The mixture was dried over anhydrous sodium sulfate and concentrated. This resulted in 9 g of tert-butyl 3-(4-[[(benzyloxy)carbonyl]amino]-2-nitrophenyl)-5,6-dihydro-2H-pyridine-1-carboxylate as a light yellow oil. LC-MS-751-2: (ES, m/z): 454 [M+H]$^+$.

Synthesis of tert-butyl 3-(2-amino-4-[[(benzyloxy)carbonyl]amino]phenyl)-5,6-dihydro-2H-pyridine-1-carboxylate: Into a 100-mL round-bottom flask, was placed tert-butyl 3-(4-[[(benzyloxy)carbonyl]amino]-2-nitrophenyl)-5,6-dihydro-2H-pyridine-1-carboxylate (5.00 g, 11.025 mmol, 1.00 equiv), Fe (3.08 g, 55.127 mmol, 5.00 equiv), CH$_3$COOH (20.00 mL), H$_2$O (2.00 mL). The resulting solution was stirred for 1 h at 60° C. The resulting mixture was concentrated. The resulting solution was extracted with ethyl acetate The pH value of the solution was adjusted to 7 with NaHCO$_3$. The resulting mixture was washed with brine. The mixture was dried over anhydrous sodium sulfate and concentrated. The residue was applied onto a silica gel column with ethyl acetate/petroleum ether (60:40). This resulted in 4 g (85.66%) of tert-butyl 3-(2-amino-4-[[(benzyloxy)carbonyl]amino]phenyl)-5,6-dihydro-2H-pyridine-1-carboxylate as a yellow solid. LC-MS-751-3: (ES, m/z): 424 [M+H]$^+$. $^1$H NMR-751-3: (300 MHz, DMSO-d$_6$, ppm): δ9.49 (s, 1H), 7.49-7.32 (m, 5H), 6.88 (d, J=2.0 Hz, 1H), 6.76 (d, J=8.2 Hz, 1H), 6.61 (dd, J=8.2, 2.1 Hz, 1H), 5.78-5.70 (s, 1H), 5.13 (s, 2H), 4.84 (s, 2H), 3.89 (d, J=2.7 Hz, 2H), 3.48 (t, J=5.6 Hz, 2H), 2.25-2.13 (s, 2H), 1.42 (s, 9H).

Synthesis of tert-butyl 3-(4-[[(benzyloxy)carbonyl] amino]-2-[(tert-butoxycarbonyl)amino]phenyl)-5,6-dihydro-2H-pyridine-1-carboxylate: Into a 250-mL round-bottom flask, was placed tert-butyl 3-(2-amino-4-[[(benzyloxy)carbonyl]amino]phenyl)-5,6-dihydro-2H-pyridine-1-carboxylate (4.00 g, 9.445 mmol, 1.00 equiv), di-tert-butyl dicarbonate (4.12 g, 18.890 mmol, 2.00 equiv), K$_2$CO$_3$ (2.61 g, 18.885 mmol, 2.00 equiv), dioxane (80.00 mL), H$_2$O (40.00 mL). The resulting solution was stirred for overnight at room temperature. The reaction was then quenched by the addition of water. The resulting solution was extracted with ethyl acetate. The resulting mixture was washed with brine. The mixture was dried over anhydrous sodium sulfate and concentrated. The residue was applied onto a silica gel column with ethyl acetate/petroleum ether (40:60). This resulted in 5 g (101.10%) of tert-butyl 3-(4-[[(benzyloxy) carbonyl]amino]-2-[(tert-butoxycarbonyl)amino]phenyl)-5,6-dihydro-2H-pyridine-1-carboxylate as a white solid. LC-MS-751-4: (ES, m/z): 524 [M+H]$^+$. $^1$H NMR-751-4: (300 MHz, DMSO-d$_6$, ppm): δ9.79 (s, 1H), 8.31 (s, 1H), 7.51 (d, J=2.1 Hz, 1H), 7.50-7.31 (m, 5H), 7.25 (dd, J=8.4, 2.2 Hz, 1H), 7.07 (d, J=8.4 Hz, 1H), 5.69 (s, 1H), 5.16 (s, 2H), 3.97 (s, 2H), 3.45 (t, J=5.7 Hz, 2H), 2.18 (s, 2H), 1.42 (s, 18H).

Synthesis of tert-butyl 3-[4-amino-2-[(tert-butoxycarbonyl)amino]phenyl]piperidine-1-carboxylate: Into a 250-mL round-bottom flask purged and maintained with an inert atmosphere of nitrogen, was placed tert-butyl3-(4-[[(benzyloxy)carbonyl]amino]-2-[(tert-butoxycarbonyl)amino]phenyl)-5,6-dihydro-2H-pyridine-carboxylate (5.00 g, 9.549 mmol, 1.00 equiv), Pd/C (500.00 mg), MeOH (100 mL), EA (50.00 mL). The resulting solution was stirred for overnight at rt. The solids were collected by filtration. The combined organic layer was concentrated. This resulted in 3.4 g (90.95%) of tert-butyl 3-[4-amino-2-[(tert-butoxycarbonyl) amino]phenyl]piperidine-1-carboxylate as colorless oil. LC-MS-751-5: (ES, m/z): 392 [M+H]$^+$.

Synthesis of tert-butyl 3-[4-[(6-bromo-4-methyl-3-oxopyrazin-2-yl)amino]-2-[(tert-butoxycarbonyl)amino] phenyl]piperidine-1-carboxylate: Into a 250-mL round-bottom flask, was placed tert-butyl 3-[4-amino-2-[(tert-butoxycarbonyl)amino]phenyl]piperidine-1-carboxylate (3.40 g, 8.684 mmol, 1.00 equiv), 3,5-dibromo-1-methylpyrazin-2-one (2.56 g, 9.553 mmol, 1.1 equiv), i-PrOH (50.00 mL), DIEA (2.24 g, 17.369 mmol, 2.0 equiv). The resulting solution was stirred for overnight at 90° C. The resulting mixture was concentrated. The residue was applied onto a silica gel column with ethyl acetate/petroleum ether (40:60). This resulted in 4 g (79.62%) of tert-butyl 3-[4-[(6-bromo-4-methyl-3-oxopyrazin-2-yl)amino]-2-[(tert-butoxycarbonyl)amino]phenyl]piperidine-1-carboxylate as a light yellow solid.

LC-MS-751-6: (ES, m/z): 578 [M+H]$^+$.

Synthesis of 3-[[3-amino-4-(piperidin-3-yl)phenyl] amino]-5-bromo-1-methylpyrazin-2-one: Into a 250-mL round-bottom flask, was placed tert-butyl 3-[4-[(6-bromo-4-methyl-3-oxopyrazin-2-yl) amino]-2-[(tert-butoxycarbonyl)amino]phenyl]piperidine-1-carboxylate (4.00 g). To the above HCl (g)/MeOH (80.00 mL) was added. The resulting solution was stirred for 2 hr at room temperature. The resulting mixture was concentrated. This resulted in 2.9 g of 3-[[3-amino-4-(piperidin-3-yl)phenyl]amino]-5-bromo-1-methylpyrazin-2-one as a white solid. LC-MS-751-7: (ES, m/z): 378 [M+H]$^+$.

Synthesis of tert-butyl 3-[2-amino-4-[(6-bromo-4-methyl-3-oxopyrazin-2-yl)amino]phenyl]piperidine-1-carboxylate: Into a 250-mL round-bottom flask, was placed 3-[[3-amino-4-(piperidin-3-yl)phenyl]amino]-5-bromo-1-methylpyrazin-2-one (2.90 g, 7.666 mmol, 1.00 equiv), Boc$_2$O (1.84 g, 8.431 mmol, 1.10 equiv), TEA (1.55 g, 15.333 mmol, 2.00 equiv), DCM (50 ml). The resulting solution was stirred for 1 overnight at room temperature. The resulting mixture was concentrated. The crude product was purified by re-crystallization from ethyl ether. This resulted in 2.5 g (68.17%) of tert-butyl 3-[2-amino-4-[(6-bromo-4-methyl-3-oxopyrazin-2-yl)amino]phenyl]piperidine-1-carboxylate as a white solid. LC-MS-751-8: (ES, m/z): 478 [M+H]$^+$. $^1$H NMR-751-8: (300 MHz, DMSO-d$_6$, ppm): δ 8.99 (s, 1H), 7.27 (s, 1H), 7.11-7.01 (m, 2H), 6.92 (d, J=9.0 Hz, 1H), 4.90 (s, 2H), 3.98 (s, 2H), 3.43 (s, 3H), 2.84-2.54 (m, 3H), 1.90-1.82 (m, 1H), 1.73-1.64 (m, 1H), 1.60-1.46 (m, 2H), 1.42 (s, 9H).

Synthesis of tert-butyl 3-[4-[(6-bromo-4-methyl-3-oxopyrazin-2-yl)amino]-2-(prop-2-enamido)phenyl]piperidine-1-carboxylate: Into a 25-mL round-bottom flask, was placed tert-butyl 3-[2-amino-4-[(6-bromo-4-methyl-3-oxopyrazin-2-yl)amino]phenyl]piperidine-1-carboxylate (500.00 mg, 1.045 mmol, 1.00 equiv), acryloyl chloride (141.90 mg, 1.568 mmol, 1.5 equiv), NMM (211.43 mg, 2.090 mmol, 2.00 equiv), DCM (10 mL). The resulting solution was stirred for 2 hr at room temperature. The resulting mixture was concentrated. The residue was applied onto a silica gel column with ethyl acetate/petroleum ether (70:30). This resulted in 300 mg (53.91%) of tert-butyl 3-[4-[(6-bromo-4-methyl-3-oxopyrazin-2-yl)amino]-2-

(prop-2-enamido)phenyl]piperidine-1-carboxylate as a yellow solid. LC-MS-751-9: (ES, m/z): 532 [M+H]+. 1H NMR-751-9: (300 MHz, DMSO-d6, ppm): δ9.67 (s, 1H), 9.47 (s, 1H), 7.86-7.75 (m, 2H), 7.36-7.25 (m, 2H), 6.58-6.43 (m, 1H), 6.24 (dd, J=17.0, 2.1 Hz, 1H), 5.75 (d, J=7.6 Hz, 1H), 4.10-3.81 (m, 2H), 3.44 (s, 3H), 2.83-2.62 (m, 3H), 1.87-1.76 (m, 1H), 1.70 (d, J=13.4 Hz, 1H), 1.65-1.50 (m, 1H), 1.37 (s, 9H).

Synthesis of tert-butyl 3-(4-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(prop-2-enamido)phenyl)piperidine-1-carboxylate: Into a 40-mL microwave tube and maintained with an inert atmosphere of nitrogen, was placed tert-butyl 3-[4-[(6-bromo-4-methyl-3-oxopyrazin-2-yl)amino]-2-(prop-2-enamido)phenyl]piperidine-1-carboxylate (300.00 mg, 0.563 mmol, 1.00 equiv), 2-[4,4-dimethyl-9-oxo-1,10-diazatricyclo[6.4.0.0^[2,6]]dodeca-2(6),7-dien-10-yl]-3-methylpyridin-4-ylboronic acid (248.46 mg, 0.732 mmol, 1.30 equiv), Pd(dppf)Cl2 CH2Cl2 (46.01 mg, 0.056 mmol, 0.10 equiv), K2CO3 (155.51 mg, 1.127 mmol, 2.00 equiv), DME (10.00 mL), H2O (2.00 mL). The resulting solution was stirred for 1 hr at 90° C. The resulting mixture was concentrated. The residue was applied onto a silica gel column with ethyl acetate/petroleum ether (40:60). This resulted in 240 mg (57.03%) of tert-butyl 3-(4-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(prop-2-enamido)phenyl)piperidine-1-carboxylate as a yellow solid. LC-MS-751-10: (ES, m/z): 747 [M+H]+.

Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(piperidin-3-yl)phenyl)prop-2-enamide-: Into a 25-mL round-bottom flask, was placed tert-butyl 3-(4-[[6-(2-[4,4-dimethyl-9-oxo-1,10-diazatricyclo [6.4.0.0^[2,6]]dodeca-2(6),7-dien-10-yl]-3-methylpyridin-4-yl)-4-methyl-3-oxopyrazin-2-yl]amino]-2-(prop-2-enamido)phenyl)piperidine-1-carboxylate (150.00 mg, 0.201 mmol, 1.00 equiv), DCM (8.00 mL), TFA (1.5. mL). The resulting solution was stirred for 2.5 hr at room temperature. The resulting mixture was concentrated. The reaction was then quenched by the addition of NaHCO3. The resulting solution was extracted with dichloromethane. The resulting mixture was washed with brine. The mixture was dried over anhydrous sodium sulfate and concentrated. The crude product was purified by Prep-HPLC. This resulted in 80 mg (61.59%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(piperidin-3-yl)phenyl)prop-2-enamide as a white solid. LC-MS-751-0: (ES, m/z): 647 [M+H]+. 1H NMR-751-0: (300 MHz, DMSO-d6, ppm): δ9.61 (s, 1H), 9.29 (s, 1H), 8.32 (d, J=5.0 Hz, 1H), 8.16 (d, J=7.2 Hz, 1H), 7.77 (d, J=8.5 Hz, 1H), 7.49 (d, J=4.8 Hz, 1H), 7.43 (s, 1H), 7.21 (d, J=8.6 Hz, 1H), 6.60-6.47 (m, 2H), 6.23 (d, J=16.6 Hz, 1H), 5.70 (d, J=10.2 Hz, 1H), 4.30-4.11 (m, 3H), 3.84 (d, J=12.5 Hz, 1H), 3.57 (s, 3H), 2.99-2.73 (m, 3H), 2.58 (d, J=5.5 Hz, 2H), 2.43 (s, 3H), 2.29 (s, 3H), 1.83-1.69 (m, 1H), 1.69-1.58 (m, 1H), 1.58-1.37 (m, 2H), 1.23 (s, 7H).

Example 15: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-methylpiperazine-1-carbonyl)phenyl)acrylamide Synthesis of methyl 2-amino-4-nitrobenzoate. Into a 100-mL round-bottom flask, was placed 2-amino-4-nitrobenzoic acid (2.00 g), SOCl2 (4.00 mL), MeOH (20.00 mL). The resulting solution was stirred for 3 hr at 55° C. The reaction mixture was cooled. The crude product was purified by re-crystallization from aether. The solids were collected by filtration. This resulted in 1 g of methyl 2-amino-4-nitrobenzoate as a yellow solid. LC-MS-752-1: (ES, m/z): 197 [M+H]+. 1H NMR-752-1: (300 MHz, CDCl3, ppm): δ8.02 (d, J=8.8 Hz, 1H), 7.53 (d, J=2.2 Hz, 1H), 7.42 (dd, J=8.8, 2.2 Hz, 1H), 6.05 (brs, 2H), 3.94 (s, 3H).

Synthesis of methyl 2-[bis(tert-butoxycarbonyl)amino]-4-nitrobenzoate: Into a 100-mL round-bottom flask, was placed methyl 2-amino-4-nitrobenzoate (1.00 g, 5.098 mmol, 1.00 equiv), Boc2O (3.34 g, 15.293 mmol, 3.00 equiv), TEA (1.03 g, 10.196 mmol, 2.00 equiv), DMAP (0.06 g, 0.510 mmol, 0.10 equiv), THF (20.00 mL). The resulting solution was stirred for 4 hr at room temperature. The reaction was then quenched by the addition of water. The resulting solution was extracted with ethyl acetate dried over anhydrous sodium sulfate and concentrated. This resulted in 1.8 g (89.08%) of methyl 2-[bis(tert-butoxycarbonyl)amino]-4-nitrobenzoate as a yellow solid. LC-MS-752-2: (ES, m/z): 397 [M+H]+. 1H NMR-752-2: (300 MHz, CDCl3, ppm): δ8.26 (dd, J=8.6, 2.2 Hz, 1H), 8.17 (d, J=8.6 Hz, 1H), 8.10 (d, J=2.2 Hz, 1H), 3.94 (s, 3H), 1.42 (s, 18H).

Synthesis of 2-[bis(tert-butoxycarbonyl)amino]-4-nitrobenzoic acid: Into a 100-mL round-bottom flask, was placed methyl 2-[bis(tert-butoxycarbonyl)amino]-4-nitrobenzoate (1.80 g, 1 equiv), LiOH (300.00 mg), H2O (4.00 mL), THF (20.00 mL). The resulting solution was stirred for 1 overnight at room temperature. The reaction was then quenched by the addition of 1N hydrochloric acid aqueous solution was added to the reaction solution and extracted with ethyl acetate. The organic layer was dried over anhydrous Na2SO4, concentrated. This resulted in 1 g (57.59%) of 2-[bis(tert-butoxycarbonyl)amino]-4-nitrobenzoic acid as a yellow solid.

LC-MS-752-3: (ES, m/z): 383 [M+H]+.

Synthesis of tert-butyl N-(tert-butoxycarbonyl)-N-[2-(4-methylpiperazine-1-carbonyl)-5-nitrophenyl]carbamate-: Into a 50-mL round-bottom flask, was placed 2-[bis(tert-butoxycarbonyl)amino]-4-nitrobenzoic acid (1.00 g, 2.615 mmol, 1.00 equiv), piperazine, 1-methyl- (0.31 g, 3.138 mmol, 1.20 equiv), HATU (1.49 g, 3.923 mmol, 1.50 equiv), NMM (0.53 g, 5.231 mmol, 2.00 equiv), DCM (15.00 mL). The resulting solution was stirred for 4 hr at room temperature. The resulting mixture was concentrated. The residue was applied onto a silica gel column with ethyl acetate/petroleum ether (100:1). This resulted in 500 mg (41.16%) of tert-butyl N-(tert-butoxycarbonyl)-N-[2-(4-methylpiperazine-1-carbonyl)-5-nitrophenyl]carbamate as a light yellow solid. LC-MS-752-4: (ES, m/z): 465 [M+H]+.

Synthesis of tert-butyl N-[5-amino-2-(4-methylpiperazine-1-carbonyl)phenyl]-N-(tert-butoxycarbonyl)carbamate: Into a 100-mL round-bottom flask purged and maintained with an inert atmosphere of H2, was placed tert-butyl N-(tert-butoxycarbonyl)-N-[2-(4-methylpiperazine-1-carbonyl)-5-nitrophenyl]carbamate (500.00 mg), MeOH (20.00 ml), Pd/C (500.00 mg). The resulting solution was stirred for 6 hr at room temperature. The solids were collected by filtration. The combined organic layer was concentrated. This resulted in 400 mg of tert-butyl N-[5-amino-2-(4-methylpiperazine-1-carbonyl)phenyl]-N-(tert-butoxycarbonyl)carbamate as colorless oil. LC-MS-752-5: (ES, m/z): 435 [M+H]+.

Synthesis of tert-butyl N-[5-[(6-bromo-4-methyl-3-oxopyrazin-2-yl)amino]-2-(4-methylpiperazine-1-carbonyl)phenyl]-N-(tert-butoxycarbonyl)carbamate: Into a 250-mL round-bottom flask purged and maintained with an inert atmosphere of nitrogen, was placed tert-butyl N-[5-amino-2-(4-methylpiperazine-1-carbonyl)phenyl]-N-(tert-butoxycarbonyl)carbamate (400.00 mg, 0.921 mmol, 1.00 equiv), 3,5-dibromo-1-methylpyrazin-2-one (369.92 mg, 1.381 mmol, 1.5 equiv), $Pd_2(dba)_3$ (168.59 mg, 0.184 mmol, 0.2 equiv), XantPhos (213.05 mg, 0.368 mmol, 0.4 equiv), $Cs_2CO_3$ (599.85 mg, 1.841 mmol, 2.0 equiv), Toluene (25.00 mL). The resulting solution was stirred for 4 hr at 100° C. The resulting mixture was concentrated. The residue was applied onto a silica gel column with ethyl acetate/petroleum ether (70:30). This resulted in 200 mg (34.96%) of tert-butyl N-[5-[(6-bromo-4-methyl-3-oxopyrazin-2-yl)amino]-2-(4-methylpiperazine-1-carbonyl)phenyl]-N-(tert-butoxycarbonyl)carbamate as a light yellow solid. LC-MS-752-6: (ES, m/z): 621 [M+H]$^+$.

Synthesis of 3-[[3-amino-4-(4-methylpiperazine-1-carbonyl)phenyl]amino]-5-bromo-1-methylpyrazin-2-one: Into a 50-mL round-bottom flask, was placed tert-butyl N-[5-[(6-bromo-4-methyl-3-oxopyrazin-2-yl)amino]-2-(4-methylpiperazine-1-carbonyl)phenyl]-N-(tert-butoxycarbonyl)carbamate (200.00 mg), HCl (gas) in 1,4-dioxane (10.00 mL). The resulting solution was stirred for 2 hr at room temperature. The resulting mixture was concentrated. This resulted in 120 mg of 3-[[3-amino-4-(4-methylpiperazine-1-carbonyl)phenyl]amino]-5-bromo-1-methylpyrazin-2-one as a white solid. LC-MS-752-7: (ES, m/z): 421 [M+H]$^+$.

Synthesis of N-[5-[(6-bromo-4-methyl-3-oxopyrazin-2-yl)amino]-2-(4-methylpiperazine-1-carbonyl)phenyl]prop-2-enamide: Into a 50-mL round-bottom flask, was placed 3-[[3-amino-4-(4-methylpiperazine-1-carbonyl)phenyl]amino]-5-bromo-1-methylpyrazin-2-one (120.00 mg, 0.285 mmol, 1.00 equiv), acryloyl chloride (28.36 mg, 0.313 mmol, 1.10 equiv), NMM (57.62 mg, 0.570 mmol, 2.00 equiv), DCM (10.00 mL). The resulting solution was stirred for 30 min at room temperature. The resulting mixture was concentrated. The crude product was purified by Flash-Prep-HPLC 0.1% $NH_3 \cdot H_2O$:MeCN=30% increasing to 0.1% $NH_3 \cdot H_2O$:MeCN=58% within 9 min. This resulted in 80 mg (59.09%) of N-[5-[(6-bromo-4-methyl-3-oxopyrazin-2-yl)amino]-2-(4-methylpiperazine-1-carbonyl)phenyl]prop-2-enamide as a white solid. LC-MS-752-8: (ES, m/z): 475 [M+H]$^+$.

Synthesis of -752-0: Into a 8-mL vial purged and maintained with an inert atmosphere of nitrogen, was placed N-[5-[(6-bromo-4-methyl-3-oxopyrazin-2-yl)amino]-2-(4-methylpiperazine-1-carbonyl)phenyl]prop-2-enamide (80.00 mg, 0.168 mmol, 1.00 equiv), 2-[4,4-dimethyl-9-oxo-1,10-diazatricyclo[6.4.0.0^[2,6]]dodeca-2(6),7-dien-10-yl]-3-methylpyridin-4-ylboronic acid (73.00 mg, 0.219 mmol, 1.30 equiv), $Pd(dppf)Cl_2 \cdot CH_2Cl_2$ (13.74 mg, 0.017 mmol, 0.10 equiv), $K_2CO_3$ (46.52 mg, 0.337 mmol, 2.00 equiv), DME (8.00 mL), $H_2O$ (2.00 mL). The resulting solution was stirred for 1 hr at 90° C. The crude product was purified by Prep-HPLC. This resulted in 20 mg (17.23%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(4-methylpiperazine-1-carbonyl)phenyl)prop-2-enamide as a white solid. LC-MS-752-0: (ES, m/z): 690 [M+H]$^+$. $^1$H NMR-752-0: (300 MHz, DMSO-$d_6$, ppm): δ9.76 (s, 1H), 9.52 (s, 1H), 8.48 (s, 1H), 8.34 (d, J=5.0 Hz, 1H), 7.81 (dd, J=8.8, 1.8 Hz, 1H), 7.58-7.47 (m, 2H), 7.20 (d, J=8.5 Hz, 1H), 6.59-6.44 (m, 2H), 6.24 (dd, J=17.1, 1.8 Hz, 1H), 5.74 (dd, J=12.2, 2.4 Hz, 1H), 4.29-4.10 (m, 3H), 3.86 (d, J=11.9 Hz, 1H), 3.59 (s, 3H), 2.68-2.54 (m, 2H), 2.43 (s, 2H), 2.29 (s, 7H), 2.16 (s, 3H), 1.23 (s, 6H).

Example 16: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-1-morpholinopropan-2-yl)phenyl) acrylamide Synthesis of 5-bromo-1-methyl-3-([4-[2-methyl-1-(morpholin-4-yl)propan-2-yl]-3-nitrophenyl]amino)pyrazin-2-one: Into a 100-mL round-bottom flask purged and maintained with an inert atmosphere of nitrogen, was placed 4-[2-methyl-1-(morpholin-4-yl)propan-2-yl]-3-nitroaniline (400.00 mg, 1.432 mmol, 1.00 equiv), 3,5-dibromo-1-methylpyrazin-2-one (498.72 mg, 1.862 mmol, 1.30 equiv), $Pd_2(dba)_3$ (131.13 mg, 0.143 mmol, 0.10 equiv), XantPhos (165.71 mg, 0.286 mmol, 0.20 equiv), $Cs_2CO_3$ (933.11 mg, 2.864 mmol, 2.00 equiv), dioxane (20.00 mL). The resulting solution was stirred for 4 hr at 100° C. The solids were collected by filtration. The combined organic layer was concentrated. The crude product was purified by re-crystallization from MeCN. This resulted in 350 mg (52.41%) of 5-bromo-1-methyl-3-([4-[2-methyl-1-(morpholin-4-yl)propan-2-yl]-3-nitrophenyl]amino)pyrazin-2-one as a brown solid. LC-MS-753-1: (ES, m/z): 466 [M+H]$^+$. $^1$H NMR-753-1: (300 MHz, DMSO-$d_6$, ppm): δ9.90 (s, 1H), 8.19 (d, J=2.4 Hz, 1H), 8.08 (dd, J=8.9, 2.5 Hz, 1H), 7.62 (d, J=9.0 Hz, 1H), 7.43 (s, 1H), 3.53-3.39 (m, 7H), 2.53-2.47 (m, 2H), 2.23 (t, J=4.6 Hz, 4H), 1.29 (s, 6H).

Synthesis of 3-([3-amino-4-[2-methyl-1-(morpholin-4-yl)propan-2-yl]phenyl]amino)-5-bromo-1-methylpyrazin-2-one: Into a 100-mL round-bottom flask, was placed 5-bromo-1-methyl-3-([4-[2-methyl-1-(morpholin-4-yl)propan-2-yl]-3-nitrophenyl]amino)pyrazin-2-one (350.00 mg, 0.751 mmol, 1.00 equiv), $CH_3COOH$ (1352.13 mg, 22.516 mmol, 30.00 equiv), Zn (736.37 mg, 11.258 mmol, 15.00 equiv), EtOH (30.00 mL). The resulting solution was stirred for 2 hr at room temperature. The solids were collected by filtration. The combined organic layer was concentrated. The resulting solution was extracted with ethyl acetate The resulting mixture was washed with brine. The mixture was dried over anhydrous sodium sulfate and concentrated. This resulted in 300 mg (91.60%) of 3-([3-amino-4-[2-methyl-1-(morpholin-4-yl)propan-2-yl]phenyl]amino)-5-bromo-1-methylpyrazin-2-one as brown oil. LC-MS-753-2: (ES, m/z): 436 [M+H]$^+$.

Synthesis of N-[5-[(6-bromo-4-methyl-3-oxopyrazin-2-yl)amino]-2-[2-methyl-1-(morpholin-4-yl)propan-2-yl]phenyl]prop-2-enamide: Into a 100-mL round-bottom flask, was placed 3-([3-amino-4-[2-methyl-1-(morpholin-4-yl)propan-2-yl]phenyl]amino)-5-bromo-1-methylpyrazin-2-one (300.00 mg, 0.688 mmol, 1.00 equiv), acryloyl chloride (74.67 mg, 0.825 mmol, 1.20 equiv), NMM (139.08 mg, 1.375 mmol, 2.00 equiv), DCM (10.00 mL). The resulting solution was stirred for 30 min at room temperature. The resulting mixture was concentrated. The crude product was purified by Flash-Prep-HPLC 0.1% $NH_4HCO_3$:MeCN=30% increasing to 0.1% $NH_4HCO_3$:MeCN=70% within 9 min. This resulted in 260 mg (77.11%) of N-[5-[(6-bromo-4-methyl-3-oxopyrazin-2-yl)amino]-2-[2-methyl-1-(morpholin-4-yl)propan-2-yl]phenyl]prop-2-enamide as a white solid. LC-MS-753-3: (ES, m/z): 490 [M+H]$^+$. $^1$H NMR-753-3: (300 MHz, DMSO-$d_6$, ppm): δ10.75 (s, 1H), 9.40 (s, 1H), 7.95 (s, 1H), 7.77 (d, J=8.5 Hz, 1H), 7.39-7.25 (m, 2H), 6.61-6.44 (m, 1H), 6.27 (dd, J=16.9, 2.1 Hz, 1H), 5.81 (d, J=11.0 Hz, 1H), 3.54 (s, 4H), 3.44 (s, 3H), 2.36 (s, 4H), 1.35 (s, 6H).

Synthesis of N-(5-[[6-(2-[4,4-dimethyl-9-oxo-1,10-diazatricyclo[6.4.0.0ˆ[2,6]]dodeca-2(6),7-dien-10-yl]-3-methylpyridin-4-yl)-4-methyl-3-oxopyrazin-2-yl]amino]-2-[2-methyl-1-(morpholin-4-yl)propan-2-yl]phenyl)prop-2-enamide: Into a 40-mL microwave and maintained with an inert atmosphere of nitrogen, was placed N-[5-[(6-bromo-4-methyl-3-oxopyrazin-2-yl)amino]-2-[2-methyl-1-(morpholin-4-yl)propan-2-yl]phenyl]prop-2-enamide (200.00 mg, 0.408 mmol, 1.00 equiv), 2-[4,4-dimethyl-9-oxo-1,10-diazatricyclo[6.4.0.0ˆ[2,6]]dodeca-2(6),7-dien-O-yl]-3-methylpyridin-4-ylboronic acid (193.67 mg, 0.571 mmol, 1.40 equiv), Pd(dppf)Cl$_2$ CH$_2$Cl$_2$ (33.30 mg, 0.041 mmol, 0.10 equiv), K$_2$CO$_3$ (112.73 mg, 0.816 mmol, 2.00 equiv), DME (10.00 mL), H$_2$O (2.00 mL). The resulting solution was stirred for 2 hr at 95° C. The crude product was purified by Prep-HPLC. This resulted in 150 mg (52.18%) of N-(5-[[6-(2-[4,4-dimethyl-9-oxo-1,10-diazatricyclo[6.4.0.0ˆ[2,6]]dodeca-2(6),7-dien-2-yl]-3-methylpyridin-4-yl)-4-methyl-3-oxopyrazin-2-yl]amino]-2-[2-methyl-(morpholin-4-yl)propan-2-yl]phenyl)prop-2-enamide as a light brown solid. LC-MS-753-0: (ES, m/z): 705 [M+H]$^+$. $^1$H NMR-753-0: (300 MHz, DMSO-d6, ppm): δ10.78 (s, 1H), 9.26 (s, 1H), 8.38-8.29 (m, 2H), 7.69 (d, J=8.6 Hz, 1H), 7.54 (d, J=5.2 Hz, 1H), 7.43 (s, 1H), 7.28 (d, J=8.8 Hz, 1H), 6.58-6.45 (m, 2H), 6.27 (d, J=16.8 Hz, 1H), 5.76 (d, J=10.2 Hz, 1H), 4.31-4.10 (m, 3H), 3.84 (d, J=12.4 Hz, 1H), 3.57 (s, 3H), 3.57-3.47 (m, 4H), 2.58 (d, J=5.8 Hz, 2H), 2.43 (s, 2H), 2.34 (d, J=4.7 Hz, 4H), 2.29 (s, 3H), 1.34 (d, J=4.2 Hz, 6H), 1.23 (s, 6H).

Example A: The compounds below are prepared by methods substantially identical, similar, or analogous to those disclosed in the General Scheme and above Examples.

| Compound | Name | m/z(MH$^+$) |
|---|---|---|
| A-1 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(tetrahydro-2H-pyran-4-yl)piperazin-1-yl)phenyl)acrylamide, | 746 |
| A-2 | (S)-N-(2-(4-(4,4-difluorocyclohexyl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)phenyl)acrylamide, | 810 |
| A-3 | N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-((2S)-2-methyl-4-morpholinopiperidin-1-yl)phenyl)acrylamide | 776 |
| A-4 | N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-morpholinopiperidin-1-yl)phenyl)acrylamide, | 762 |
| A-5 | N-(2-(4,4-difluoro-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)phenyl)acrylamide, | 796 |
| A-6 | N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(4-methylpiperazin-1-yl)piperidin-1-yl)phenyl)acrylamide, | 775 |
| A-8 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-fluoro-2-(2-methyl-4-(oxetan-3-yl)piperazin-1-yl)phenyl)acrylamide, | 736 |
| A-9 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-methyl-2-(2-methyl-4-(oxetan-3-yl)piperazin-1-yl)phenyl)acrylamide. | 732 |
| A-10 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)-3-(trifluoromethyl)phenyl)acrylamide, | 786 |
| A-11 | (S)-N-(3-cyano-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, | 743 |
| A-12 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-(isopropylsulfonyl)-2-(2-methyl-4-(oxetan-3-yl)piperazin-1-yl)phenyl)acrylamide, | 824 |
| A-13 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)-3-((trifluoromethyl)sulfonyl)phenyl)acrylamide. | 850 |
| A-14 | N-(2-((2'S)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2- | 810 |

| Compound | Name | m/z(MH⁺) |
|---|---|---|
| | yl)amino)phenyl)acrylamide | |
| A-15 | N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-((2S)-2-methyl-4-(4-methylpiperazin-1-yl)piperidin-1-yl)phenyl)acrylamide. | 789 |

Biological Example 1: Binding Constant ($K_d$) Determination

The $K_d$ of the compounds were determined by KINOIVEscan™ assay, the industry's most comprehensive high-throughput system for screening compounds against large numbers of human kinases. KINOIVEscan™ assay is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag. The kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM nonbiotinylated affinity ligand) and incubated at room temperature with shaking for 30 minutes. The kinase concentration in the eluates was measured by qPCR. An 11-point 3-fold serial dilution of each test compound was prepared in 100% DMSO at 100× final test concentration and subsequently diluted to 1× in the assay (final DMSO concentration=1%). Most $K_d$ were determined using a compound top concentration=30,000 nM. If the initial Kd determined was <0.5 nM (the lowest concentration tested), the measurement was repeated with a serial dilution starting at a lower top concentration. A $K_d$ value reported as 40,000 nM indicates that the $K_d$ was determined to be >30,000 nM. Binding constants (Kds) were calculated with a standard dose-response curve using the Hill equation: Response=Background+(Signal−Background)/[1+($K_d^{Hill\ Slope}$/Dose$^{Hill\ Slope}$)]. The Hill Slope was set to −1. Curves were fitted using a non-linear least square fit with the Levenberg-Marquardt algorithm. Such assays, carried out with a range of doses of test compounds, allow the determination of an approximate $K_d$ value. Although the $K_d$ of the compounds of the present invention vary with structural change as expected, the activity generally exhibited by these agents is in the range of $K_d$=0.1-1000 nM.

Biological Example 2: In Vitro Dialysis Assay (Irreversibility Assay)

IC50 of the test compound, was determined in the presence of 0.1 nM Enzyme and 40 mM ATP. 0.003 mM Compound (39×IC50 @40 mM ATP) was pre-incubated with 2 nM BTK for 2 hr in assay buffer without ATP. The compound-enzyme complex was dialyzed against the same buffer supplemented with 40 mM ATP for 24 hr. Cumulative dialysis factor>160,000×. After dialysis, the BTK activity was measured in the presence 40 mM ATP and 1 mM substrate peptide and compared to that in non-dialyzed samples. Assay buffer: 100 mM HEPES, pH7.5; 0.1% BSA, 0.01% Triton-X 100; 5 mM $MgCl_2$; 1 mM DTT. In this study, Ibrutinib (a FDA approved irreversible BTK inhibitor) was used as a positive control and Saurosporine (a reversible BTK inhibitor) was used as a negative control. The following table shows the recovery after 24 hr dialysis.

In this assay, GDC-0853, a reversible BTK inhibitor, was used as a reference compound. GDC-0853, disclosure in WO 2013067274, is an orally bioavailable, selective, and reversible Bruton's tyrosine kinase (BTK) inhibitor with IC50s ranging from 2-9 nM for basophil activation, B cell receptor activation, and constitutive p-BTK activity in whole blood lysates.1,2 In rats, treatment for longer than 7 days leads to pancreatic toxicity but it does not occur in mice or dogs, even at higher doses. Formulations containing GDC-0853 were well-tolerated in Phase I clinical trials and are in additional clinical trials for rheumatoid arthritis, lupus erythematosus and other autoimmune diseases.

The data of the WT BTK dialysis assay clearly shows that Ibrutnib, Example 2, Example 3, Example 11, Example 12 are irreversible inhibitors of WT BTK, while GDC-0853 is a reversible WT BTK inhibitor.

| | Recovery after 24 h dialysis | Conclusion (WT BTK) |
|---|---|---|
| Ibrutninb | ~1% | Irreversible/covalent inhibition |
| Example 2 | ~1% | Irreversible/covalent inhibition |
| Example 3 | ~1% | Irreversible/covalent inhibition |
| Example 11 | ~1% | Irreversible/covalent inhibition |
| Example 12 | ~1% | Irreversible/covalent inhibition |
| GDC-0853 | ~100% | Reversible |

For the C481S BTK enzyme, Ibrutinib, and our compounds such as Example 2 reversibly bind to the C481S BTK since the Cysteine residue is not available any more for covalent binding.

Biological Example 3: Biochemical Enzymatic Assay (IC50) Against WT and C481S BTK A Caliper-based kinase assay (Caliper Life Sciences, Hopkinton, MA) was used to measure inhibition of WT and C481S Btk kinase activity of a compound of the present disclosure. Ibrutinib and ACP=196 was used as control compounds. Serial dilutions of test compounds were incubated with human recombinant WT BTK or C481S Btk (0.5 nM), ATP (16 μM) and a phosphoacceptor peptide substrate FAM-GEEPLYWSFPAKKK-NH2 (1 μM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated.

The following table shows the IC50 of WT BTK, C481S BTK, and the IC50 ratio of C481S vs WT BTK for Ibrunitib, ACP-196, certain compounds of the disclosure. As expected, both Ibrutinib and ACP-196 dramatically lost binding affinity to the C481S BTK enzyme: Ibrutinib is ×990 fold weaker in C481S BTK than that of WT BTK, and ACP-196 is ×483 fold weaker in C481S BTK than that of WT BTK. On the contrary, the inventor unexpectedly find that our compounds still potently inhibits the C481S BTK as compared to that of WT BTK. Example 2 is ×64 more potent than Ibrutinib and ×477 more potent than the ACT-196 in C481S BTK assay. These data suggest that our compounds such as Example 2 reversibly binds to BTK by a different mechanism from the conventional covalent BTK inhibitors such as Ibrutinib and ACP-196, and so might be an important option for those patients that become resistant to Ibrutinib and ACP-196 due to a mutation in the C481 binding site.

| Covalent BTKi | WT BTK IV50 (nM) (irreversible inhibition) | C481S BTK IC50 (nM) (reversible inhibition) |
| --- | --- | --- |
| Ibrutninb | 0.11 | 109 |
| ACP-196 | 1.68 | 812 |
| Example 2 | 0.25 | 1.7 |
| Example 3 | <1 | <1 |
| Example 11 | <1 | <1 |
| Example 12 | <1 | <1 |

Biological Example 4: Calcium Flux Fluorescence-Based Assay

Calcium flux fluorescence-based assays were performed in a FlexStation 11384 fluorometric imaging plate reader (Molecular Devices) according to manufacturer instructions. In brief, actively growing Ramos cells (ATCC) in RPMl medium supplemented with 10% FBS (Invitrogen) were washed and re-plated in low serum medium at approximately $5 \times 10^5$ cells per 100 μl per well in a 96-well plate. Compounds to be assayed were dissolved in DMSO and then diluted in low serum medium to final concentrations ranging from 0 to 10 μM (at a dilution factor of 0.3). The diluted compounds were then added to each well (final DMSO concentration was 0.01%) and incubated at 37 degree in 5% $CO_2$ incubator for one hour. Afterwards, 100 μl of a calcium-sensitive dye (from the Calcium 3 assay kit, Molecular Devices) was added to each well and incubated for an additional hour. The compound-treated cells were stimulated with a goat anti-human IgM antibody (80 ug/ml; Jackson ImmunoResearch) and read in the FlexStation 11384 using a $\lambda_{Ex}$=485 nm and $\lambda_{Em}$=538 nm for 200 seconds. The relative fluorescence unit (RFU) and the $IC_{50}$ were recorded and analyzed using a built-in SoftMax program (Molecular devices).

Biological Example 5: Inhibition of B-Cell Activation—B Cell FLIPR Assay in Ramos Cells Inhibition of B-cell activation by compounds of the present invention is demonstrated by determining the effect of the test compounds on anti-IgM stimulated B cell responses. The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mLl in growth media supplemented with IμM FLUO-3AM (TefLabs Cat-No. 0116, prepared in anhydrous DMSO and 10% Pluronic acid) in a tissue culture flask, and incubated at 37° C. (5% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 μM to 0.03 μM (7 concentrations, details below), and allowed to incubate with cells for 30 min at RT. Ramos cell $Ca^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480 nM excitation).

Growth Medium: RPMI 1640 medium with L-glutamine (Invitrogen, Cat-No. 61870-010), 10% Fetal Bovine Serum (FBS, Summit Biotechnology Cat-No. FP-100-05); ImM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528);

Assay and Analysis: Intracellular increases in calcium were reported using a max–min statistic (subtracting the resting baseline from the peak caused by addition of the stimulatory antibody using a Molecular Devices FLIPR control and statistic exporting software. The $IC_{50}$ was determined using a nonlinear curve fit (GraphPad Prism).

Biological Example 6: In Vitro Anti-Proliferation Assay

Cell antiproliferation is assayed by PerkinElmer ATPlite™ Luminescence Assay System. Briefly, the various test cancer cell lines are plated at a density of about $1 \times 10^4$ cells per well in Costar 96-well plates, and are incubated with different concentrations of compounds for about 72 hours in medium supplemented with 5% FBS. One lyophilized substrate solution vial is then reconstituted by adding 5 mL of substrate buffer solution, and is agitated gently until the solution is homogeneous. About 50 μL of mammalian cell lysis solution is added to 100 μL of cell suspension per well of a microplate, and the plate is shaken for about five minutes in an orbital shaker at –700 rpm. This procedure is used to lyse the cells and to stabilize the ATP. Next, 50 μL substrate solution is added to the wells and microplate is shaken for five minutes in an orbital shaker at ~700 rpm. Finally, the luminescence is measured by a PerkinElmer TopCount® Microplate Scintillation Counter. Such assays, carried out with a range of doses of test compounds, allow the determination of the cellular anti-antiproliferative $IC_{50}$ of the compounds of the present invention.

Biological Example 7: In Vivo Xenograft Studies

Typically, athymic nude mice (CD-1 nu/nu) or SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 $mm^3$, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant.

Biological Example 8: Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID). The developing inflammation of the paws and limb joints is quantified using a scoring system that involves the assessment of the 4 paws following the criteria described below:
Scoring:
 1=swelling and/or redness of paw or one digit.
 2=swelling in two or more joints.
 3=gross swelling of the paw with more than two joints involved.
 4=severe arthritis of the entire paw and digits.
Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Biological Example 9: Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID). The developing inflammation of the paws and limb joints is quantified using a scoring system that involves the assessment of the 4 paws following the criteria as described above. Evaluation are made on day 0 for baseline measurement and starting again at the first signs or swelling for up to three times per week until the end of the experiment. The arthritic index for each mouse is obtained by adding the four scores of the individual paws, giving a maximum score of 16 per animal.

Biological Example 10: Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100μl) is determined by Coulter Counter. For differential leukocyte counts, 50-200μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leukocyte count in the BAL of OA sensitized and challenged rats as compared to control levels.

What is claimed is:

1. A method for inhibiting Bruton's tyrosine kinase activity in a subject, wherein the method comprises administering to the subject in need thereof a therapeutically effective amount of a compound of Formula (I):

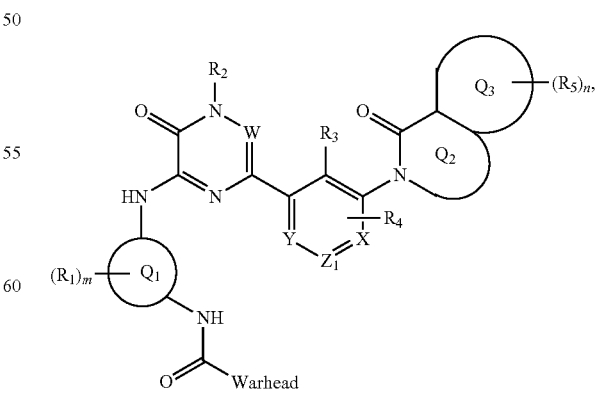

or a pharmaceutically acceptable salt, stereoisomer, or tautomer thereof, wherein:
Q$_1$ is a 5- or 6-membered aryl or a 5- or 6-membered heteroaryl;
Q$_2$ is a 5- to 7-membered heterocycloalkyl or a 5- to 7-membered heteroaryl;
Q$_3$ is a 5-membered heteroaryl;
W is CR$_a$;
X is CR$_a$ or N;
Y is CR$_a$ or N;
Z$_1$ is CR$_a$ or N;
Warhead is CH=CH$_2$, CH=CHCH$_2$N(CH$_3$)$_2$, or C≡CCH$_3$;
each R$_1$ is independently H, D, halo, cyano, nitro, alkyl, alkylene-R$_a$, alkylene-P(O)R$_b$R$_c$, alkenyl, alkynyl, C(O)R$_a$, C(O)NR$_b$R$_c$, C(O)OR$_a$, NH(CH$_2$)$_p$R$_a$, NR$_b$R$_c$, NR$_b$C(O)R$_c$, =NR$_b$, NR$_b$S(O)$_2$R$_c$, N=S(O)R$_b$R$_c$, OR$_a$, OC(O)R$_a$, =O, P(O)R$_b$R$_c$, SR$_a$, S(O)R$_a$, S(O)(NR$_b$)R$_c$, S(O)$_2$R$_a$, S(O)$_2$NR$_b$R$_c$, cycloalkyl, cycloalkenyl, heterocycloalkyl, spiroheterocycloalkyl, heterocycloalkenyl, aryl, or heteroaryl, wherein each cycloalkyl, cycloalkenyl, heterocycloalkyl, heterocycloalkenyl, aryl, and heteroaryl is optionally and independently substituted with one or more independently selected R$_d$ substituents; or
any two R$_1$, taken together with the atom(s) to which they are attached, independently form a cycloalkyl or heterocycloalkyl, wherein each cycloalkyl and heterocycloalkyl is optionally and independently substituted with one or more independently selected R$_d$ substituents;
R$_2$ is H or alkyl;
R$_3$ is H, halo, alkyl, haloalkyl, or hydroxyalkyl;
R$_4$ is H, halo, or lower alkyl;
each R$_5$ is independently H, D, halo, cyano, nitro, alkyl, alkylene-R$_a$, alkylene-P(O)R$_b$R$_c$, alkenyl, alkynyl, C(O)R$_a$, C(O)NR$_b$R$_c$, C(O)OR$_a$, NH(CH$_2$)$_p$R$_a$, NR$_b$R$_c$, NR$_b$C(O)R$_c$, =NR$_b$, NR$_b$S(O)$_2$R$_c$, N=S(O)R$_b$R$_c$, OR$_a$, OC(O)R$_a$, =O, P(O)R$_b$R$_c$, SR$_a$, S(O)R$_a$, S(O)(NR$_b$)R$_c$, S(O)$_2$R$_a$, S(O)$_2$NR$_b$R$_c$, cycloalkyl, cycloalkenyl, heterocycloalkyl, spiroheterocycloalkyl, heterocycloalkenyl, aryl, or heteroaryl, wherein each cycloalkyl, cycloalkenyl, heterocycloalkyl, heterocycloalkenyl, aryl, and heteroaryl is optionally and independently substituted with one or more independently selected R$_d$ substituents; or
any two R$_5$, taken together with the atom(s) to which they are attached, independently form a cycloalkyl or heterocycloalkyl, wherein each cycloalkyl and heterocycloalkyl is optionally and independently substituted with one or more independently selected R$_d$ substituents;
each R$_a$ is independently H, D, halo, cyano, nitro, alkyl, alkylene-P(O)R$_b$R$_c$, alkenyl, alkynyl, C(O)alkyl, C(O)NHOH, C(O)NH$_2$, C(O)OH, C(O)O(alkyl), NH$_2$, NH(alkyl), NH(haloalkyl), NHC(O)alkyl, =NR$_6$, N=S(O)R$_b$R$_c$, OH, O(alkyl), =O, P(O)R$_b$R$_c$, S(O)(NR$_b$)R$_c$, cycloalkyl, cycloalkenyl, heterocycloalkyl, spiroheterocycloalkyl, heterocycloalkenyl, aryl, or heteroaryl;
wherein each alkyl is optionally and independently substituted with one or more substituents independently selected from the group consisting of D, halo, cyano, nitro, C(O)alkyl, C(O)NHOH, C(O)O(alkyl), NH$_2$, NH(alkyl), NH(haloalkyl), NHC(O)alkyl, OH, O(alkyl), =O, cycloalkyl, cycloalkenyl, heterocycloalkyl, spiroheterocycloalkyl, heterocycloalkenyl, aryl, and heteroaryl; and
wherein each cycloalkyl, cycloalkenyl, heterocycloalkyl, heterocycloalkenyl, aryl, and heteroaryl is optionally and independently substituted with one or more independently selected R$_e$ substituents;
each R$_b$ is independently H, D, halo, cyano, nitro, alkyl, alkylene-P(O)R$_b$R$_c$, alkenyl, alkynyl, C(O)alkyl, C(O)NHOH, C(O)NH$_2$, C(O)OH, C(O)O(alkyl), NH$_2$, NH(alkyl), NH(haloalkyl), NHC(O)alkyl, =NR$_6$, N=S(O)R$_b$R$_c$, OH, O(alkyl), =O, P(O)R$_b$R$_c$, S(O)(NR$_b$)R$_c$, cycloalkyl, cycloalkenyl, heterocycloalkyl, spiroheterocycloalkyl, heterocycloalkenyl, aryl, or heteroaryl;
wherein each alkyl is optionally and independently substituted with one or more substituents independently selected from the group consisting of D, halo, cyano, nitro, C(O)alkyl, C(O)NHOH, C(O)O(alkyl), NH$_2$, NH(alkyl), NH(haloalkyl), NHC(O)alkyl, OH, O(alkyl), =O, cycloalkyl, cycloalkenyl, heterocycloalkyl, spiroheterocycloalkyl, heterocycloalkenyl, aryl, and heteroaryl; and
wherein each cycloalkyl, cycloalkenyl, heterocycloalkyl, heterocycloalkenyl, aryl, and heteroaryl is optionally and independently substituted with one or more independently selected R$_e$ substituents;
each R$_c$ is independently H, D, halo, cyano, nitro, alkyl, alkylene-P(O)R$_b$R$_c$, alkenyl, alkynyl, C(O)alkyl, C(O)NHOH, C(O)NH$_2$, C(O)OH, C(O)O(alkyl), NH$_2$, NH(alkyl), NH(haloalkyl), NHC(O)alkyl, =NR$_b$, N=S(O)R$_b$R$_c$, OH, O(alkyl), =O, P(O)R$_b$R$_c$, S(O)(NR$_b$)R$_c$, cycloalkyl, cycloalkenyl, heterocycloalkyl, spiroheterocycloalkyl, heterocycloalkenyl, aryl, or heteroaryl;
wherein each alkyl is optionally and independently substituted with one or more substituents independently selected from the group consisting of D, halo, cyano, nitro, C(O)alkyl, C(O)NHOH, C(O)O(alkyl), NH$_2$, NH(alkyl), NH(haloalkyl), NHC(O)alkyl, OH, O(alkyl), =O, cycloalkyl, cycloalkenyl, heterocycloalkyl, spiroheterocycloalkyl, heterocycloalkenyl, aryl, and heteroaryl; and
wherein each cycloalkyl, cycloalkenyl, heterocycloalkyl, heterocycloalkenyl, aryl, and heteroaryl is optionally and independently substituted with one or more independently selected R$_e$ substituents;
each R$_d$ is independently H, D, halo, cyano, nitro, alkyl, alkylene-P(O)R$_b$R$_c$, alkenyl, alkynyl, C(O)alkyl, C(O)NHOH, C(O)NH$_2$, C(O)OH, C(O)O(alkyl), NH$_2$, NH(alkyl), NH(haloalkyl), NHC(O)alkyl, =NR$_b$, N=S(O)R$_b$R$_c$, OH, O(alkyl), =O, P(O)R$_b$R$_c$, S(O)(NR$_b$)R$_c$, cycloalkyl, cycloalkenyl, heterocycloalkyl, spiroheterocycloalkyl, heterocycloalkenyl, aryl, or heteroaryl;
wherein each alkyl is optionally and independently substituted with one or more substituents independently selected from the group consisting of D, halo, cyano, nitro, C(O)alkyl, C(O)NHOH, C(O)O(alkyl), NH$_2$, NH(alkyl), NH(haloalkyl), NHC(O)alkyl, OH, O(alkyl), =O, cycloalkyl, cycloalkenyl, heterocycloalkyl, spiroheterocycloalkyl, heterocycloalkenyl, aryl, and heteroaryl; and wherein each cycloalkyl, cycloalkenyl, heterocycloalkyl, heterocycloalkenyl, aryl, and heteroaryl is optionally and independently substituted with one or more independently selected $R_e$ substituents;

each $R_e$ is independently D, halo, cyano, nitro, alkyl, haloalkyl, aminoalkyl, hydroxyalkyl, alkylene-O(alkyl), alkenyl, alkynyl, C(O)alkyl, C(O)NHOH, C(O)O(alkyl), $NH_2$, NH(alkyl), NH(haloalkyl), NHC(O)alkyl, OH, O(alkyl), =O, cycloalkyl, cycloalkenyl, heterocycloalkyl, spiroheterocycloalkyl, heterocycloalkenyl, aryl, or heteroaryl;

m is 0, 1, 2, 3, or 4;

n is 0, 1, 2, 3, or 4; and each p is independently 1, 2, 3, or 4.

2. The method according to claim 1, wherein the subject has a disease or disorder selected from the group consisting of an autoimmune disease, an inflammatory disorder, and a neoplastic disease.

3. The method according to claim 2, wherein the autoimmune disease or inflammatory disorder is selected from the group consisting of an allergy, asthma, multiple sclerosis, pemphigus vulgaris, rheumatoid arthritis (RA), and systemic lupus erythematosus.

4. The method according to claim 2, wherein the autoimmune disease or inflammatory disorder is selected from the group consisting of Addison's disease, an allergy, Alzheimer's disease, asthma, atherosclerosis, an autoimmune hemolytic state, an autoimmune thrombocytopenic state, chronic idiopathic thrombocytopenic purpura (ITP), Crohn's disease, dermatomyositis, diabetes, Goodpasture's syndrome, a hyperacute rejection of a transplanted organ, irritable bowel syndrome, multiple sclerosis, myasthenia gravis, Parkinson's disease, psoriasis, rheumatoid arthritis, scleroderma, septic shock, Sjogren's disease, systemic lupus erythematosus, tissue graft rejection, and vasculitis.

5. The method according to claim 4, wherein the autoimmune disease or inflammatory disorder is chronic idiopathic thrombocytopenic purpura (ITP).

6. The method according to claim 4, wherein the autoimmune disease or inflammatory disorder is multiple sclerosis.

7. The method according to claim 4, wherein the autoimmune disease or inflammatory disorder is rheumatoid arthritis.

8. The method according to claim 4, wherein the autoimmune disease or inflammatory disorder is systemic lupus erythematosus.

9. The method according to claim 4, wherein the systemic lupus erythematosus is associated with glomerulonephritis.

10. The method according to claim 4, wherein the Goodpasture's syndrome is associated with glomerulonephritis or a pulmonary hemorrhage.

11. The method according to claim 4, wherein the vasculitis is ANCA-associated vasculitis.

12. The method according to claim 2, wherein the neoplastic disease is a B-cell malignance or a solid tumor.

13. The method according to claim 2, wherein the neoplastic disease is selected from the group consisting of chronic lymphocytic leukemia (CLL), diffuse large B-cell lymphoma (DLBCL), mantle cell lymphoma (MCL), multiple myeloma (MM), and small lymphocytic lymphoma (SLL).

14. The method according to claim 13, wherein the neoplastic disease is chronic lymphocytic leukemia (CLL).

15. The method according to claim 13, wherein the neoplastic disease is diffuse large B-cell lymphoma (DLBCL).

16. The method according to claim 13, wherein the neoplastic disease is mantle cell lymphoma (MCL).

17. The method according to claim 13, wherein the neoplastic disease is multiple myeloma (MM).

18. The method according to claim 13, wherein the neoplastic disease is small lymphocytic lymphoma (SLL).

19. The method according to claim 2, wherein the neoplastic disease is selected from the group consisting of acute lymphocytic leukemia, acute myelogenous leukemia, chronic lymphocytic leukemia (CLL), chronic myelogenous leukemia, lymphoma, and multiple myeloma (MM).

20. The method according to claim 19, wherein the lymphoma is selected from the group consisting of B-cell lymphoma, hairy cell lymphoma, Hodgkin's lymphoma, mantle cell lymphoma (MCL), non-Hodgkin's lymphoma, and small lymphocytic lymphoma (SLL).

21. The method according to claim 20, wherein the B-cell lymphoma is diffuse large B-cell lymphoma (DLBCL).

22. The method according to claim 2, wherein the neoplastic disease is marginal zone lymphoma.

23. The method according to claim 2, wherein the neoplastic disease is Waldenstrom's macroglobulinemia.

* * * * *